US012216472B2

United States Patent
Vandike et al.

(10) Patent No.: US 12,216,472 B2
(45) Date of Patent: *Feb. 4, 2025

(54) MAP GENERATION AND CONTROL SYSTEM

(71) Applicant: Deere & Company, Moline, IL (US)

(72) Inventors: Nathan R. Vandike, Geneseo, IL (US); Bhanu Kiran Reddy Palla, Bettendorf, IA (US); Federico Pardina-Malbran, Fort Collins, CO (US); Matthew T. Wold, Coal Valley, IL (US); Cody W. Best, Silvis, IL (US); Noel W. Anderson, Fargo, ND (US)

(73) Assignee: Deere & Company, Moline, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/447,725

(22) Filed: Aug. 10, 2023

(65) Prior Publication Data

US 2023/0393577 A1    Dec. 7, 2023

Related U.S. Application Data

(63) Continuation of application No. 17/067,038, filed on Oct. 9, 2020, now Pat. No. 11,983,009.

(51) Int. Cl.
*G05D 1/00* (2024.01)
*A01D 41/127* (2006.01)
(Continued)

(52) U.S. Cl.
CPC ......... *G05D 1/0212* (2013.01); *A01D 41/127* (2013.01); *B60K 35/00* (2013.01);
(Continued)

(58) Field of Classification Search
CPC ............ G01C 21/3848; G01C 21/3889; G01C 21/00; G01C 21/3841; A01D 61/02;
(Continued)

(56) References Cited

U.S. PATENT DOCUMENTS 3,568,157 A    3/1971   Downing et al.
3,580,257 A    5/1971   Teague
(Continued)

FOREIGN PATENT DOCUMENTS

AR           108898 A1    10/2018
AU       20100224431 A1     4/2011
(Continued)

OTHER PUBLICATIONS

Application and Drawings for U.S. Appl. No. 16/171,978, filed Oct. 26, 2018, 53 pages.
(Continued)

*Primary Examiner* — Yuri Kan

(74) *Attorney, Agent, or Firm* — Christopher J. Volkmann; Kelly, Holt & Christenson, PLLC.

(57) ABSTRACT

One or more information maps are obtained by an agricultural work machine. The one or more information maps map one or more agricultural characteristic values at different geographic locations of a field. An in-situ sensor on the agricultural work machine senses an agricultural characteristic as the agricultural work machine moves through the field. A predictive map generator generates a predictive map that predicts a predictive agricultural characteristic at different locations in the field based on a relationship between the values in the one or more information maps and the agricultural characteristic sensed by the in-situ sensor. The predictive map can be output and used in automated machine control.

20 Claims, 20 Drawing Sheets

(51) Int. Cl.
*A01D 61/02* (2006.01)
*B60K 35/00* (2024.01)
*B60K 35/22* (2024.01)
*B60K 35/28* (2024.01)
*G01C 21/00* (2006.01)
*G01N 33/24* (2006.01)
*G05D 1/02* (2020.01)
*G05D 1/646* (2024.01)
*G06N 20/00* (2019.01)
*G01N 33/00* (2006.01)

(52) U.S. Cl.
CPC ..... *G01C 21/3807* (2020.08); *G01C 21/3848* (2020.08); *G05D 1/646* (2024.01); *B60K 35/22* (2024.01); *B60K 35/28* (2024.01); *B60K 2360/166* (2024.01); *G01N 33/0098* (2013.01); *G01N 33/246* (2013.01); *G06N 20/00* (2019.01)

(58) Field of Classification Search
CPC .......... G01N 33/24; B07B 4/04; B02C 25/00; A01B 79/005; A01B 19/04; B60K 31/0066; G05D 1/0276; G05D 1/0278; G05D 1/02; G05D 1/00; G05D 1/0221; G06Q 50/02
See application file for complete search history.

(56) References Cited

U.S. PATENT DOCUMENTS

| | | | |
|---|---|---|---|
| 3,599,543 A | 8/1971 | Kerridge | |
| 3,775,019 A | 11/1973 | Konig et al. | |
| 3,856,754 A | 12/1974 | Habermeier et al. | |
| 4,129,573 A | 12/1978 | Bellus et al. | |
| 4,166,735 A | 9/1979 | Pilgram et al. | |
| 4,183,742 A | 1/1980 | Sasse et al. | |
| 4,268,679 A | 5/1981 | Lavanish | |
| 4,349,377 A | 9/1982 | Durr et al. | |
| 4,360,677 A | 11/1982 | Doweyko et al. | |
| 4,435,203 A | 3/1984 | Funaki et al. | |
| 4,493,726 A | 1/1985 | Burdeska et al. | |
| 4,527,241 A | 7/1985 | Sheehan et al. | |
| 4,566,901 A | 1/1986 | Martin et al. | |
| 4,584,013 A | 4/1986 | Brunner | |
| 4,687,505 A | 8/1987 | Sylling et al. | |
| 4,857,101 A | 8/1989 | Musco et al. | |
| 4,911,751 A | 3/1990 | Nyffeler et al. | |
| 5,059,154 A | 10/1991 | Reyenga | |
| 5,089,043 A | 2/1992 | Hayase et al. | |
| 5,246,164 A | 9/1993 | McCann et al. | |
| 5,246,915 A | 9/1993 | Lutz et al. | |
| 5,250,690 A | 10/1993 | Turner et al. | |
| 5,296,702 A | 3/1994 | Beck et al. | |
| 5,300,477 A | 4/1994 | Tice | |
| 5,416,061 A | 5/1995 | Hewett et al. | |
| 5,477,459 A | 12/1995 | Clegg et al. | |
| 5,488,817 A | 2/1996 | Paquet et al. | |
| 5,563,112 A | 10/1996 | Barnes, III | |
| 5,585,626 A | 12/1996 | Beck et al. | |
| 5,586,033 A | 12/1996 | Hall | |
| 5,592,606 A | 1/1997 | Myers | |
| 5,606,821 A | 3/1997 | Sadjadi et al. | |
| 5,666,793 A | 9/1997 | Bottinger | |
| 5,712,782 A | 1/1998 | Weigelt et al. | |
| 5,721,679 A | 2/1998 | Monson | |
| 5,767,373 A | 6/1998 | Ward et al. | |
| 5,771,169 A | 6/1998 | Wendte | |
| 5,789,741 A | 8/1998 | Kinter et al. | |
| 5,809,440 A | 9/1998 | Beck et al. | |
| 5,841,282 A | 11/1998 | Christy et al. | |
| 5,849,665 A | 12/1998 | Gut et al. | |
| 5,878,821 A | 3/1999 | Flenker et al. | |
| 5,899,950 A | 5/1999 | Milender et al. | |
| 5,902,343 A | 5/1999 | Hale et al. | |
| 5,915,492 A | 6/1999 | Yates et al. | |
| 5,957,304 A | 9/1999 | Dawson | |
| 5,974,348 A | 10/1999 | Rocks | |
| 5,978,723 A | 11/1999 | Hale et al. | |
| 5,991,687 A | 11/1999 | Hale et al. | |
| 5,991,694 A | 11/1999 | Gudat et al. | |
| 5,995,859 A | 11/1999 | Takahashi | |
| 5,995,894 A | 11/1999 | Wendte | |
| 5,995,895 A * | 11/1999 | Watt | B60K 31/0066 56/10.2 G |
| 6,004,076 A | 12/1999 | Cook et al. | |
| 6,016,713 A | 1/2000 | Hale | |
| 6,029,106 A | 2/2000 | Hale et al. | |
| 6,041,582 A | 3/2000 | Tiede et al. | |
| 6,073,070 A | 6/2000 | Diekhans | |
| 6,073,428 A | 6/2000 | Diekhans | |
| 6,085,135 A | 7/2000 | Steckel | |
| 6,119,442 A | 9/2000 | Hale | |
| 6,119,531 A | 9/2000 | Wendte et al. | |
| 6,128,574 A | 10/2000 | Diekhans | |
| 6,141,614 A | 10/2000 | Janzen et al. | |
| 6,178,253 B1 | 1/2001 | Hendrickson et al. | |
| 6,185,990 B1 | 2/2001 | Missotten et al. | |
| 6,188,942 B1 | 2/2001 | Corcoran et al. | |
| 6,199,000 B1 | 3/2001 | Keller et al. | |
| 6,204,856 B1 | 3/2001 | Wood et al. | |
| 6,205,381 B1 | 3/2001 | Motz et al. | |
| 6,205,384 B1 | 3/2001 | Diekhans | |
| 6,216,071 B1 | 4/2001 | Motz | |
| 6,236,924 B1 | 5/2001 | Motz et al. | |
| 6,272,819 B1 | 8/2001 | Wendte et al. | |
| 6,327,569 B1 | 12/2001 | Reep | |
| 6,374,173 B1 | 4/2002 | Ehlbeck | |
| 6,380,745 B1 | 4/2002 | Anderson et al. | |
| 6,431,790 B1 | 8/2002 | Anderegg et al. | |
| 6,451,733 B1 | 9/2002 | Pidskalny et al. | |
| 6,505,146 B1 | 1/2003 | Blackmer | |
| 6,505,998 B1 | 1/2003 | Bullivant | |
| 6,539,102 B1 | 3/2003 | Anderson et al. | |
| 6,549,849 B2 | 4/2003 | Lange et al. | |
| 6,584,390 B2 | 6/2003 | Beck | |
| 6,591,145 B1 | 7/2003 | Hoskinson et al. | |
| 6,591,591 B2 | 7/2003 | Coers et al. | |
| 6,592,453 B2 | 7/2003 | Coers et al. | |
| 6,604,432 B1 | 8/2003 | Hamblen et al. | |
| 6,681,551 B1 | 1/2004 | Sheidler et al. | |
| 6,682,416 B2 | 1/2004 | Behnke et al. | |
| 6,687,616 B1 | 2/2004 | Peterson et al. | |
| 6,729,189 B2 | 5/2004 | Paakkinen | |
| 6,735,568 B1 | 5/2004 | Buckwalter et al. | |
| 6,834,550 B2 | 12/2004 | Upadhyaya et al. | |
| 6,838,564 B2 | 1/2005 | Edmunds et al. | |
| 6,846,128 B2 | 1/2005 | Sick | |
| 6,932,554 B2 | 8/2005 | Isfort et al. | |
| 6,999,877 B1 | 2/2006 | Dyer et al. | |
| 7,073,374 B2 | 7/2006 | Berkman | |
| 7,167,797 B2 | 1/2007 | Faivre et al. | |
| 7,167,800 B2 | 1/2007 | Faivre et al. | |
| 7,191,062 B2 | 3/2007 | Chi et al. | |
| 7,194,965 B2 | 3/2007 | Hickey et al. | |
| 7,211,994 B1 | 5/2007 | Mergen et al. | |
| 7,248,968 B2 | 7/2007 | Reid | |
| 7,255,016 B2 | 8/2007 | Burton | |
| 7,261,632 B2 | 8/2007 | Pirro et al. | |
| 7,302,837 B2 | 12/2007 | Wendt | |
| 7,308,326 B2 | 12/2007 | Maertens et al. | |
| 7,313,478 B1 | 12/2007 | Anderson et al. | |
| 7,318,010 B2 | 1/2008 | Anderson | |
| 7,347,168 B2 | 3/2008 | Reckels et al. | |
| 7,408,145 B2 | 8/2008 | Holland | |
| 7,480,564 B2 | 1/2009 | Metzler et al. | |
| 7,483,791 B2 | 1/2009 | Anderegg et al. | |
| 7,537,519 B2 | 5/2009 | Huster et al. | |
| 7,557,066 B2 | 7/2009 | Hills et al. | |
| 7,628,059 B1 | 12/2009 | Scherbring | |
| 7,687,435 B2 | 3/2010 | Witschel et al. | |
| 7,703,036 B2 | 4/2010 | Satterfield et al. | |
| 7,725,233 B2 | 5/2010 | Hendrickson et al. | |

(56) References Cited

U.S. PATENT DOCUMENTS

| | | |
|---|---|---|
| 7,733,416 B2 | 6/2010 | Gal |
| 7,756,624 B2 | 7/2010 | Diekhans et al. |
| 7,798,894 B2 | 9/2010 | Isfort |
| 7,827,042 B2 | 11/2010 | Jung et al. |
| 7,915,200 B2 | 3/2011 | Epp et al. |
| 7,945,364 B2 | 5/2011 | Schricker et al. |
| 7,993,188 B2 | 8/2011 | Ritter |
| 8,024,074 B2 | 9/2011 | Stelford et al. |
| 8,060,283 B2 | 11/2011 | Mott et al. |
| 8,107,681 B2 | 1/2012 | Gaal |
| 8,145,393 B2 | 3/2012 | Foster et al. |
| 8,147,176 B2 | 4/2012 | Coers et al. |
| 8,152,610 B2 | 4/2012 | Harrington |
| 8,190,335 B2 | 5/2012 | Vik et al. |
| 8,195,342 B2 | 6/2012 | Anderson |
| 8,195,358 B2 | 6/2012 | Anderson |
| 8,213,964 B2 | 7/2012 | Fitzner et al. |
| 8,224,500 B2 | 7/2012 | Anderson |
| 8,252,723 B2 | 8/2012 | Jakobi et al. |
| 8,254,351 B2 | 8/2012 | Fitzner et al. |
| 8,321,365 B2 | 11/2012 | Anderson |
| 8,329,717 B2 | 12/2012 | Minn et al. |
| 8,332,105 B2 | 12/2012 | Laux |
| 8,338,332 B1 | 12/2012 | Hacker et al. |
| 8,340,862 B2 | 12/2012 | Baumgarten et al. |
| 8,407,157 B2 | 3/2013 | Anderson et al. |
| 8,428,829 B2 | 4/2013 | Brunnert et al. |
| 8,478,493 B2 | 7/2013 | Anderson |
| 8,488,865 B2 | 7/2013 | Hausmann et al. |
| 8,494,727 B2 | 7/2013 | Green et al. |
| 8,527,157 B2 | 9/2013 | Imhof et al. |
| 8,544,397 B2 | 10/2013 | Bassett |
| 8,577,561 B2 | 11/2013 | Green et al. |
| 8,606,454 B2 | 12/2013 | Wang et al. |
| 8,626,406 B2 | 1/2014 | Schleicher et al. |
| 8,635,903 B2 | 1/2014 | Oetken et al. |
| 8,649,940 B2 | 2/2014 | Bonefas |
| 8,656,693 B2 | 2/2014 | Madsen et al. |
| 8,662,972 B2 | 3/2014 | Behnke et al. |
| 8,671,760 B2 | 3/2014 | Wallrath et al. |
| 8,677,724 B2 | 3/2014 | Chaney et al. |
| 8,738,238 B2 | 5/2014 | Rekow |
| 8,738,244 B2 | 5/2014 | Lenz |
| 8,755,976 B2 | 6/2014 | Peters et al. |
| 8,770,501 B2 * | 7/2014 | Laukka .................. B02C 25/00 241/34 |
| 8,781,692 B2 | 7/2014 | Kormann |
| 8,789,563 B2 | 7/2014 | Wenzel |
| 8,814,640 B2 | 8/2014 | Behnke et al. |
| 8,843,269 B2 | 9/2014 | Anderson et al. |
| 8,868,304 B2 | 10/2014 | Bonefas |
| 8,909,389 B2 | 12/2014 | Meyer |
| D721,740 S | 1/2015 | Schmaltz et al. |
| 8,942,860 B2 | 1/2015 | Morselli |
| 8,962,523 B2 | 2/2015 | Rosinger et al. |
| 9,002,591 B2 | 4/2015 | Wang et al. |
| 9,008,918 B2 | 4/2015 | Missotten et al. |
| 9,009,087 B1 | 4/2015 | Mewes et al. |
| 9,011,222 B2 | 4/2015 | Johnson et al. |
| 9,014,901 B2 | 4/2015 | Wang et al. |
| 9,043,096 B2 | 5/2015 | Zielke et al. |
| 9,043,129 B2 | 5/2015 | Bonefas et al. |
| 9,066,465 B2 | 6/2015 | Hendrickson et al. |
| 9,072,227 B2 | 7/2015 | Wenzel |
| 9,095,090 B2 | 8/2015 | Casper et al. |
| 9,119,342 B2 | 9/2015 | Bonefas |
| 9,127,428 B2 | 9/2015 | Meier |
| 9,131,644 B2 | 9/2015 | Osborne |
| 9,152,938 B2 | 10/2015 | Lang et al. |
| 9,173,339 B2 | 11/2015 | Sauder et al. |
| 9,179,599 B2 | 11/2015 | Bischoff |
| 9,188,518 B2 | 11/2015 | Snyder et al. |
| 9,188,986 B2 | 11/2015 | Baumann |
| 9,226,449 B2 | 1/2016 | Bischoff |
| 9,234,317 B2 | 1/2016 | Chi |
| 9,235,214 B2 | 1/2016 | Anderson |
| 9,301,447 B2 | 4/2016 | Kormann |
| 9,301,466 B2 | 4/2016 | Kelly |
| 9,313,951 B2 | 4/2016 | Herman et al. |
| 9,326,443 B2 | 5/2016 | Zametzer et al. |
| 9,326,444 B2 | 5/2016 | Bonefas |
| 9,392,746 B2 | 7/2016 | Darr et al. |
| 9,405,039 B2 | 8/2016 | Anderson |
| 9,410,840 B2 | 8/2016 | Acheson et al. |
| 9,439,342 B2 | 9/2016 | Pasquier |
| 9,457,971 B2 | 10/2016 | Bonefas et al. |
| 9,463,939 B2 | 10/2016 | Bonefas et al. |
| 9,485,905 B2 | 11/2016 | Jung et al. |
| 9,489,576 B2 | 11/2016 | Johnson et al. |
| 9,497,898 B2 | 11/2016 | Dillon |
| 9,510,508 B2 | 12/2016 | Jung |
| 9,511,633 B2 | 12/2016 | Anderson et al. |
| 9,511,958 B2 | 12/2016 | Bonefas |
| 9,516,812 B2 | 12/2016 | Baumgarten et al. |
| 9,521,805 B2 | 12/2016 | Muench et al. |
| 9,522,791 B2 | 12/2016 | Bonefas et al. |
| 9,522,792 B2 | 12/2016 | Bonefas et al. |
| 9,523,180 B2 | 12/2016 | Deines |
| 9,529,364 B2 | 12/2016 | Foster et al. |
| 9,532,504 B2 | 1/2017 | Herman et al. |
| 9,538,714 B2 | 1/2017 | Anderson |
| 9,563,492 B2 | 2/2017 | Bell et al. |
| 9,563,848 B1 | 2/2017 | Hunt |
| 9,563,852 B1 | 2/2017 | Wiles et al. |
| 9,578,808 B2 | 2/2017 | Dybro et al. |
| 9,629,308 B2 | 4/2017 | Schøler et al. |
| 9,631,964 B2 | 4/2017 | Gelinske et al. |
| 9,642,305 B2 | 5/2017 | Nykamp et al. |
| 9,648,807 B2 | 5/2017 | Escher et al. |
| 9,675,008 B1 | 6/2017 | Rusciolelli et al. |
| 9,681,605 B2 | 6/2017 | Noonan et al. |
| 9,694,712 B2 | 7/2017 | Healy et al. |
| 9,696,162 B2 | 7/2017 | Anderson |
| 9,699,967 B2 | 7/2017 | Palla et al. |
| 9,714,856 B2 | 7/2017 | Myers |
| 9,717,178 B1 | 8/2017 | Sauder et al. |
| 9,721,181 B2 | 8/2017 | Guan et al. |
| 9,723,790 B2 | 8/2017 | Berry et al. |
| 9,740,208 B2 | 8/2017 | Sugumaran et al. |
| 9,767,521 B2 | 9/2017 | Stuber et al. |
| 9,807,934 B2 | 11/2017 | Rusciolelli et al. |
| 9,807,940 B2 | 11/2017 | Roell et al. |
| 9,810,679 B2 | 11/2017 | Kimmel |
| 9,829,364 B2 | 11/2017 | Wilson et al. |
| 9,848,528 B2 | 12/2017 | Werner et al. |
| 9,856,609 B2 | 1/2018 | Dehmel |
| 9,856,612 B2 | 1/2018 | Oetken |
| 9,861,040 B2 | 1/2018 | Bonefas |
| 9,872,433 B2 | 1/2018 | Acheson et al. |
| 9,903,077 B2 | 2/2018 | Rio |
| 9,903,979 B2 | 2/2018 | Dybro et al. |
| 9,904,963 B2 | 2/2018 | Rupp et al. |
| 9,915,952 B2 | 3/2018 | Dollinger et al. |
| 9,922,405 B2 | 3/2018 | Sauder et al. |
| 9,924,636 B2 | 3/2018 | Lisouski et al. |
| 9,928,584 B2 | 3/2018 | Jens et al. |
| 9,933,787 B2 | 4/2018 | Story |
| 9,974,226 B2 | 5/2018 | Rupp et al. |
| 9,982,397 B2 | 5/2018 | Korb et al. |
| 9,984,455 B1 | 5/2018 | Fox et al. |
| 9,992,931 B2 | 6/2018 | Bonefas et al. |
| 9,992,932 B2 | 6/2018 | Bonefas et al. |
| 10,004,176 B2 | 6/2018 | Mayerle |
| 10,015,928 B2 | 7/2018 | Nykamp et al. |
| 10,019,018 B2 | 7/2018 | Hulin |
| 10,019,790 B2 | 7/2018 | Bonefas et al. |
| 10,025,983 B2 | 7/2018 | Guan et al. |
| 10,028,435 B2 | 7/2018 | Anderson et al. |
| 10,028,451 B2 | 7/2018 | Rowan et al. |
| 10,034,427 B2 | 7/2018 | Krause et al. |
| 10,039,231 B2 | 8/2018 | Anderson et al. |
| 10,064,331 B2 | 9/2018 | Bradley |
| 10,064,335 B2 | 9/2018 | Byttebier et al. |
| 10,078,890 B1 | 9/2018 | Tagestad et al. |

(56) References Cited

U.S. PATENT DOCUMENTS

| | | |
|---|---|---|
| 10,085,372 B2 | 10/2018 | Noyer et al. |
| 10,091,925 B2 | 10/2018 | Aharoni et al. |
| 10,126,153 B2 | 11/2018 | Bischoff et al. |
| 10,129,528 B2 | 11/2018 | Bonefas et al. |
| 10,143,132 B2 | 12/2018 | Inoue et al. |
| 10,152,035 B2 | 12/2018 | Reid et al. |
| 10,154,624 B2 | 12/2018 | Guan et al. |
| 10,165,725 B2 | 1/2019 | Sugumaran et al. |
| 10,178,823 B2 | 1/2019 | Kovach et al. |
| 10,183,667 B2 | 1/2019 | Anderson et al. |
| 10,188,037 B2 | 1/2019 | Bruns et al. |
| 10,194,574 B2 * | 2/2019 | Knobloch ............... A01B 19/04 |
| 10,201,121 B1 | 2/2019 | Wilson |
| 10,209,179 B2 | 2/2019 | Hollstein |
| 10,231,371 B2 | 3/2019 | Dillon |
| 10,254,147 B2 | 4/2019 | Vermue et al. |
| 10,254,765 B2 | 4/2019 | Rekow |
| 10,255,670 B1 | 4/2019 | Wu et al. |
| 10,275,550 B2 | 4/2019 | Lee |
| 10,295,703 B2 | 5/2019 | Dybro et al. |
| 10,310,455 B2 | 6/2019 | Blank et al. |
| 10,314,232 B2 | 6/2019 | Isaac et al. |
| 10,315,655 B2 * | 6/2019 | Blank ................... G05D 1/0276 |
| 10,317,272 B2 | 6/2019 | Bhavsar et al. |
| 10,351,364 B2 | 7/2019 | Green et al. |
| 10,368,488 B2 | 8/2019 | Becker et al. |
| 10,398,084 B2 | 9/2019 | Ray et al. |
| 10,408,545 B2 | 9/2019 | Blank et al. |
| 10,412,887 B2 * | 9/2019 | Füchtling ............... A01D 61/02 |
| 10,412,889 B2 | 9/2019 | Palla et al. |
| 10,426,086 B2 | 10/2019 | Van de Wege et al. |
| 10,437,243 B2 | 10/2019 | Blank et al. |
| 10,477,756 B1 | 11/2019 | Richt et al. |
| 10,485,178 B2 | 11/2019 | Mayerle |
| 10,521,526 B2 | 12/2019 | Haaland et al. |
| 10,537,061 B2 | 1/2020 | Farley et al. |
| 10,568,316 B2 | 2/2020 | Gall et al. |
| 10,631,462 B2 | 4/2020 | Bonefas |
| 10,677,637 B1 | 6/2020 | Von Muenster |
| 10,681,872 B2 | 6/2020 | Viaene et al. |
| 10,703,277 B1 | 7/2020 | Schroeder |
| 10,729,067 B2 | 8/2020 | Hammer et al. |
| 10,740,703 B2 | 8/2020 | Story |
| 10,745,868 B2 | 8/2020 | Laugwitz et al. |
| 10,760,946 B2 | 9/2020 | Meier et al. |
| 10,809,118 B1 | 10/2020 | Von Muenster |
| 10,830,634 B2 | 11/2020 | Blank et al. |
| 10,866,109 B2 | 12/2020 | Madsen et al. |
| 10,890,922 B2 | 1/2021 | Ramm et al. |
| 10,909,368 B2 | 2/2021 | Guo et al. |
| 10,912,249 B1 | 2/2021 | Wilson |
| 11,592,822 B2 * | 2/2023 | Vandike ............. G01C 21/3841 |
| 11,983,009 B2 * | 5/2024 | Vandike ................... G05D 1/00 |
| 2002/0011061 A1 | 1/2002 | Lucand et al. |
| 2002/0083695 A1 | 7/2002 | Behnke et al. |
| 2002/0091458 A1 | 7/2002 | Moore |
| 2002/0099471 A1 | 7/2002 | Benneweis |
| 2002/0133309 A1 | 9/2002 | Hardt |
| 2002/0173893 A1 | 11/2002 | Blackmore et al. |
| 2002/0193928 A1 | 12/2002 | Beck |
| 2002/0193929 A1 | 12/2002 | Beck |
| 2002/0198654 A1 | 12/2002 | Lange et al. |
| 2003/0004630 A1 | 1/2003 | Beck |
| 2003/0014171 A1 | 1/2003 | Ma et al. |
| 2003/0015351 A1 | 1/2003 | Goldman et al. |
| 2003/0024450 A1 | 2/2003 | Juptner et al. |
| 2003/0060245 A1 | 3/2003 | Coers et al. |
| 2003/0069680 A1 | 4/2003 | Cohen et al. |
| 2003/0075145 A1 | 4/2003 | Sheidler et al. |
| 2003/0174207 A1 | 9/2003 | Alexia et al. |
| 2003/0182144 A1 | 9/2003 | Pickett et al. |
| 2003/0187560 A1 | 10/2003 | Keller et al. |
| 2003/0216158 A1 | 11/2003 | Bischoff |
| 2003/0229432 A1 | 12/2003 | Ho et al. |
| 2003/0229433 A1 | 12/2003 | Van Den Berg et al. |
| 2003/0229435 A1 | 12/2003 | Van der Lely |
| 2004/0004544 A1 | 1/2004 | William Knutson |
| 2004/0054457 A1 | 3/2004 | Kormann |
| 2004/0073468 A1 | 4/2004 | Vyas et al. |
| 2004/0193348 A1 | 9/2004 | Gray et al. |
| 2005/0059445 A1 | 3/2005 | Niermann et al. |
| 2005/0066738 A1 | 3/2005 | Moore |
| 2005/0149235 A1 | 7/2005 | Seal et al. |
| 2005/0150202 A1 | 7/2005 | Quick |
| 2005/0197175 A1 | 9/2005 | Anderson |
| 2005/0241285 A1 | 11/2005 | Maertens et al. |
| 2005/0283314 A1 | 12/2005 | Hall |
| 2005/0284119 A1 | 12/2005 | Brunnert |
| 2006/0014489 A1 | 1/2006 | Fitzner et al. |
| 2006/0014643 A1 | 1/2006 | Hacker et al. |
| 2006/0047377 A1 | 3/2006 | Ferguson et al. |
| 2006/0058896 A1 | 3/2006 | Pokorny et al. |
| 2006/0074560 A1 | 4/2006 | Dyer et al. |
| 2006/0155449 A1 | 7/2006 | Dammann |
| 2006/0162631 A1 | 7/2006 | Hickey et al. |
| 2006/0196158 A1 | 9/2006 | Faivre et al. |
| 2006/0200334 A1 | 9/2006 | Faivre et al. |
| 2007/0005209 A1 | 1/2007 | Fitzner et al. |
| 2007/0021948 A1 | 1/2007 | Anderson |
| 2007/0056258 A1 | 3/2007 | Behnke |
| 2007/0068238 A1 | 3/2007 | Wendte |
| 2007/0073700 A1 | 3/2007 | Wippersteg et al. |
| 2007/0089390 A1 | 4/2007 | Hendrickson et al. |
| 2007/0135190 A1 | 6/2007 | Diekhans et al. |
| 2007/0185749 A1 | 8/2007 | Anderson et al. |
| 2007/0199903 A1 | 8/2007 | Denny |
| 2007/0208510 A1 | 9/2007 | Anderson et al. |
| 2007/0233348 A1 | 10/2007 | Diekhans et al. |
| 2007/0233374 A1 | 10/2007 | Diekhans et al. |
| 2007/0239337 A1 | 10/2007 | Anderson |
| 2007/0282523 A1 | 12/2007 | Diekhans et al. |
| 2007/0298744 A1 | 12/2007 | Fitzner et al. |
| 2008/0030320 A1 | 2/2008 | Wilcox et al. |
| 2008/0098035 A1 | 4/2008 | Wippersteg et al. |
| 2008/0140431 A1 | 6/2008 | Anderson et al. |
| 2008/0177449 A1 | 7/2008 | Pickett et al. |
| 2008/0192987 A1 * | 8/2008 | Helgason ............... G01N 33/24 |
| | | 382/109 |
| 2008/0248843 A1 | 10/2008 | Birrell et al. |
| 2008/0268927 A1 | 10/2008 | Farley et al. |
| 2008/0269052 A1 | 10/2008 | Rosinger et al. |
| 2008/0289308 A1 | 11/2008 | Brubaker |
| 2008/0312085 A1 | 12/2008 | Kordes et al. |
| 2009/0044505 A1 | 2/2009 | Huster et al. |
| 2009/0074243 A1 | 3/2009 | Missotten et al. |
| 2009/0143941 A1 | 6/2009 | Tarasinski et al. |
| 2009/0192654 A1 | 7/2009 | Wendte et al. |
| 2009/0216410 A1 | 8/2009 | Allen et al. |
| 2009/0226036 A1 | 9/2009 | Gaal |
| 2009/0259483 A1 | 10/2009 | Hendrickson et al. |
| 2009/0265098 A1 | 10/2009 | Dix |
| 2009/0306835 A1 | 12/2009 | Ellermann et al. |
| 2009/0311084 A1 | 12/2009 | Coers et al. |
| 2009/0312919 A1 | 12/2009 | Foster et al. |
| 2009/0312920 A1 | 12/2009 | Boenig et al. |
| 2009/0325658 A1 | 12/2009 | Phelan et al. |
| 2010/0036696 A1 | 2/2010 | Lang et al. |
| 2010/0042297 A1 | 2/2010 | Foster et al. |
| 2010/0063626 A1 | 3/2010 | Anderson |
| 2010/0063648 A1 | 3/2010 | Anderson |
| 2010/0063651 A1 | 3/2010 | Anderson |
| 2010/0063664 A1 | 3/2010 | Anderson |
| 2010/0063954 A1 | 3/2010 | Anderson |
| 2010/0070145 A1 | 3/2010 | Foster et al. |
| 2010/0071329 A1 | 3/2010 | Hindryckx et al. |
| 2010/0094481 A1 | 4/2010 | Anderson |
| 2010/0121541 A1 | 5/2010 | Behnke et al. |
| 2010/0137373 A1 | 6/2010 | Hungenberg et al. |
| 2010/0145572 A1 | 6/2010 | Steckel et al. |
| 2010/0152270 A1 | 6/2010 | Suty-Heinze et al. |
| 2010/0152943 A1 | 6/2010 | Matthews |
| 2010/0217474 A1 | 8/2010 | Baumgarten et al. |
| 2010/0268562 A1 | 10/2010 | Anderson |
| 2010/0268679 A1 | 10/2010 | Anderson |

(56) References Cited

U.S. PATENT DOCUMENTS

| | | |
|---|---|---|
| 2010/0285964 A1 | 11/2010 | Waldraff et al. |
| 2010/0317517 A1 | 12/2010 | Rosinger et al. |
| 2010/0319941 A1 | 12/2010 | Peterson |
| 2010/0332051 A1 | 12/2010 | Kormann |
| 2011/0056178 A1 | 3/2011 | Sauerwein et al. |
| 2011/0059782 A1 | 3/2011 | Harrington |
| 2011/0072773 A1 | 3/2011 | Schroeder et al. |
| 2011/0084851 A1 | 4/2011 | Peterson et al. |
| 2011/0086684 A1 | 4/2011 | Luellen et al. |
| 2011/0160961 A1 | 6/2011 | Wollenhaupt et al. |
| 2011/0213531 A1 | 9/2011 | Farley et al. |
| 2011/0224873 A1 | 9/2011 | Reeve et al. |
| 2011/0227745 A1 | 9/2011 | Kikuchi et al. |
| 2011/0257850 A1 | 10/2011 | Reeve et al. |
| 2011/0270494 A1 | 11/2011 | Imhof et al. |
| 2011/0270495 A1 | 11/2011 | Knapp |
| 2011/0295460 A1 | 12/2011 | Hunt et al. |
| 2011/0307149 A1 | 12/2011 | Pighi et al. |
| 2012/0004813 A1 | 1/2012 | Baumgarten et al. |
| 2012/0029732 A1 | 2/2012 | Meyer et al. |
| 2012/0087771 A1 | 4/2012 | Wenzel |
| 2012/0096827 A1 | 4/2012 | Chaney et al. |
| 2012/0143642 A1 | 6/2012 | O'Neil |
| 2012/0215378 A1 | 8/2012 | Sprock et al. |
| 2012/0215379 A1 | 8/2012 | Sprock et al. |
| 2012/0253611 A1 | 10/2012 | Zielke et al. |
| 2012/0263560 A1 | 10/2012 | Diekhans et al. |
| 2012/0265412 A1 | 10/2012 | Diekhans et al. |
| 2012/0271489 A1 | 10/2012 | Roberts et al. |
| 2012/0323452 A1 | 12/2012 | Green et al. |
| 2013/0019580 A1 | 1/2013 | Anderson et al. |
| 2013/0022430 A1 | 1/2013 | Anderson |
| 2013/0046419 A1 | 2/2013 | Anderson et al. |
| 2013/0046439 A1 | 2/2013 | Anderson et al. |
| 2013/0046525 A1 | 2/2013 | Ali et al. |
| 2013/0103269 A1 | 4/2013 | Meyer Zu Hellgen et al. |
| 2013/0124239 A1 | 5/2013 | Rosa et al. |
| 2013/0184944 A1 | 7/2013 | Missotten et al. |
| 2013/0197767 A1 | 8/2013 | Lenz |
| 2013/0205733 A1 | 8/2013 | Peters et al. |
| 2013/0210505 A1 | 8/2013 | Bischoff |
| 2013/0231823 A1 | 9/2013 | Wang et al. |
| 2013/0319941 A1 | 12/2013 | Schneider |
| 2013/0325242 A1 | 12/2013 | Cavender-Bares et al. |
| 2013/0332003 A1 | 12/2013 | Murray et al. |
| 2014/0002489 A1 | 1/2014 | Sauder et al. |
| 2014/0019017 A1 | 1/2014 | Wilken et al. |
| 2014/0021598 A1 | 1/2014 | Sutardja |
| 2014/0050364 A1 | 2/2014 | Brueckner et al. |
| 2014/0067745 A1 | 3/2014 | Avey |
| 2014/0102955 A1* | 4/2014 | Viny ................. B07B 4/04 209/645 |
| 2014/0121882 A1 | 5/2014 | Gilmore et al. |
| 2014/0129048 A1 | 5/2014 | Baumgarten et al. |
| 2014/0172222 A1 | 6/2014 | Nickel |
| 2014/0172224 A1 | 6/2014 | Matthews et al. |
| 2014/0172225 A1 | 6/2014 | Matthews et al. |
| 2014/0208870 A1 | 7/2014 | Quaderer et al. |
| 2014/0215984 A1 | 8/2014 | Bischoff |
| 2014/0230391 A1 | 8/2014 | Hendrickson et al. |
| 2014/0230392 A1 | 8/2014 | Dybro et al. |
| 2014/0236381 A1 | 8/2014 | Anderson et al. |
| 2014/0236431 A1 | 8/2014 | Hendrickson et al. |
| 2014/0257911 A1 | 9/2014 | Anderson |
| 2014/0262547 A1 | 9/2014 | Acheson et al. |
| 2014/0277960 A1 | 9/2014 | Blank et al. |
| 2014/0297242 A1 | 10/2014 | Sauder et al. |
| 2014/0303814 A1 | 10/2014 | Burema et al. |
| 2014/0324272 A1 | 10/2014 | Madsen et al. |
| 2014/0331631 A1 | 11/2014 | Sauder et al. |
| 2014/0338298 A1 | 11/2014 | Jung et al. |
| 2014/0350802 A1 | 11/2014 | Biggerstaff et al. |
| 2014/0360148 A1 | 12/2014 | Wienker et al. |
| 2015/0049088 A1 | 2/2015 | Snyder et al. |
| 2015/0088785 A1 | 3/2015 | Chi |
| 2015/0095830 A1 | 4/2015 | Massoumi et al. |
| 2015/0101519 A1 | 4/2015 | Blackwell et al. |
| 2015/0105984 A1 | 4/2015 | Birrell et al. |
| 2015/0124054 A1 | 5/2015 | Darr et al. |
| 2015/0168187 A1 | 6/2015 | Myers |
| 2015/0211199 A1 | 7/2015 | Corcoran et al. |
| 2015/0230403 A1 | 8/2015 | Jung et al. |
| 2015/0242799 A1 | 8/2015 | Seki et al. |
| 2015/0243114 A1 | 8/2015 | Tanabe et al. |
| 2015/0254800 A1 | 9/2015 | Johnson et al. |
| 2015/0264863 A1 | 9/2015 | Muench et al. |
| 2015/0276794 A1 | 10/2015 | Pistrol et al. |
| 2015/0278640 A1 | 10/2015 | Johnson et al. |
| 2015/0285647 A1 | 10/2015 | Meyer zu Helligen et al. |
| 2015/0293029 A1 | 10/2015 | Acheson et al. |
| 2015/0302305 A1 | 10/2015 | Rupp et al. |
| 2015/0305238 A1 | 10/2015 | Klausmann et al. |
| 2015/0305239 A1 | 10/2015 | Jung |
| 2015/0327440 A1 | 11/2015 | Dybro et al. |
| 2015/0351320 A1 | 12/2015 | Takahara et al. |
| 2015/0370935 A1 | 12/2015 | Starr |
| 2015/0373902 A1 | 12/2015 | Pasquier |
| 2015/0379785 A1 | 12/2015 | Brown, Jr. et al. |
| 2016/0025531 A1 | 1/2016 | Bischoff et al. |
| 2016/0029558 A1 | 2/2016 | Dybro et al. |
| 2016/0052525 A1 | 2/2016 | Tuncer et al. |
| 2016/0057922 A1 | 3/2016 | Freiberg et al. |
| 2016/0066505 A1 | 3/2016 | Bakke et al. |
| 2016/0073573 A1 | 3/2016 | Ethington et al. |
| 2016/0078375 A1 | 3/2016 | Ethington et al. |
| 2016/0078570 A1 | 3/2016 | Ethington et al. |
| 2016/0088794 A1 | 3/2016 | Baumgarten et al. |
| 2016/0106038 A1 | 4/2016 | Boyd et al. |
| 2016/0084813 A1 | 5/2016 | Anderson et al. |
| 2016/0146611 A1 | 5/2016 | Matthews |
| 2016/0202227 A1 | 7/2016 | Mathur et al. |
| 2016/0203657 A1 | 7/2016 | Bell et al. |
| 2016/0212939 A1 | 7/2016 | Ouchida et al. |
| 2016/0215994 A1 | 7/2016 | Mewes et al. |
| 2016/0232621 A1 | 8/2016 | Ethington et al. |
| 2016/0247075 A1 | 8/2016 | Mewes et al. |
| 2016/0247082 A1 | 8/2016 | Stehling |
| 2016/0260021 A1 | 9/2016 | Marek |
| 2016/0286720 A1 | 10/2016 | Heitmann et al. |
| 2016/0286721 A1 | 10/2016 | Heitmann et al. |
| 2016/0286722 A1 | 10/2016 | Heitmann et al. |
| 2016/0309656 A1 | 10/2016 | Wilken et al. |
| 2016/0327535 A1 | 11/2016 | Cotton et al. |
| 2016/0330906 A1 | 11/2016 | Acheson et al. |
| 2016/0338267 A1 | 11/2016 | Anderson et al. |
| 2016/0342915 A1 | 11/2016 | Humphrey |
| 2016/0345485 A1 | 12/2016 | Acheson et al. |
| 2016/0360697 A1 | 12/2016 | Diaz |
| 2017/0013773 A1 | 1/2017 | Kirk et al. |
| 2017/0031365 A1 | 2/2017 | Sugumaran et al. |
| 2017/0034997 A1 | 2/2017 | Mayerle |
| 2017/0049045 A1 | 2/2017 | Wilken et al. |
| 2017/0055433 A1 | 3/2017 | Jamison |
| 2017/0082442 A1 | 3/2017 | Anderson |
| 2017/0083024 A1 | 3/2017 | Reijersen |
| 2017/0086381 A1 | 3/2017 | Roell et al. |
| 2017/0089741 A1 | 3/2017 | Takahashi et al. |
| 2017/0089742 A1 | 3/2017 | Bruns et al. |
| 2017/0090068 A1 | 3/2017 | Xiang et al. |
| 2017/0105331 A1 | 4/2017 | Herlitzius et al. |
| 2017/0105335 A1 | 4/2017 | Xu et al. |
| 2017/0112049 A1 | 4/2017 | Weisberg et al. |
| 2017/0112061 A1 | 4/2017 | Meyer |
| 2017/0115862 A1 | 4/2017 | Stratton et al. |
| 2017/0118915 A1 | 5/2017 | Middelberg et al. |
| 2017/0124463 A1 | 5/2017 | Chen et al. |
| 2017/0127606 A1 | 5/2017 | Horton |
| 2017/0160916 A1 | 6/2017 | Baumgarten et al. |
| 2017/0161627 A1 | 6/2017 | Xu et al. |
| 2017/0185086 A1 | 6/2017 | Sauder et al. |
| 2017/0188515 A1 | 7/2017 | Baumgarten et al. |
| 2017/0192431 A1 | 7/2017 | Foster et al. |
| 2017/0208742 A1 | 7/2017 | Ingibergsson et al. |
| 2017/0213141 A1 | 7/2017 | Xu et al. |

(56) References Cited

U.S. PATENT DOCUMENTS

| | | |
|---|---|---|
| 2017/0215330 A1 | 8/2017 | Missotten et al. |
| 2017/0223947 A1 | 8/2017 | Gall et al. |
| 2017/0227969 A1 | 8/2017 | Murray et al. |
| 2017/0235471 A1 | 8/2017 | Scholer et al. |
| 2017/0245434 A1 | 8/2017 | Jung et al. |
| 2017/0251600 A1 | 9/2017 | Anderson et al. |
| 2017/0270446 A1 | 9/2017 | Starr et al. |
| 2017/0270616 A1 | 9/2017 | Basso |
| 2017/0316692 A1 | 11/2017 | Rusciolelli et al. |
| 2017/0318743 A1 | 11/2017 | Sauder et al. |
| 2017/0322550 A1 | 11/2017 | Yokoyama |
| 2017/0332551 A1 | 11/2017 | Todd et al. |
| 2017/0336787 A1 | 11/2017 | Pichlmaier et al. |
| 2017/0370765 A1 | 12/2017 | Meier et al. |
| 2018/0000011 A1 | 1/2018 | Schleusner et al. |
| 2018/0014452 A1 | 1/2018 | Starr |
| 2018/0022559 A1 | 1/2018 | Knutson |
| 2018/0024549 A1 | 1/2018 | Hurd |
| 2018/0035622 A1 | 2/2018 | Gresch et al. |
| 2018/0054955 A1 | 3/2018 | Oliver |
| 2018/0060975 A1 | 3/2018 | Hassanzadeh |
| 2018/0070534 A1 | 3/2018 | Mayerle |
| 2018/0077865 A1 | 3/2018 | Gallmeier |
| 2018/0084709 A1 | 3/2018 | Wieckhorst et al. |
| 2018/0084722 A1 | 3/2018 | Wieckhorst et al. |
| 2018/0092301 A1 | 4/2018 | Vandike et al. |
| 2018/0092302 A1 | 4/2018 | Vandike et al. |
| 2018/0108123 A1 | 4/2018 | Baurer et al. |
| 2018/0120133 A1 | 5/2018 | Blank et al. |
| 2018/0121821 A1 | 5/2018 | Parsons et al. |
| 2018/0124992 A1 | 5/2018 | Koch et al. |
| 2018/0128933 A1 | 5/2018 | Koch et al. |
| 2018/0129879 A1 | 5/2018 | Achtelik et al. |
| 2018/0132422 A1 | 5/2018 | Hassanzadeh et al. |
| 2018/0136664 A1 | 5/2018 | Tomita et al. |
| 2018/0146612 A1 | 5/2018 | Sauder et al. |
| 2018/0146624 A1 | 5/2018 | Chen et al. |
| 2018/0153084 A1 | 6/2018 | Calleija et al. |
| 2018/0177125 A1 | 6/2018 | Takahara et al. |
| 2018/0181893 A1 | 6/2018 | Basso |
| 2018/0196438 A1 | 7/2018 | Newlin et al. |
| 2018/0196441 A1 | 7/2018 | Muench et al. |
| 2018/0211156 A1 | 7/2018 | Guan et al. |
| 2018/0232674 A1 | 8/2018 | Bilde |
| 2018/0242523 A1 | 8/2018 | Kirchbeck et al. |
| 2018/0249641 A1 | 9/2018 | Lewis et al. |
| 2018/0257657 A1 | 9/2018 | Blank et al. |
| 2018/0271015 A1 | 9/2018 | Redden et al. |
| 2018/0279599 A1 | 10/2018 | Struve |
| 2018/0295771 A1 | 10/2018 | Peters |
| 2018/0310474 A1 | 11/2018 | Posselius et al. |
| 2018/0317381 A1 | 11/2018 | Bassett |
| 2018/0317385 A1 | 11/2018 | Wellensiek et al. |
| 2018/0325012 A1 | 11/2018 | Ferrari et al. |
| 2018/0325014 A1 | 11/2018 | Debbaut |
| 2018/0332767 A1 | 11/2018 | Muench et al. |
| 2018/0338422 A1 | 11/2018 | Brubaker |
| 2018/0340845 A1 | 11/2018 | Rhodes et al. |
| 2018/0359917 A1 | 12/2018 | Blank et al. |
| 2018/0359919 A1 | 12/2018 | Blank et al. |
| 2018/0364726 A1 | 12/2018 | Foster et al. |
| 2019/0021226 A1 | 1/2019 | Dima et al. |
| 2019/0025175 A1 | 1/2019 | Laugwitz |
| 2019/0041813 A1 | 2/2019 | Horn et al. |
| 2019/0050948 A1 | 2/2019 | Perry et al. |
| 2019/0057460 A1 | 2/2019 | Sakaguchi et al. |
| 2019/0066234 A1 | 2/2019 | Bedoya et al. |
| 2019/0069470 A1 | 3/2019 | Pfeiffer et al. |
| 2019/0075727 A1 | 3/2019 | Duke et al. |
| 2019/0085785 A1 | 3/2019 | Abolt |
| 2019/0090423 A1 | 3/2019 | Escher et al. |
| 2019/0098825 A1 | 4/2019 | Neitemeier et al. |
| 2019/0104722 A1 | 4/2019 | Slaughter et al. |
| 2019/0108413 A1 | 4/2019 | Chen et al. |
| 2019/0114847 A1 | 4/2019 | Wagner et al. |
| 2019/0124819 A1 | 5/2019 | Madsen et al. |
| 2019/0129430 A1 | 5/2019 | Madsen et al. |
| 2019/0136491 A1 | 5/2019 | Martin |
| 2019/0138962 A1 | 5/2019 | Ehlmann et al. |
| 2019/0147094 A1 | 5/2019 | Zhan et al. |
| 2019/0147249 A1 | 5/2019 | Kiepe et al. |
| 2019/0156255 A1 | 5/2019 | Carroll |
| 2019/0174667 A1 | 6/2019 | Gresch et al. |
| 2019/0183047 A1 | 6/2019 | Dybro et al. |
| 2019/0200522 A1 | 7/2019 | Hansen et al. |
| 2019/0230855 A1 | 8/2019 | Reed et al. |
| 2019/0239416 A1 | 8/2019 | Green et al. |
| 2019/0261550 A1 | 8/2019 | Damme et al. |
| 2019/0261559 A1 | 8/2019 | Heitmann et al. |
| 2019/0261560 A1 | 8/2019 | Jelenkovic |
| 2019/0313570 A1 | 10/2019 | Owechko |
| 2019/0327889 A1 | 10/2019 | Borgstadt |
| 2019/0327892 A1 | 10/2019 | Fries et al. |
| 2019/0335662 A1 | 11/2019 | Good et al. |
| 2019/0335674 A1 | 11/2019 | Basso |
| 2019/0343035 A1 | 11/2019 | Smith et al. |
| 2019/0343043 A1 | 11/2019 | Bormann et al. |
| 2019/0343044 A1 | 11/2019 | Bormann et al. |
| 2019/0343048 A1 | 11/2019 | Farley et al. |
| 2019/0351765 A1 | 11/2019 | Rabusic |
| 2019/0354081 A1 | 11/2019 | Blank et al. |
| 2019/0364733 A1 | 12/2019 | Laugen et al. |
| 2019/0364734 A1 | 12/2019 | Kriebel et al. |
| 2020/0000006 A1 | 1/2020 | McDonald et al. |
| 2020/0008351 A1 | 1/2020 | Zielke et al. |
| 2020/0015416 A1 | 1/2020 | Barther et al. |
| 2020/0019159 A1 | 1/2020 | Kocer et al. |
| 2020/0024102 A1 | 1/2020 | Brill et al. |
| 2020/0029488 A1 | 1/2020 | Bertucci et al. |
| 2020/0034759 A1 | 1/2020 | Dumstorff et al. |
| 2020/0037491 A1 | 2/2020 | Schoeny et al. |
| 2020/0053961 A1 | 2/2020 | Dix et al. |
| 2020/0064144 A1 | 2/2020 | Tomita et al. |
| 2020/0064863 A1 | 2/2020 | Tomita et al. |
| 2020/0074023 A1 | 3/2020 | Nizami et al. |
| 2020/0084963 A1 | 3/2020 | Gururajan et al. |
| 2020/0084966 A1 | 3/2020 | Corban et al. |
| 2020/0090094 A1 | 3/2020 | Blank |
| 2020/0097851 A1 | 3/2020 | Alvarez et al. |
| 2020/0113142 A1 | 4/2020 | Coleman et al. |
| 2020/0125822 A1 | 4/2020 | Yang et al. |
| 2020/0128732 A1 | 4/2020 | Chaney |
| 2020/0128733 A1 | 4/2020 | Vandike et al. |
| 2020/0128734 A1 | 4/2020 | Brammeler et al. |
| 2020/0128735 A1 | 4/2020 | Bonefas et al. |
| 2020/0128737 A1 | 4/2020 | Anderson et al. |
| 2020/0128738 A1 | 4/2020 | Suleman et al. |
| 2020/0128740 A1 | 4/2020 | Suleman |
| 2020/0133262 A1 | 4/2020 | Suleman et al. |
| 2020/0141784 A1 | 5/2020 | Lange et al. |
| 2020/0146203 A1 | 5/2020 | Deng |
| 2020/0150631 A1 | 5/2020 | Frieberg et al. |
| 2020/0154639 A1 | 5/2020 | Takahara et al. |
| 2020/0163277 A1 | 5/2020 | Cooksey et al. |
| 2020/0183406 A1 | 6/2020 | Borgstadt |
| 2020/0187409 A1 | 6/2020 | Meyer zu Helligen |
| 2020/0196526 A1 | 6/2020 | Koch et al. |
| 2020/0202596 A1 | 6/2020 | Kitahara et al. |
| 2020/0221632 A1 | 7/2020 | Strnad et al. |
| 2020/0221635 A1 | 7/2020 | Hendrickson et al. |
| 2020/0221636 A1 | 7/2020 | Boydens et al. |
| 2020/0265527 A1 | 8/2020 | Rose et al. |
| 2020/0278680 A1 | 9/2020 | Schultz et al. |
| 2020/0317114 A1 | 10/2020 | Hoff |
| 2020/0319632 A1 | 10/2020 | Desai et al. |
| 2020/0319655 A1 | 10/2020 | Desai et al. |
| 2020/0323133 A1 | 10/2020 | Anderson et al. |
| 2020/0323134 A1 | 10/2020 | Darr et al. |
| 2020/0326674 A1 | 10/2020 | Palla et al. |
| 2020/0326727 A1 | 10/2020 | Palla et al. |
| 2020/0333278 A1 | 10/2020 | Locken et al. |
| 2020/0337232 A1 | 10/2020 | Blank et al. |
| 2020/0352099 A1 | 11/2020 | Meier et al. |
| 2020/0359547 A1 | 11/2020 | Sakaguchi et al. |

(56) References Cited

U.S. PATENT DOCUMENTS

| | | | |
|---|---|---|---|
| 2020/0359549 A1 | 11/2020 | Sakaguchi et al. | |
| 2020/0363256 A1 | 11/2020 | Meier et al. | |
| 2020/0375083 A1 | 12/2020 | Anderson et al. | |
| 2020/0375084 A1 | 12/2020 | Sakaguchi et al. | |
| 2020/0378088 A1 | 12/2020 | Anderson | |
| 2020/0404842 A1 | 12/2020 | Dugas et al. | |
| 2021/0015041 A1 | 1/2021 | Bormann et al. | |
| 2021/0129853 A1 | 5/2021 | Appleton et al. | |
| 2021/0176916 A1 | 6/2021 | Sidon et al. | |
| 2021/0176918 A1 | 6/2021 | Franzen et al. | |
| 2021/0289687 A1 | 9/2021 | Heinold et al. | |
| 2021/0321567 A1 | 10/2021 | Sidon et al. | |
| 2022/0110255 A1* | 4/2022 | Vandike | A01B 79/005 |
| 2022/0110258 A1* | 4/2022 | Vandike | G05D 1/0278 |
| 2022/0113734 A1* | 4/2022 | Vandike | G01C 21/3889 |

FOREIGN PATENT DOCUMENTS

| | | |
|---|---|---|
| BR | PI0502658 A | 2/2007 |
| BR | PI0802384 A2 | 3/2010 |
| BR | PI1100258 A2 | 3/2014 |
| BR | 102014007178 A2 | 8/2016 |
| CA | 1165300 A | 4/1984 |
| CA | 2283767 A1 | 3/2001 |
| CA | 2330979 A1 | 8/2001 |
| CA | 2629555 A1 | 11/2009 |
| CA | 135611 S | 5/2011 |
| CN | 2451633 Y | 10/2001 |
| CN | 101236188 A | 8/2008 |
| CN | 100416590 C | 9/2008 |
| CN | 101303338 A | 11/2008 |
| CN | 101363833 A | 2/2009 |
| CN | 201218789 Y | 4/2009 |
| CN | 101839906 A | 9/2010 |
| CN | 101929166 A | 12/2010 |
| CN | 102080373 A | 6/2011 |
| CN | 102138383 A | 8/2011 |
| CN | 102277867 B | 12/2011 |
| CN | 202110103 U | 1/2012 |
| CN | 202119772 U | 1/2012 |
| CN | 202340435 U | 7/2012 |
| CN | 103088807 A | 5/2013 |
| CN | 103181263 A | 7/2013 |
| CN | 203053961 U | 7/2013 |
| CN | 203055121 U | 7/2013 |
| CN | 203206739 U | 9/2013 |
| CN | 203275401 U | 11/2013 |
| CN | 203613525 U | 5/2014 |
| CN | 203658201 U | 6/2014 |
| CN | 103954738 A | 7/2014 |
| CN | 203741803 U | 7/2014 |
| CN | 204000818 U | 12/2014 |
| CN | 204435344 U | 7/2015 |
| CN | 204475304 U | 7/2015 |
| CN | 105205248 A | 12/2015 |
| CN | 204989174 U | 1/2016 |
| CN | 105432228 A | 3/2016 |
| CN | 105741180 A | 7/2016 |
| CN | 106053330 A | 10/2016 |
| CN | 106198877 A | 12/2016 |
| CN | 106198879 A | 12/2016 |
| CN | 106226470 A | 12/2016 |
| CN | 106248873 A | 12/2016 |
| CN | 106290800 A | 1/2017 |
| CN | 106327349 A | 1/2017 |
| CN | 106644663 A | 5/2017 |
| CN | 206330815 U | 7/2017 |
| CN | 206515118 U | 9/2017 |
| CN | 206515119 U | 9/2017 |
| CN | 206616118 U | 11/2017 |
| CN | 206696107 | 12/2017 |
| CN | 206696107 U | 12/2017 |
| CN | 107576674 | 1/2018 |
| CN | 107576674 A | 1/2018 |
| CN | 206906093 U | 1/2018 |
| CN | 206941558 | 1/2018 |
| CN | 206941558 U | 1/2018 |
| CN | 107736088 A | 2/2018 |
| CN | 107795095 A | 3/2018 |
| CN | 207079558 | 3/2018 |
| CN | 107941286 A | 4/2018 |
| CN | 107957408 A | 4/2018 |
| CN | 108009542 A | 5/2018 |
| CN | 108304796 A | 7/2018 |
| CN | 207567744 U | 7/2018 |
| CN | 108614089 A | 10/2018 |
| CN | 208013131 U | 10/2018 |
| CN | 108881825 A | 11/2018 |
| CN | 208047351 U | 11/2018 |
| CN | 109357804 A | 2/2019 |
| CN | 109485353 A | 3/2019 |
| CN | 109633127 A | 4/2019 |
| CN | 109763476 A | 5/2019 |
| CN | 109961024 A | 7/2019 |
| CN | 110262287 A | 9/2019 |
| CN | 110720302 A | 1/2020 |
| CN | 111201879 A | 5/2020 |
| CN | 210585958 U | 5/2020 |
| CN | 111406505 A | 7/2020 |
| CS | 247426 B1 | 12/1986 |
| CS | 248318 B1 | 2/1987 |
| CZ | 17266 U1 | 2/2007 |
| CZ | 20252 U1 | 11/2009 |
| DE | 441597 C | 3/1927 |
| DE | 504035 C | 7/1930 |
| DE | 2354828 A1 | 5/1975 |
| DE | 152380 A1 | 11/1981 |
| DE | 3728669 A1 | 3/1989 |
| DE | 4431824 C1 | 5/1996 |
| DE | 19509496 A1 | 9/1996 |
| DE | 19528663 A1 | 2/1997 |
| DE | 19718455 A1 | 11/1997 |
| DE | 19705842 A1 | 8/1998 |
| DE | 19828355 A1 | 1/2000 |
| DE | 10050224 A1 | 4/2002 |
| DE | 10120173 A1 | 10/2002 |
| DE | 202004015141 U1 | 12/2004 |
| DE | 102005000770 B3 | 7/2006 |
| DE | 102005000771 A1 | 8/2006 |
| DE | 102008021785 A1 | 11/2009 |
| DE | 102009041646 A1 | 3/2011 |
| DE | 102010004648 A1 | 7/2011 |
| DE | 102010038661 A1 | 2/2012 |
| DE | 102011005400 A1 | 9/2012 |
| DE | 202012103730 U1 | 10/2012 |
| DE | 102012211001 A1 | 1/2014 |
| DE | 102012220109 | 5/2014 |
| DE | 102012223768 | 6/2014 |
| DE | 102013212151 A1 | 12/2014 |
| DE | 102013019098 B3 | 1/2015 |
| DE | 102014108449 A1 | 2/2015 |
| DE | 2014201203 A1 | 7/2015 |
| DE | 102014208068 A1 | 10/2015 |
| DE | 102015006398 B3 | 5/2016 |
| DE | 102015109799 A1 | 12/2016 |
| DE | 112015002194 T5 | 1/2017 |
| DE | 102019206734 A1 | 11/2020 |
| DE | 102019114872 A1 | 12/2020 |
| EP | 0070219 B1 | 10/1984 |
| EP | 0355049 A2 | 2/1990 |
| EP | 845198 B2 | 6/1998 |
| EP | 0532146 B1 | 8/1998 |
| EP | 1444879 A1 | 8/2004 |
| EP | 1219159 B1 | 6/2005 |
| EP | 1219153 B1 | 2/2006 |
| EP | 1692928 A2 | 8/2006 |
| EP | 1574122 B1 | 2/2008 |
| EP | 1943877 A2 | 7/2008 |
| EP | 1598586 B1 | 9/2009 |
| EP | 1731983 B1 | 9/2009 |
| EP | 2146307 A2 | 1/2010 |
| EP | 2186389 A1 | 5/2010 |
| EP | 2267566 A2 | 12/2010 |
| EP | 3491192 A2 | 12/2010 |

(56) References Cited

FOREIGN PATENT DOCUMENTS

| | | |
|---|---|---|
| EP | 2057884 B1 | 1/2011 |
| EP | 2146307 B1 | 5/2012 |
| EP | 2446732 A1 | 5/2012 |
| EP | 2524586 A2 | 11/2012 |
| EP | 2529610 A1 | 12/2012 |
| EP | 102011052688 A1 | 2/2013 |
| EP | 2243353 B1 | 3/2013 |
| EP | 2174537 B1 | 5/2013 |
| EP | 2592919 A1 | 5/2013 |
| EP | 1674324 B2 | 5/2014 |
| EP | 2759829 A1 | 7/2014 |
| EP | 2764764 B1 | 8/2014 |
| EP | 2267566 A3 | 12/2014 |
| EP | 2191439 B1 | 3/2015 |
| EP | 2586286 B1 | 3/2015 |
| EP | 2592919 B1 | 9/2015 |
| EP | 2921042 A1 | 9/2015 |
| EP | 2944725 A1 | 11/2015 |
| EP | 2510777 B1 | 3/2016 |
| EP | 3000302 A1 | 3/2016 |
| EP | 2868806 B1 | 7/2016 |
| EP | 3085221 A1 | 10/2016 |
| EP | 3095310 A1 | 11/2016 |
| EP | 3097759 A1 | 11/2016 |
| EP | 2452551 B1 | 5/2017 |
| EP | 3175691 A1 | 6/2017 |
| EP | 3195719 A1 | 7/2017 |
| EP | 3195720 A1 | 7/2017 |
| EP | 3259976 A1 | 12/2017 |
| EP | 3262934 A1 | 1/2018 |
| EP | 3491192 A1 | 1/2018 |
| EP | 3287007 A1 | 2/2018 |
| EP | 3298876 A1 | 3/2018 |
| EP | 3300579 A1 | 4/2018 |
| EP | 3315005 A1 | 5/2018 |
| EP | 3316208 A1 | 5/2018 |
| EP | 2829171 B1 | 6/2018 |
| EP | 2508057 | 7/2018 |
| EP | 2508057 B1 | 7/2018 |
| EP | 3378298 A1 | 9/2018 |
| EP | 3378299 A1 | 9/2018 |
| EP | 102017204511 A1 | 9/2018 |
| EP | 2997805 A1 | 10/2018 |
| EP | 3384754 A1 | 10/2018 |
| EP | 3289853 B1 | 3/2019 |
| EP | 3456167 A1 | 3/2019 |
| EP | 3466239 A1 | 4/2019 |
| EP | 3469878 A1 | 4/2019 |
| EP | 3289852 B1 | 6/2019 |
| EP | 3494770 A1 | 6/2019 |
| EP | 3498074 A1 | 6/2019 |
| EP | 3000302 B1 | 8/2019 |
| EP | 3533314 A1 | 9/2019 |
| EP | 3569049 A1 | 11/2019 |
| EP | 3000307 B1 | 12/2019 |
| EP | 3586592 A2 | 1/2020 |
| EP | 3593613 A1 | 1/2020 |
| EP | 3593620 A1 | 1/2020 |
| EP | 3613272 A1 | 2/2020 |
| EP | 3243374 B1 | 3/2020 |
| EP | 3626038 A1 | 3/2020 |
| EP | 3259976 B1 | 4/2020 |
| EP | 3635647 A1 | 4/2020 |
| EP | 3378298 B1 | 5/2020 |
| EP | 3646699 A1 | 5/2020 |
| EP | 3662741 A1 | 6/2020 |
| EP | 3685648 A1 | 7/2020 |
| EP | 2995191 B2 | 10/2020 |
| ES | 2116215 A1 | 7/1998 |
| ES | 2311322 A1 | 2/2009 |
| FI | 5533 A | 11/1913 |
| FR | 1451480 A | 1/1966 |
| FR | 2817344 A1 | 5/2002 |
| FR | 2901291 A | 11/2007 |
| FR | 2901291 A1 | 11/2007 |
| GB | 901081 A | 7/1962 |
| GB | 201519517 A1 | 5/2017 |
| IN | 01632DE2014 A | 8/2016 |
| IN | 201641027017 A | 10/2016 |
| IN | 202041039250 A | 9/2020 |
| JP | 7079681 A | 11/1982 |
| JP | S60253617 A | 12/1985 |
| JP | S63308110 A | 12/1988 |
| JP | H02196960 A | 8/1990 |
| JP | H02215311 A | 8/1990 |
| JP | H0779681 A | 3/1995 |
| JP | H1066436 A | 3/1998 |
| JP | H10191762 A | 7/1998 |
| JP | 2000352044 A | 12/2000 |
| JP | 2001057809 A | 3/2001 |
| JP | 2002186348 A | 7/2002 |
| JP | 2005227233 A | 8/2005 |
| JP | 2006166871 A | 6/2006 |
| JP | 2011205967 A | 10/2011 |
| JP | 2015070812 A | 4/2015 |
| JP | 2015151826 A | 8/2015 |
| JP | 2015219651 A | 12/2015 |
| JP | 2016071726 A | 5/2016 |
| JP | 2016160808 A | 9/2016 |
| JP | 6087258 B2 | 3/2017 |
| JP | 2017136035 A | 8/2017 |
| JP | 2017137729 A | 8/2017 |
| JP | 2017195804 A | 11/2017 |
| JP | 2018068284 A | 5/2018 |
| JP | 2018102154 A | 7/2018 |
| JP | 2018151388 A | 9/2018 |
| JP | 2019004796 A | 1/2019 |
| JP | 2019129744 A | 8/2019 |
| JP | 2019146506 A | 9/2019 |
| JP | 2019216744 A | 12/2019 |
| JP | 2020018255 A | 2/2020 |
| JP | 2020031607 A | 3/2020 |
| JP | 2020113062 A | 7/2020 |
| JP | 2020127405 A | 8/2020 |
| KR | 100974892 | 8/2010 |
| KR | 100974892 B1 | 8/2010 |
| KR | 20110018582 A | 2/2011 |
| KR | 101067576 B | 9/2011 |
| KR | 101067576 B1 | 9/2011 |
| KR | 101134075 B1 | 4/2012 |
| KR | 101447197 B1 | 10/2014 |
| KR | 101653750 | 9/2016 |
| KR | 20170041377 A | 4/2017 |
| KR | 200485051 Y | 11/2017 |
| KR | 200485051 Y1 | 11/2017 |
| KR | 101873657 B | 8/2018 |
| MX | GT06000012 A | 1/2008 |
| PL | 178299 B1 | 4/2000 |
| RO | 130713 | 11/2015 |
| RU | 1791767 C | 1/1993 |
| RU | 2005102554 A | 7/2006 |
| RU | 2421744 C | 6/2011 |
| RU | 2421744 C1 | 6/2011 |
| RU | 2447640 C1 | 4/2012 |
| RU | 2502047 C | 12/2013 |
| RU | 2502047 C1 | 12/2013 |
| RU | 164128 | 8/2016 |
| RU | 2017114139 A | 10/2018 |
| RU | 2017114139 A3 | 5/2019 |
| SU | 834514 A1 | 5/1981 |
| SU | 887717 A1 | 12/1981 |
| SU | 1052940 A1 | 11/1983 |
| SU | 1134669 A1 | 1/1985 |
| SU | 1526588 A1 | 12/1989 |
| SU | 1540053 A1 | 1/1991 |
| SU | 1761864 A1 | 9/1992 |
| WO | 1986005353 A1 | 9/1986 |
| WO | 2001052160 A1 | 7/2001 |
| WO | 2002015673 A1 | 2/2002 |
| WO | 2003005803 A1 | 1/2003 |
| WO | 2007050192 A2 | 5/2007 |
| WO | 2009156542 A1 | 12/2009 |
| WO | 2010003421 A1 | 1/2010 |
| WO | 2011104085 A1 | 9/2011 |

(56) References Cited

FOREIGN PATENT DOCUMENTS

| | | |
|---|---|---|
| WO | 2012041621 A1 | 4/2012 |
| WO | 2012110508 A1 | 8/2012 |
| WO | 2012110544 A1 | 8/2012 |
| WO | 2013063106 A2 | 5/2013 |
| WO | 2013079247 A1 | 6/2013 |
| WO | 2013086351 A1 | 6/2013 |
| WO | 2013087275 A1 | 6/2013 |
| WO | 2014046685 A1 | 3/2014 |
| WO | 2014093814 A1 | 6/2014 |
| WO | 2014195302 A1 | 12/2014 |
| WO | 2015038751 A1 | 3/2015 |
| WO | 2015153809 A1 | 10/2015 |
| WO | 16020595 A1 | 2/2016 |
| WO | 2016020595 A1 | 2/2016 |
| WO | 2016118686 A1 | 7/2016 |
| WO | 2017008161 A1 | 1/2017 |
| WO | 2017060168 A1 | 4/2017 |
| WO | 2017077113 A1 | 5/2017 |
| WO | 2017096489 A1 | 6/2017 |
| WO | 2017099570 A1 | 6/2017 |
| WO | 2017116913 A1 | 7/2017 |
| WO | 2017170507 A1 | 10/2017 |
| WO | 2017205406 A1 | 11/2017 |
| WO | 2017205410 A1 | 11/2017 |
| WO | 2018043336 A1 | 3/2018 |
| WO | 2018073060 A1 | 4/2018 |
| WO | 2018081759 A1 | 5/2018 |
| WO | 2018112615 | 6/2018 |
| WO | 2018116772 A1 | 6/2018 |
| WO | 2018142768 A1 | 8/2018 |
| WO | 2018200870 A1 | 11/2018 |
| WO | 2018206587 A1 | 11/2018 |
| WO | 2018220159 A1 | 12/2018 |
| WO | 2018226139 A1 | 12/2018 |
| WO | 2018235486 A1 | 12/2018 |
| WO | 2018235942 A1 | 12/2018 |
| WO | WO18235486 A1 | 12/2018 |
| WO | 2019034213 A1 | 2/2019 |
| WO | 2019079205 A1 | 4/2019 |
| WO | 2019081349 A1 | 5/2019 |
| WO | 2019091535 A1 | 5/2019 |
| WO | 2019109191 A1 | 6/2019 |
| WO | 2019124174 A1 | 6/2019 |
| WO | 2019124217 A1 | 6/2019 |
| WO | 2019124225 A1 | 6/2019 |
| WO | 2019124273 A1 | 6/2019 |
| WO | 2019129333 A1 | 7/2019 |
| WO | 2019129334 A1 | 7/2019 |
| WO | 2019129335 A1 | 7/2019 |
| WO | 2019215185 A1 | 11/2019 |
| WO | 2019230358 A1 | 12/2019 |
| WO | 2020026578 A1 | 2/2020 |
| WO | 2020026650 A1 | 2/2020 |
| WO | 2020026651 A1 | 2/2020 |
| WO | 2020031473 A1 | 2/2020 |
| WO | 2020038810 A1 | 2/2020 |
| WO | 2020039312 A1 | 2/2020 |
| WO | 2020039671 A1 | 2/2020 |
| WO | 2020044726 A1 | 3/2020 |
| WO | 2020082182 A1 | 4/2020 |
| WO | 2020100810 A1 | 5/2020 |
| WO | 2020110920 A1 | 6/2020 |
| WO | 2020195007 A1 | 10/2020 |
| WO | 2020206941 A1 | 10/2020 |
| WO | 2020206942 A1 | 10/2020 |
| WO | 2020210607 A1 | 10/2020 |
| WO | 2020221981 A1 | 11/2020 |
| WO | 2021262500 A1 | 12/2021 |

OTHER PUBLICATIONS

Notice of Allowance for U.S. Appl. No. 16/432,557 dated Mar. 22, 2021, 9 pages.
Zhao, L., Yang, J., Li, P. and Zhang, L., 2014. Characteristics analysis and classification of crop harvest patterns by exploiting high-frequency multipolarization SAR data. IEEE Journal of Selected Topics in Applied Earth Observations and Remote Sensing, 7(9), pp. 3773-3783.
Feng-jie, X., Er-da, W. and Feng-yuan, X., Crop area yield risk evaluation and premium rates calculation—Based on nonparametric kernel density estimation. In 2009 International Conference on Management Science and Engineering, 7 pages.
Liu, R. and Bai, X., 2014, May. Random fuzzy production and distribution plan of agricultural products and its PSO algorithm. In 2014 IEEE International Conference on Progress in Informatics and Computing (pp. 32-36). IEEE.
Notice of Allowance for U.S. Appl. No. 16/171,978 dated Mar. 31, 2021, 6 pages.
Application and Drawings for U.S. Appl. No. 17/067,383, filed Oct. 9, 2020, 61 pages.
Application and Drawings for U.S. Appl. No. 16/175,993, filed Oct. 31, 2018, 28 pages.
Application and Drawings for U.S. Appl. No. 16/380,623, filed Apr. 10, 2019, 36 pages.
Application and Drawings for U.S. Appl. No. 16/783,511, filed Feb. 6, 2020, 55 pages.
"Automated Weed Detection With Drones" dated May 25, 2017, retrieved at: <<https://www.precisionhawk.com/blog/media/topic/automated-weed-identification-with-drones>>, retrieved on Jan. 21, 2020, 4 pages.
F. Forcella, "Estimating the Timing of Weed Emergence", Site-Specific Management Guidelines, retrieved at: <<http://www.ipni.net/publication/ssmg.nsf/0/D26EC9A906F9B8C9852579E500773936/$FILE/SSMG-20.pdf>>, retrieved on Jan. 21, 2020, 4 pages.
Chauhan et al., "Emerging Challenges and Opportunities for Education and Research in Weed Science", frontiers in Plant Science. Published online Sep. 5, 2017, 22 pages.
Apan, A., Wells ,N., Reardon-Smith, K, Richardson, L, McDougall, K, and Basnet, B.B., 2008. Predictive mapping of blackberry in the Condamine Catchment using logistic regression and spatial analysis. In Proceedings of the 2008 Queensland Spatial Conference: Global Warning: What's Happening in Paradise. Spatial Sciences Institute, 11 pages.
Jarnevich, C.S., Holcombe, T.R., Barnett, D.T., Stohlgren, T.J. and Kartesz, J.T., 2010. Forecasting weed distributions using climate data: a GIS early warning tool. Invasive Plant Science and Management. 3(4), pp. 365-375.
Sa et al., "WeedMap: A Large-Scale Semantic Weed Mapping Framework Using Aerial Multispectral Imaging and Deep Neural Network for Precision Farming", Sep. 6, 2018, 25 pages.
Pflanz et al., "Weed Mapping with UAS Imagery and a Bag of Visual Words Based Image Classifier", Published Sep. 24, 2018, 28 pages.
Provisional Application and Drawings for U.S. Appl. No. 62/928,964, filed Oct. 31, 2019, 14 pages.
Application and Drawings for U.S. Appl. No. 16/783,475, filed Feb. 6, 2020, 55 pages.
U.S. Appl. No. 17/067,483 Application and Drawings as filed Oct. 9, 2020, 63 pages.
U.S. Appl. No. 17/066,442 Application and Drawings as filed Oct. 8, 2020, 65 pages.
U.S. Appl. No. 16/380,550, filed Apr. 10, 2019, Application and Drawings, 47 pages.
U.S. Appl. No. 17/066,999 Application and Drawings as filed Oct. 9, 2020, 67 pages.
U.S. Appl. No. 17/066,444 Application and Drawings as filed Oct. 8, 2020, 102 pages.
Extended Search Report for European Patent Application No. 20167930.5 dated Sep. 15, 2020, 8 pages.
Extended Search Report for European Patent Application No. 19205901.2 dated Mar. 17, 2020, 6 pages.
Notice of Allowance for U.S. Appl. No. 16/171,978, dated Dec. 15, 2020, 21 pages.
Zhigen et al., "Research of the Combine Harvester Load Feedback Control System Using Multi-Signal Fusion Method and Fuzzy Algorithm," 2010, Publisher: IEEE, 5 pages.

(56) References Cited

OTHER PUBLICATIONS

Dan et al., "On-the-go Throughput Prediction in a Combine Harvester Using Sensor Fusion," 2017, Publisher: IEEE, 6 pages.
Fernandez-Quintanilla et al., "Is the current state of the art of weed monitoring sutible for site-specific weed management in arable crops?", First Published May 1, 2018, 4 pages.
Dionysis Bochtis et al. "Field Operations Planning for Agricultural Vehicles: A Hierarchical Modeling Framework." Agricultural Engineering International: the CIGR Ejournal. Manuscript PM 06 021. vol. IX. Feb. 2007, pp. 1-11.
U.S. Appl. No. 16/432,557, filed Jun. 5, 2019, 61 pages.
European Search Report issued in counterpart European Patent Application No. 19205142.3 dated Feb. 28, 2020 (6 pages).
Mei-Ju et al., "Two paradigms in cellular Internet-of-Things access for energy-harvesting machine-to-machine devices: push-based versus pull-based," 2016, vol. 6, 9 pages.
Yi et al., "An Efficient MAC Protocol With Adaptive Energy Harvesting for Machine-to-Machine Networks," 2015, vol. 3, Publisher: IEEE, 10 pages.
European Search Report issued in European Patent Application No. 19203883.4 dated Mar. 23, 2020 (10 pages).
Notice of Allowance for U.S. Appl. No. 16/171,978 dated Oct. 28, 2020, 5 pages.
Notice of Allowance for U.S. Appl. No. 16/171,978, dated Aug. 7, 2020, 9 pages.
K.R. Manjunath et al., "Developing Spectral Library of Major Plant Species of Western Himalayas Using Ground Observations", J. Indian Soc Remote Sen (Mar. 2014) 42(a):201-216, 17 pages.
U.S. Appl. No. 16/380,564 Application and Drawings as filed Apr. 10, 2019, 55 pages.
S. Veenadhari et al., "Machine Learning Approach For Forecasting Crop Yield Based on Climatic Parameters", 2014 International Conference on Computer Communication and Informatics (ICCCI-2014) Jan. 3-6, 2014, Coimbatore, India, 5 pages.
Non-Final Office Action for U.S. Appl. No. 16/380,531 dated Oct. 21, 2020, 10 pages.
U.S. Appl. No. 16/380,531 Application and Drawings as filed Apr. 10, 2019, 46 pages.
Martin et al. Breakage Susceptibilty and Hardness of Corn Kernels of Various Sizes and Shapes, vol. 3(): May 1087, 10 pages. https://pdfs.semanticscholar.org/e579/1b5363b6a78efd44adfb97755a0cdd14f7ca.pdf.
Hoff, "Combine Adjustments" (https://smallfarmersjournal.com/combine-adjustments/), Mar. 1943, 9 pages.
Optimizing Crop Profit Across Multiple Grain Attributes and Stover, Electronic Publication Date May 26, 2009, 17 pages.
Unglesbee, Soybean Pod Shatter—Bad Enough to Scout Before Harvest—DTN, Oct. 17, 2018, 11 pages. Susceptibility to shatter (https://agfax.com/2018/10/17/soybean-pod-shatter-bad-enough-to-scout-before-harvest-dtn/).
GIS Maps for Agricultural, accessed on May 10, 2022, 7 pages. https://www.satimagingcorp.com/services/geographic-information-systems/gis-maps-agriculture-mapping.
https://wingtra.com/drone-mapping-applications/use-of-drones-in-agriculture, accessed on May 10, 2022, 19 pages.
Energy Requirement Model for a Combine Harvester: Part 1: Development of Component Models, Published online Dec. 22, 2004, 17 pages.
Energy Requirement Model for a Combine Harvester, Part 2: Integration of Component Models, Published online Jan. 18, 2005, 11 pages.
Pioneer on reducing soybean harvest losses including combine adjustments (last accessed Jul. 23, 2020) (https://www.pioneer.com/us/agronomy/reducing_harvest_losses_in_soybeans.html), 5 pages.
Martin et al., "Breakage Susceptibility and Harness of Corn Kernels of Various Sizes and Shapes", May 1987, 10 pages.
Jones et al., "Brief history of agricultural systems modeling" Jun. 21, 2016, 15 pages.
Dan Anderson, "Brief history of agricultural systems modeling" 1 pages. Aug. 13, 2019.
A.Y. Şeflek, "Determining the Physico-Mechanical Characteristics of Maize Stalks Fordesigning Harvester", The Journal of Animal & Plant Sciences, 27(3): 2017, p. 855-860 ISSN: 1018-7081, Jun. 1, 2017.
Carmody, Paul, "Windrowing and harvesting", 8 pages Date: Feb. 3, 2010.
Dabney, et al., "Forage Harvest Representation in RUSLE2", Published Nov. 15, 2013, 17 pages.
John Deere S-Series Combines S760, S770, S780, S790 Brochure, 44 pages, Nov. 15, 2017.
Sekhon et al., "Stalk Bending Strength is Strongly Assoicated with Maize Stalk Lodging Incidence Across Multiple Environments", Jun. 20, 2019, 23 pages.
Thomison et al. "Abnormal Corn Ears", Apr. 28, 2015, 1 page.
Anderson, "Adjust your Combine to Reduce Damage to High Moisture Corn", Aug. 13, 2019, 11 pages.
Sumner et al., "Reducing Aflatoxin in Corn During Harvest and Storage", Reviewed by John Worley, Apr. 2017, 6 pages.
Sick, "Better understanding corn hybrid characteristics and properties can impact your seed decisions", 8 pages, Sep. 21, 2018.
TraCI/Change Vehicle State—SUMO Documentation, 10 pages, Retrieved Dec. 11, 2020.
Arnold, et al., Chapter 8. "Plant Growth Component", Jul. 1995, 41 pages.
Humburg, Chapter: 37 "Combine Adjustments to Reduce Harvest Losses", 2019, South Dakota Board of Regents, 8 pages.
Hoff, "Combine Adjustments", Cornell Extension Bulletin 591, Mar. 1943, 10 pages.
University of Wisconsin, Com Agronomy, Originally written Feb. 1, 2006 | Last updated Oct. 18, 2018, 2 pages.
University of Nebraska-Lincoln, "Combine Adjustments for Downed Corn—Crop Watch", Oct. 27, 2017, 5 pages.
"Combine Cleaning: Quick Guide To Removing Resistant Weed Seeds (Among Other Things)", Nov. 2006, 5 pages.
Dekalb, "Com Drydown Rates", 7 pages, Aug. 4, 2020.
Mahmoud et al. Iowa State University, "Corn Ear Orientation Effects on Mechanical Damage and Forces on Concave", 1975, 6 pages.
Sindelar et al., Kansas State University, "Corn Growth & Development" Jul. 17, 2017, 9 pages.
Pannar, "Manage the Growth Stages of the Maize Plant With Pannar", Nov. 14, 2016, 7 pages.
He et al., "Crop residue harvest impacts wind erodibility and simulated soil loss in the Central Great Plains", Sep. 27, 2017, 14 pages.
Blanken, "Designing a Living Snow Fence for Snow Drift Control", Jan. 17, 2018, 9 pages.
Jean, "Drones give aerial boost to ag producers", Mar. 21, 2019, 4 pages.
Zhao et al., "Dynamics modeling for sugarcane sucrose estimation using time series satellite imagery", Jul. 27, 2017, 11 pages.
Brady, "Effects of Cropland Conservation Practices on Fish and Wildlife Habitat", Sep. 1, 2007, 15 pages.
Jasa, et al., "Equipment Adjustments for Harvesting Soybeans at 13%-15% Moisture", Sep. 15, 2017, 2 pages.
Bendig et al., "Estimating Biomass of Barley Using Crop Surface Models (CSMs) Derived from UAV-Based RGB Imaging", Oct. 21, 2014, 18 pages.
Robertson, et al., "Maize Stalk Lodging: Morphological Determinants of Stalk Strength", Mar. 3, 2017, 10 pages.
MacGowan et al. Purdue University, Corn and Soybean Crop Deprediation by Wildlife, Jun. 2006, 14 pages.
Martinez-Feria et al., Iowa State University, "Corn Grain Dry Down in Field From Maturity to Harvest", Sep. 20, 2017, 3 pages.
Wrona, "Precision Agriculture's Value" Cotton Physiology Today, vol. 9, No. 2, 1998, 8 pages.
Zhang et al., "Design of an Optical Weed Sensor Using Plant Spectral Characteristics" Sep. 2000, 12 pages.
Hunt, et al., "What Weeds Can Be Remotely Sensed?", 5 pages, May 2016.
Pepper, "Does An Adaptive Gearbox Really Learn How You Drive?", Oct. 30, 2019, 8 pages.

(56) References Cited

OTHER PUBLICATIONS

Eggerl, "Optimization of Combine Processes Using Expert Knowledge and Methods of Artificial Intelligence", Jul. 10, 1982, 143 pages.
Sheely et al., "Image-Based, Variable Rate Plant Growth Regulator Application in Cotton at Sheely Farms in California", Jan. 6-10, 2003 Beltwide Cotton Conferences, Nashville, TN, 17 pages.
Kovacs et al., "Physical characteristics and mechanical behaviour of maize stalks for machine development", Apr. 23, 2019, 1-pages.
Anonymously, "Optimizing Crop Profit Across Multiple Grain Attributes and Stover", ip.com, May 26, 2009, 17 pages.
Breen, "Plant Identification: Examining Leaves", Oregon State University, 2020, 8 pages.
Caglayan et al., A Plant Recognition Approach Using Shape and Color Features in Leaf Images, Sep. 2013, 11 pages.
Casady et al., "Precision Agriculture Yield Monitors" University of Missouri—System, 4 pages, 1998.
Apan et al., "Predicting Grain Protein Content in Wheat Using Hyperspectral Sensing of In-season Crop Canopies and Partial Least Squares Regression" 18 pages, 2006.
Xu et al., "Prediction of Wheat Grain Protein by Coupling Multisource Remote Sensing Imagery and ECMWF Data", Apr. 24, 2020, 21 pages.
Day, "Probability Distributions of Field Crop Yields," American Journal of Agricultural Economics, vol. 47, Issue 3, Aug. 1965, Abstract Only, 1 page.
Butzen, "Reducing Harvest Losses in Soybeans", Pioneer, Jul. 23, 2020, 3 pages.
Martin et al., "Relationship between secondary variables and soybean oil and protein concentration", Abstract Only, 1 page., 2007.
Torres, "Precision Planting of Maize" Dec. 2012, 123 pages.
Leu et al., Grazing Corn Residue Using Resources and Reducing Costs, Aug. 2009, 4 pages.
"No-Till Soils", Soil Heath Brochure, 2 pages, last accessed Jul. 14, 2020.
Strickland et al., "Nitrate Toxicity in Livestock" Oklahoma State University, Feb. 2017, 2 pages.
Strickland et al., "Nitrate Toxicity in Livestock" Oklahoma State University, 8 pages, Feb. 2017.
Brownlee, "Neural Networks are Function Approximation Algorithms", Mar. 18, 2020, 13 pages.
Thompson, "Morning glory can make it impossible to harvest corn", Feb. 19, 2015, 3 pages.
Tumlison, "Monitoring Growth Development and Yield Estimation of Maize Using Very High-Resolution Uavimages in Gronau, Germany", Feb. 2017, 63 pages.
Hunt, "Mapping Weed Infestations Using Remote Sensing", 8 pages, Jul. 19, 2005.
Wright, et al., "Managing Grain Protein in Wheat Using Remote Sensing", 12 pages, 2003.
"Malting Barley in Pennsylvania", Agronomy Facts 77, 6 pages, Code EE0179 Jun. 2016.
"Green stem syndrome in soybeans", Agronomy eUpdate Issue 478 Oct. 10, 2014, 3 pages.
"Keep Weed Seed Out of Your Harvest", Aug. 8, 2019, 1 pages.
Hodrius et al., "The Impact of Multi-Sensor Data Assimilation on Plant Parameter Retrieval and Yield Estimation for Sugar Beet", The International Archives of the Photogrammetry, Remote Sensing and Spatial Information Sciences, vol. XL-7/W3, 2015, 36th International Symposium on Remote Sensing of Environment, May 11-15, 2015, Berlin, Germany, 7 pages.
Fernandez-Quintanilla et al., "Is the current state of the art of weed monitoring suitable for site-specific weed management in arable crops?", Feb. 2018, 35 pages.
Anonymously, "Improved System and Method for Controlling Agricultural Vehicle Operation Using Historical Data", Dec. 16, 2009, 8 pages.
Anonymously, "System and Method for Controlling Agricultural Vehicle Operation Using Historical Data", Jun. 30, 2009, 8 pages.

"Leafsnap, a new mobile app that identifies plants by leaf shape, is launched by Smithsonian and collaborators", May 2, 2011, 5 pages.
Insect Gallery, Department of Entomology, Kansas State University, Oct. 19, 2020, 8 pages.
Licht, "Influence of Corn Seeding Rate, Soil Attributes, and Topographic Characteristics on Grain Yield, Yield Components, and Grain Composition", 2015, 107 pages.
"Notice of Retraction Virtual simulation of plant with individual stem based on crop growth model", May 3, 2017, 7 pages.
Ma et al., "Identification of Fusarium Head Blight in Winter Wheat Ears Using Continuous Wavelet Analysis", Dec. 19, 2019, 15 pages.
Leland, "Who Did that? Identifying Insect Damage", Apr. 1, 2015, 4 pages.
"How to improve maize protein content" https://www.yara.co.uk/crop-nutrition/forage-maize/improving-maize-protein-content, Sep. 30, 2020, 10 pages.
Hafemeister, "Weed control at harvest, combines are ideal vehicles for spreading weed seeds", Sep. 25, 2019, 3 pages.
"Harvesting Tips", Northern Pulse Growers Association, 9 pages, Jan. 31, 2001.
Wortmann et al., "Harvesting Crop Residues", Aug. 10, 2020, 8 pages.
"Harvesting", Oklahoma State University, Canola Swathing Guide, 2010, 9 pages, last accessed Jul. 14, 2020.
Hanna, "Harvest Tips for Lodged Corn", Sep. 6, 2011, 3 pages.
"Green Weeds Complicate Harvest", Crops, Slider, Sep. 26, 2012, 2 pages.
"Agrowatch Green Vegetation Index", Retrieved Dec. 11, 2020, 4 pages.
"Grazing Corn Residues" (http://www.ca.uky.edu), 3 pages, Aug. 24, 2009.
Jarnevich et al., Forecasting Weed Distributions Using Climate Data: A GIS Early Warning Tool, Downloaded on Jul. 13, 2020, 12 pages.
Combine Cutting and Feeding Mechanisms in the Southeast, By J-K Park, Agricultural Research Service, U.S. Dept. of Agriculture, 1963, 1 page.
Hartzler, "Fate of weed seeds in the soil", 4 pages, Jan. 31, 2001.
Digman, "Combine Considerations for a Wet Corn Harvest", Extension SpecialistUW—Madison, 3 pages, Oct. 29, 2009.
S-Series Combine and Front End Equipment Optimization, John Deere Harvester Works, 20 pages Date: Oct. 9, 2017.
Determining yield monitoring system delay time with geostatistical and data segmentation approaches (https://www.ars.usda.gov/ARSUserFiles/50701000/cswq-0036-128359.pdf) Jul. 2002, 13 pages.
Precision Agriculture: Yield Monitors (dated Nov. 1998—metadata; last accessed Jul. 16, 2020) (https://extensiondata.missouri.edu/pub/pdf/envqual/wq0451.pdf) 4 pages.
Paul et al., "Effect of soil water status and strength on trafficability" (1979) (https://www.nrcresearchpress.com/doi/pdfplus/10.4141/cjss79-035), 12 pages, Apr. 23, 1979.
Sick, "Better understanding corn hybrid characteristics and properties can impact your seed decisions" (https://emergence.fbn.com/agronomy/corn-hybrid-characteristics-and-properties-impact-seed-decisions) By Steve Sick, FBN Breeding Project Lead | Sep. 21, 2018, 8 pages.
Robertson et al., "Maize Stalk Lodging: Morphological Determinants of Stalk Strength" Mar. 2017, 10 pages.
Martin, et al., "Breakage Susceptibility and Hardness of Corn Kernels of Various Sizes and Shapes", May 1987, 10 Pages.
7 Combine Tweaks to Boost Speed (https://www.agriculture.com/machinery/harvest-equipment/7-combine-tweaks-to-boost-speed_203-ar33059) 8 pages, Aug. 19, 2018.
Managing corn harvest this fall with variable corn conditions (https://www.ocj.com/2019/10/managing-corn-harvest-this-fall-with-variable-corn-conditions/), 4 pages, Oct. 10, 2019.
Reducing Aflatoxin in Corn During Harvest and Storage (https://extension.uga.edu/publications/detail.html?number=B1231&title=Reducing%20Aflatoxin%20in%20Corn%20During%20Harvest%20and%20Storage), 9 pages, Published with Full Review on Apr. 19, 2017.

(56) References Cited

OTHER PUBLICATIONS

Variable Rate Applications to Optimize Inputs (https://www.cotton.org/tech/physiology/cpt/miscpubs/upload/CPT-v9No2-98-REPOP.pdf), 8 pages, Nov. 2, 1998.
Robin Booker, Video: Canadian cage mill teams up with JD (https://www.producer.com/2019/12/video-canadian-cage-mill-teams-up-with-jd/) , 6 pages, Dec. 19, 2019.
Jarnevich, et al. "Forecasting Weed Distributions using Climate Data: A GIS Early Warning Tool", Invasive Plant Science and Management, 11 pages, Jan. 20, 2017.
Burks, "Classification of Weed Species Using Color Texture Features and Discriminant Analysis" (http://citeseerx.ist.psu.edu/viewdoc/download?doi=10.1.1.468.5833&rep=rep1&type=pdf), 8 pages, 2000.
John Deere, https://www.youtube.com/watch?v=1Gq77CfdGI4&list=PL1KGsSJ4CWk4rShNb3-sTMOliL8meHBL5 (last accessed Jul. 14, 2020), Jun. 15, 2020, 5 pages.
Combine Adjustments (http://corn.agronomy.wisc.edu/Management/L036.aspx), 2 pages, Originally written Feb. 1, 2006; last updated Oct. 18, 2018.
Ardekani, "Off- and on-ground GPR techniques for field-scale soil moisture mapping" Jun. 2013, 13 pages.
Does an Adaptive Gearbox Really Learn How You Drive? (https://practicalmotoring.com.au/voices/does-an-adaptive-gearbox-really-learn-how-you-drive/), Oct. 30, 2019, 8 pages.
https://www.researchgate.net/publication/222527694_Energy_Requirement_Model_for_a_Combine_Harvester_Part_I_Development_of_Component_Models, Abstract Only, Jan. 2005.
http://canola.okstate.edu/cropproduction/harvesting, 8 pages, Aug. 2011.
"Tips and Tricks of Harvesting High Moisture Grain", https://www.koenigequipment.com/blog/tips-and-tricks-of-harvesting-highmoisture-grain, 5 pages, last accessed Feb. 11, 2021.
Hoff, Combine Adjustements, Mar. 1943, 8 pages.
Haung et al., "Accurate Weed Mapping and Prescription Map Generation Based onFully Convolutional Networks Using UAV imagery", 14 pages, Oct. 1, 2018.
Thompson, "Morning glory can make it impossible to harvest corn", Feb. 19, 2015, 4 pages.
Prosecution History for U.S. Appl. No. 16/380,691 including: Notice of Allowance dated Mar. 10, 2021 and Application and Drawings filed Apr. 10, 2019, 46 pages.
U.S. Appl. No. 16/831,216 Application and Drawings filed Mar. 26, 2020, 56 pages.
Notice of Allowance for U.S. Appl. No. 16/380,531 dated Apr. 5, 2021, 5 pages.
Apan et al., "Predictive Mapping of Blackberry in the Condamine Catchment Using Logistic Regressiona dn Spatial Analysis", Jan. 2008, 12 pages.
Robson, "Remote Sensing Applications for the Determination of Yield, Maturity and Aflatoxin Contamination in Peanut", Oct. 2007, 275 pages.
Bhattaral et al., "Remote Sensing Data to Detect Hessian Fly Infestation in Commercial Wheat Fields", Apr. 16, 2019, 8 pages.
Towery, et al., "Remote Sensing of Crop Hail Damage", Jul. 21, 1975, 31 pages.
Sa et al., "WeedMap: A Large-Scale Semantic Weed Mapping Framework Using Aerial Multispectral Imaging and Deep Neural Network for Precision Farming", Sep. 7, 2018, 25 pages.
Mathyam et al., "Remote Sensing of Biotic Stress in Crop Plants and Its Applications for Pest Management", Dec. 2011, 30 pages.
Bhattarai et al., "Remote Sensing Data to Detect Hessian Fly Infestation in Commercial Wheat Fields", Apr. 16, 2019, 8 pages.
Martinez-Feria et al., "Evaluating Maize and Soybean Grain Dry-Down In The Field With Predictive Algorithms and Genotype-by-Environmental Analysis", May 9, 2019, 13 pages.
"GIS Maps for Agriculture", Precision Agricultural Mapping, Retrieved Dec. 11, 2020, 6 pages.

Paul, "Scabby Wheat Grain? Increasing Your Fan Speed May Help", https://agcrops.osu.edu/newsletter/corn-newsletter/2015-20/scabby-wheat-grain-Increasing-yourfan-speed-may-help, C.O.R.N Newsletter//2015-20, 3 pages.
Clay et al., "Scouting for Weeds", SSMG-15, 4 pages, 2002.
Taylor et al., "Sensor-Based Variable Rate Application for Cotton", 8 pages, 2010.
Christiansen et al., "Designing and Testing a UAV Mapping System for Agricultural Field Surveying", Nov. 23, 2017, 19 pages.
Haung et al., "AccurateWeed Mapping and Prescription Map Generation Based on Fully Convolutional Networks Using UAV Imagery", Oct. 1, 2018, 12 pages.
Morrison, "Should You Use Tillage to Control Resistant Weeds", Aug. 29, 2014, 9 pages.
Morrison, "Snow Trapping Snars Water", Oct. 13, 2005, 3 pages.
"Soil Zone Index", https://www.satimagingcorp.com/applications/natural-resources/agricultu . . . , Retrieved Dec. 11, 2020, 5 pages.
Malvic, "Soybean Cyst Nematode", University of Minnesota Extension, Oct. 19, 2020, 3 pages.
Unglesbee, "Soybean Pod Shatter—Bad Enough to Scout Before Harvest?—DTN", Oct. 17, 2018, 4 pages.
Tao, "Standing Crop Residue Can Reduce Snow Drifting and Increase Soil Moisture", 2 pages, last accessed Jul. 14, 2020.
Berglund, et al., "Swathing and Harvesting Canola", Jul. 2019, 8 pages.
Bell et al., "Synthetic Aperture Radar and Optical Remote Sensing of Crop Damage Attributed to Severe Weather in the Central United States", Jul. 25, 2018, 1 page.
Rosencrance, "Tabletop Grapes in India to Be Picked by Virginia Tech Robots", Jul. 23, 2020, 8 pages.
Lofton, et al., The Potential of Grazing Grain Sorghum Residue Following Harvest, May 13, 2020, 11 pages.
Beal et al., "Time Shift Evaluation to Improve Yield Map Quality", Published in Applied Engineering in Agriculture vol. 17(3): 385-390 (© 2001 American Society of Agricultural Engineers ), 9 pages.
"Tips and Tricks of Harvesting High Moisture Grain", https://www.koenigequipment.com/blog/tips-and-tricks-of-harvesting-highmoisture-grain, 7 pages, last accessed Jul. 14, 2020.
Ransom, "Tips for Planting Winter Wheat and Winter Rye (for Grain) (Aug. 15, 2019)", 2017, 3 pages.
AgroWatch Tree Grading Maps, "The Grading Maps and Plant Count Reports", https://www.satimagingcorp.com/applications/natural-resources/agricultu . . . , Retrieved Dec. 11, 2020, 4 pages.
Ackley, "Troubleshooting Abnormal Corn Ears", Jul. 23, 2020, 25 pages.
Smith, "Understanding Ear Flex", Feb. 25, 2019, 17 pages.
Carroll et al., "Use of Spectral Vegetation Indicies Derived from Airborne Hyperspectral Imagery For Detection of European Corn Borer Infestation in Iowa Com Plots", Nov. 2008, 11 pages.
Agriculture, "Using drones in agriculture and capturing actionable data", Retrieved Dec. 11, 2020, 18 pages.
Bentley et al., "Using Landsat to Identify Thunderstorm Damage in Agricultural Regions", Aug. 28, 2001, 14 pages.
Duane Grant and the Idaho Wheat Commission, "Using Remote Sensing to Manage Wheat Grain Protein", Jan. 2, 2003, 13 pages.
Zhang et al., "Using satellite multispectral imagery for damage mapping of armyworm (*Spodoptera frugiperda*) in maize at a regional scale", Apr. 10, 2015, 14 pages.
Booker, "Video: Canadian cage mill teams up with JD", Dec. 19, 2019, 6 pages.
AgTalk Home, "Best Combine to Handle Weeds", Posted Nov. 23, 2018, 9 pages.
"Volunteer corn can be costly for soybeans", Jun. 2, 2016, 1 page.
Pflanz, et al., "Weed Mapping with UAS Imagery and a Bag of Visual Words Based Image Classifier", Published Sep. 24, 2018, 17 pages.
Hartzler, "Weed seed predation in agricultural fields", 9 pages, 2009.
Sa et al., "Weedmap: A Large-Scale Sematnic Weed Mapping Framework Using Aerial Multispectral Imaging and Deep Neural Netowrk for Precision Farming", Sep. 6, 2018, 25 pages.

(56) References Cited

OTHER PUBLICATIONS

Nagelkirk, Michigan State University-Extension, "Wheat Harvest: Minimizing the Risk of Fusarium Head Scab Losses", Jul. 11, 2013, 4 pages.
Saskatchewan, "Wheat: Winter Wheat", (https://www.saskatchewan.ca/business/agriculture-natural-resources-and-industry/agribusiness-farmers-and-ranchers/crops-and-irrigation/field-crops/cereals-barley-wheat-oats-triticale/wheat-winter-wheat) 5 pages, last accessed Jul. 14, 2020.
Quora, "Why would I ever use sport mode in my automatic transmission car? Will this incrase fuel efficiency or isit simply a feature that makes form more fun when driving?", Aug. 10, 2020, 5 pages.
Wade, "Using a Drone's Surface Model to Estimate Crop Yields & Assess Plant Health", Oct. 19, 2015, 14 pages.
Mathyam et al., "Remote Sensing of Biotic Stress in Crop Plants and Its Applications for Pest Stress", Dec. 2011, 30 pages.
"Four Helpful Weed-Management Tips for Harvest Time", 2 pages, Sep. 4, 2019.
Franz et al., "The role of topography, soil, and remotely sensed vegetation condition towards predicting crop yield"; University of Nebraska—Lincoln, Mar. 23, 2020, 44 pages.
Peiffer et al., The Genetic Architecture of Maize Stalk Strength:, Jun. 20, 2013, 14 pages.
Extended European Search Report and Written Opinion issued in European Patent Application No. 20208171.7, dated May 11, 2021, in 05 pages.
Cordoba, M.A., Bruno, C.I. Costa, J.L. Peralta, N.R. and Balzarini, M.G., 2016, Protocol for multivariate homegeneous zone delineation in precision agriculture, biosystems engineering, 143, pp. 95-107.
Pioneer Estimator, "Corn Yield Estimator" accessed on Feb. 13, 2018, 1 page. retrieved from: https://www.pioneer.com/home/site/us/tools-apps/growing-tools/corn-yield-estimator/.
Guindin, N. "Estimating Maize Grain Yield From Crop Biophysical Parameters Using Remote Sensing", Nov. 4, 2013, 19 pages.
EP Application No. 19203883.4-1004 Office Action dated May 3, 2021, 4 pages.
Iowa State University Extension and Outreach, "Harvest Weed Seed Control", Dec. 13, 2018, 6 pages. https://crops.extension.iastate.edu/blog/bob-hartzler/harvest-weed-seed-control.
Getting Rid Of WeedsThrough Integrated Weed Management, accessed on Jun. 25, 2021, 10 pages. https://integratedweedmanagement.org/index.php/iwm-toolbox/the-harrington-seed-destructor.
The Importance of Reducing Weed Seeds, Jul. 2018, 2 pages. https://www.aphis.usda.gov/plant_health/soybeans/soybean-handouts.pdf.
Alternative Crop Guide, Published by the Jefferson Institute, "Buckwheat", Revised Jul. 2002. 4 pages.
Lamsal et al. "Sugarcane Harvest Logistics in Brazil" Iowa Research Online, Sep. 11, 2013, 27 pages.
Jensen, "Algorithms for Operational Planning of Agricultural Field Operations", Mechanical Engineering Technical Report ME-TR-3, Nov. 9, 2012, 23 pages.
Chauhan, "Remote Sensing of Crop Lodging", Nov. 16, 2020, 16 pages.

\* cited by examiner

ND CONTROL
MAP GENERATION AND CONTROL SYSTEM

CROSS-REFERENCE TO RELATED APPLICATION

The present application is a continuation of and claims priority of U.S. patent application Ser. No. 17/067,038, filed Oct. 9, 2020, the content of which is hereby incorporated by reference in its entirety.

FIELD OF THE DESCRIPTION

The present description relates to agricultural machines, forestry machines, construction machines and turf management machines.

BACKGROUND

There are a wide variety of different types of agricultural machines. Some agricultural machines include harvesters, such as combine harvesters, sugar cane harvesters, cotton harvesters, self-propelled forage harvesters, and windrowers. Some harvester can also be fitted with different types of heads to harvest different types of crops.

Agricultural harvesters may operate differently in areas of varying yield in fields unless the settings in the agricultural harvester are changed. For instance, when a harvester transitions from an area in a field with a first yield to an area in the field with a second yield, where the second yield is higher than the first yield, the change from a reduced amount of grain being harvested to an increased amount of grain may degrade the performance of the harvester if operating settings are not changed. Therefore, an operator may attempt to modify control of the harvester upon transitioning between an area of increased or reduced yield during the harvesting operation.

The discussion above is merely provided for general background information and is not intended to be used as an aid in determining the scope of the claimed subject matter.

SUMMARY

One or more information maps are obtained by an agricultural work machine. The one or more information maps map one or more agricultural characteristic values at different geographic locations of a field. An in-situ sensor on the agricultural work machine senses an agricultural characteristic as the agricultural work machine moves through the field. A predictive map generator generates a predictive map that predicts a predictive agricultural characteristic at different locations in the field based on a relationship between the values in the one or more information maps and the agricultural characteristic sensed by the in-situ sensor. The predictive map can be output and used in automated machine control.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to examples that solve any or all disadvantages noted in the background.

DETAILED DESCRIPTION

Figure 1:
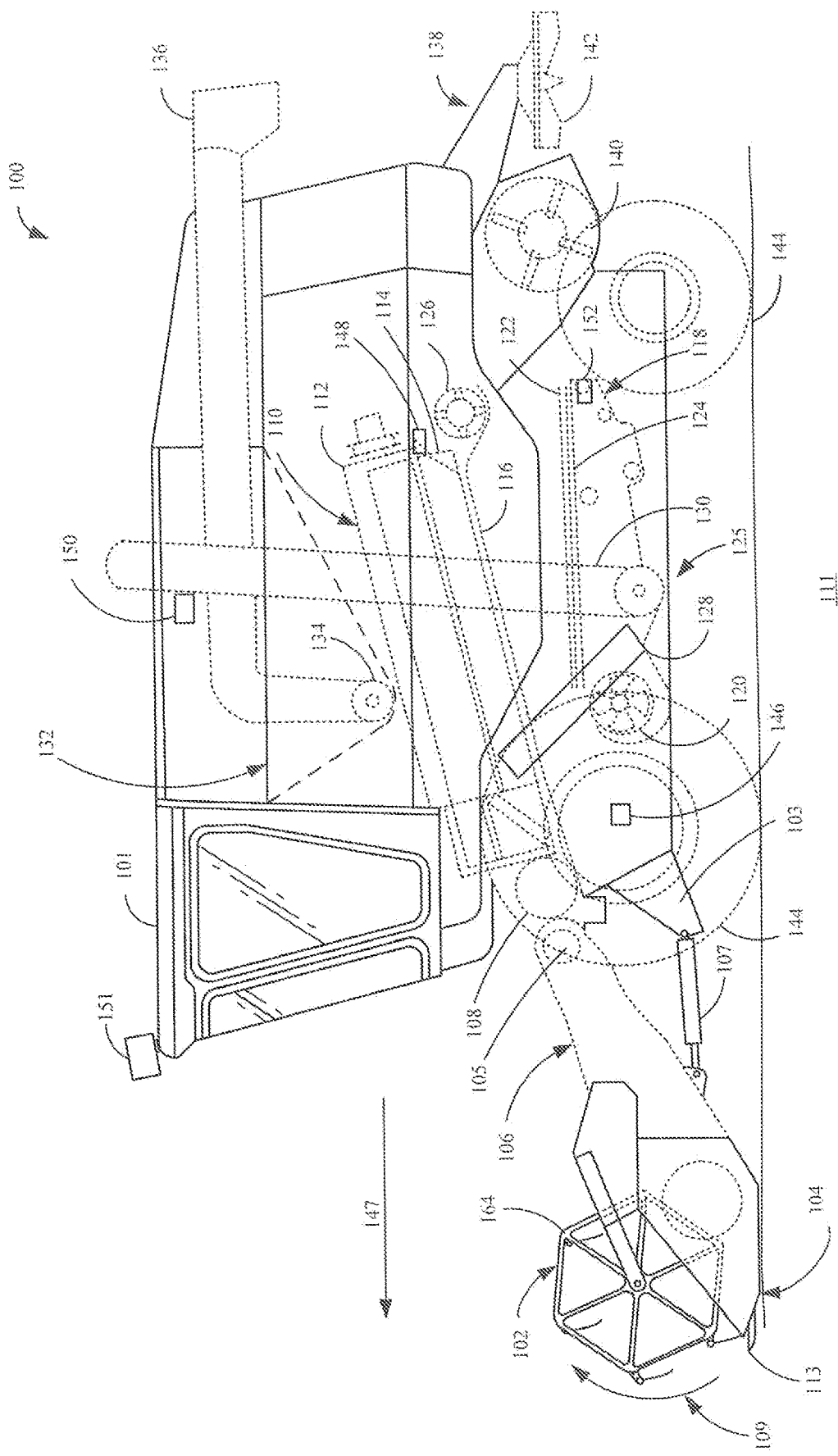
FIG. 1 is a partial pictorial, partial schematic illustration of one example of an agricultural harvester.

For the purposes of promoting an understanding of the principles of the present disclosure, reference will now be made to the examples illustrated in the drawings, and specific language will be used to describe the same. It will nevertheless be understood that no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, steps, or a combination thereof described with respect to one example may be combined with the features, components, steps, or a combination thereof described with respect to other examples of the present disclosure.

The present description relates to using in-situ data taken concurrently with an agricultural operation, in combination with prior data, to generate a functional predictive map and, more particularly, a functional predictive yield map. In some examples, the functional predictive yield map can be used to control an agricultural work machine, such as an agricultural harvester. As discussed above, performance of an agricultural harvester may be degraded when the agricultural harvester engages areas of varying yield unless machine settings are also changed. For instance, in an area of reduced yield, the agricultural harvester may move over the ground quickly and move material through the machine at an increased feed rate. When encountering an area of increased yield, the speed of the agricultural harvester over the ground may decrease, thereby decreasing the feed rate into the agricultural harvester, or the agricultural harvester may plug, lose grain, or face other problems. For example, areas of a field having increased yield may have crop plants with different physical structures than in areas of the field having reduced yield. For instance, in areas of increased yield, some plants may have thicker stalks, broader leaves, larger, or more heads, etc. These variations in plant structure in areas of varying yield may also cause the performance of the agricultural harvester to vary when the agricultural harvester moves through areas of varying yield.

A vegetative index map illustratively maps vegetative index values, which may be indicative of vegetative growth, across different geographic locations in a field of interest. One example of a vegetative index includes a normalized difference vegetation index (NDVI). There are many other vegetative indices, and all of these vegetative indices are within the scope of the present disclosure. In some examples, a vegetative index may be derived from sensor readings of one or more bands of electromagnetic radiation reflected by the plants. Without limitations, these bands may be in the microwave, infrared, visible, or ultraviolet portions of the electromagnetic spectrum.

A vegetative index map can thus be used to identify the presence and location of vegetation. In some examples, a vegetative index map enables crops to be identified and georeferenced in the presence of bare soil, crop residue, or other plants, including crop or weeds. For instance, towards the beginning of a growing season, when a crop is in a growing state, the vegetative index may show the progress of the crop development. Therefore, if a vegetative index map is generated early in the growing season or midway through the growing season, the vegetative index map may be indicative of the progress of the development of the crop plants. For instance, the vegetative index map may indicate whether the plant is stunted, establishing a sufficient canopy, or other plant attributes that are indicative of plant development.

A historical yield map illustratively maps yield values across different geographic locations in one or more field(s) of interest. These historical yield maps are collected from past harvesting operations on the field(s). A yield map may show yield in yield value units. One example of a yield value unit includes dry bushels per acre. In some examples, a historical yield map may be derived from sensor readings of one or more yield sensors. Without limitation, these yield sensors may include gamma ray attenuation sensors, impact plate sensors, load cells, cameras, or other optical sensors and ultrasonic sensors, among others.

The present discussion also includes predictive maps that predict a characteristic based on a prior information map and a relationship to sensed data obtained from an in-situ sensor. These predictive maps include a predictive yield map. In one example, the predictive yield map is generated by receiving a prior vegetative index map and sensed yield data obtained from an in-situ yield sensor and determining a relationship between the prior vegetative index map and the sensed yield data obtained from a signal from the in-situ yield sensor, and using the relationship to generate the predictive yield map based on the relationship and the prior vegetative index map. The predictive yield map can be created based on other prior information maps or generated in other ways as well. For example, the predictive yield can be generated based on satellite images, growth models, weather models, etc. Or for example, a predictive yield map may be based in whole or in part on a topographic map, a soil type map, a soil constituent map, or a soil health map.

The present discussion thus proceeds with respect to examples in which a system receives one or more of a vegetative index map, a historical yield map of a field, or a map generated during a prior operation and also uses an in-situ sensor to detect a characteristic or variable indicative of yield during a harvesting operation. The system generates a model that models a relationship between the vegetative index values or historical yield values from one or more of the maps and the in-situ data from the in-situ sensor. The model is used to generate a functional predictive yield map that predicts an anticipated crop yield in the field. The functional predictive yield map, generated during the harvesting operation, can be presented to an operator or other user or used in automatically controlling an agricultural harvester during the harvesting operation or both.

FIG. 1 is a partial pictorial, partial schematic, illustration of a self-propelled agricultural harvester 100. In the illustrated example, agricultural harvester 100 is a combine harvester. Further, although combine harvesters are provided as examples throughout the present disclosure, it will be appreciated that the present description is also applicable to other types of harvesters, such as cotton harvesters, sugarcane harvesters, self-propelled forage harvesters, windrowers, or other agricultural work machines. Consequently, the present disclosure is intended to encompass the various types of harvesters described and is, thus, not limited to combine harvesters. Moreover, the present disclosure is directed to other types of work machines, such as agricultural seeders and sprayers, construction equipment, forestry equipment, and turf management equipment where generation of a predictive map may be applicable. Consequently, the present disclosure is intended to encompass these various types of harvesters and other work machines and is, thus, not limited to combine harvesters.

As shown in FIG. 1, agricultural harvester 100 illustratively includes an operator compartment 101, which can have a variety of different operator interface mechanisms, for controlling agricultural harvester 100. Agricultural harvester 100 includes front-end equipment, such as a header 102, and a cutter generally indicated at 104. Agricultural harvester 100 also includes a feeder house 106, a feed accelerator 108, and a thresher generally indicated at 110. The feeder house 106 and the feed accelerator 108 form part of a material handling subsystem 125. Header 102 is pivotally coupled to a frame 103 of agricultural harvester 100 along pivot axis 105. One or more actuators 107 drive movement of header 102 about axis 105 in the direction generally indicated by arrow 109. Thus, a vertical position of header 102 (the header height) above ground 111 over which the header 102 travels is controllable by actuating actuator 107. While not shown in FIG. 1, agricultural harvester 100 may also include one or more actuators that operate to apply a tilt angle, a roll angle, or both to the header 102 or portions of header 102. Tilt refers to an angle at which the cutter 104 engages the crop. The tilt angle is increased, for example, by controlling header 102 to point a distal edge 113 of cutter 104 more toward the ground. The tilt angle is decreased by controlling header 102 to point the distal edge 113 of cutter 104 more away from the ground.

The roll angle refers to the orientation of header 102 about the front-to-back longitudinal axis of agricultural harvester 100.

Thresher 110 illustratively includes a threshing rotor 112 and a set of concaves 114. Further, agricultural harvester 100 also includes a separator 116. Agricultural harvester 100 also includes a cleaning subsystem or cleaning shoe (collectively referred to as cleaning subsystem 118) that includes a cleaning fan 120, chaffer 122, and sieve 124. The material handling subsystem 125 also includes discharge beater 126, tailings elevator 128, clean grain elevator 130, as well as unloading auger 134 and spout 136. The clean grain elevator moves clean grain into clean grain tank 132. Agricultural harvester 100 also includes a residue subsystem 138 that can include chopper 140 and spreader 142. Agricultural harvester 100 also includes a propulsion subsystem that includes an engine that drives ground engaging components 144, such as wheels or tracks. In some examples, a combine harvester within the scope of the present disclosure may have more than one of any of the subsystems mentioned above. In some examples, agricultural harvester 100 may have left and right cleaning subsystems, separators, etc., which are not shown in FIG. 1.

In operation, and by way of overview, agricultural harvester 100 illustratively moves through a field in the direction indicated by arrow 147. As agricultural harvester 100 moves, header 102 (and the associated reel 164) engages the crop to be harvested and gathers the crop toward cutter 104. An operator of agricultural harvester 100 can be a local human operator, a remote human operator, or an automated system. An operator command is a command by an operator. The operator of agricultural harvester 100 may determine one or more of a height setting, a tilt angle setting, or a roll angle setting for header 102. For example, the operator inputs a setting or settings to a control system, described in more detail below, that controls actuator 107. The control system may also receive a setting from the operator for establishing the tilt angle and roll angle of the header 102 and implement the inputted settings by controlling associated actuators, not shown, that operate to change the tilt angle and roll angle of the header 102. The actuator 107 maintains header 102 at a height above ground 111 based on a height setting and, where applicable, at desired tilt and roll angles. Each of the height, roll, and tilt settings may be implemented independently of the others. The control system responds to header error (e.g., the difference between the height setting and measured height of header 104 above ground 111 and, in some examples, tilt angle and roll angle errors) with a responsiveness that is determined based on a selected sensitivity level. If the sensitivity level is set at a greater level of sensitivity, the control system responds to smaller header position errors, and attempts to reduce the detected errors more quickly than when the sensitivity is at a lower level of sensitivity.

Returning to the description of the operation of agricultural harvester 100, after crops are cut by cutter 104, the severed crop material is moved through a conveyor in feeder house 106 toward feed accelerator 108, which accelerates the crop material into thresher 110. The crop material is threshed by rotor 112 rotating the crop against concaves 114. The threshed crop material is moved by a separator rotor in separator 116 where a portion of the residue is moved by discharge beater 126 toward the residue subsystem 138. The portion of residue transferred to the residue subsystem 138 is chopped by residue chopper 140 and spread on the field by spreader 142. In other configurations, the residue is released from the agricultural harvester 100 in a windrow. In other examples, the residue subsystem 138 can include weed seed eliminators (not shown) such as seed baggers or other seed collectors, or seed crushers or other seed destroyers.

Grain falls to cleaning subsystem 118. Chaffer 122 separates some larger pieces of material from the grain, and sieve 124 separates some of finer pieces of material from the clean grain. Clean grain falls to an auger that moves the grain to an inlet end of clean grain elevator 130, and the clean grain elevator 130 moves the clean grain upwards, depositing the clean grain in clean grain tank 132. Residue is removed from the cleaning subsystem 118 by airflow generated by cleaning fan 120. Cleaning fan 120 directs air along an airflow path upwardly through the sieves and chaffers. The airflow carries residue rearwardly in agricultural harvester 100 toward the residue subsystem 138.

Tailings elevator 128 returns tailings to thresher 110 where the tailings are re-threshed. Alternatively, the tailings also may be passed to a separate re-threshing mechanism by a tailings elevator or another transport device where the tailings are re-threshed as well.

FIG. 1 also shows that, in one example, agricultural harvester 100 includes ground speed sensor 146, one or more separator loss sensors 148, a clean grain camera 150, a forward looking image capture mechanism 151, which may be in the form of a stereo or mono camera, and one or more loss sensors 152 provided in the cleaning subsystem 118.

Ground speed sensor 146 senses the travel speed of agricultural harvester 100 over the ground. Ground speed sensor 146 may sense the travel speed of the agricultural harvester 100 by sensing the speed of rotation of the ground engaging components (such as wheels or tracks), a drive shaft, an axel, or other components. In some instances, the travel speed may be sensed using a positioning system, such as a global positioning system (GPS), a dead reckoning system, a long range navigation (LORAN) system, or a wide variety of other systems or sensors that provide an indication of travel speed.

Loss sensors 152 illustratively provide an output signal indicative of the quantity of grain loss occurring in both the right and left sides of the cleaning subsystem 118. In some examples, sensors 152 are strike sensors which count grain strikes per unit of time or per unit of distance traveled to provide an indication of the grain loss occurring at the cleaning subsystem 118. The strike sensors for the right and left sides of the cleaning subsystem 118 may provide individual signals or a combined or aggregated signal. In some examples, sensors 152 may include a single sensor as opposed to separate sensors provided for each cleaning subsystem 118.

Separator loss sensor 148 provides a signal indicative of grain loss in the left and right separators, not separately shown in FIG. 1. The separator loss sensors 148 may be associated with the left and right separators and may provide separate grain loss signals or a combined or aggregate signal. In some instances, sensing grain loss in the separators may also be performed using a wide variety of different types of sensors as well.

Agricultural harvester 100 may also include other sensors and measurement mechanisms. For instance, agricultural harvester 100 may include one or more of the following sensors: a header height sensor that senses a height of header 102 above ground 111; stability sensors that sense oscillation or bouncing motion (and amplitude) of agricultural harvester 100; a residue setting sensor that is configured to sense whether agricultural harvester 100 is configured to chop the residue, produce a windrow, etc.; a cleaning shoe fan speed sensor to sense the speed of cleaning fan 120; a concave clearance sensor that senses clearance between the rotor 112 and concaves 114; a threshing rotor speed sensor that senses a rotor speed of rotor 112; a chaffer clearance sensor that senses the size of openings in chaffer 122; a sieve clearance sensor that senses the size of openings in sieve 124; a material other than grain (MOG) moisture sensor that senses a moisture level of the MOG passing through agricultural harvester 100; one or more machine setting sensors configured to sense various configurable settings of agricultural harvester 100; a machine orientation sensor that senses the orientation of agricultural harvester 100; and crop property sensors that sense a variety of different types of crop properties, such as crop type, crop moisture, and other crop properties. Crop property sensors may also be configured to sense characteristics of the severed crop material as the crop material is being processed by agricultural harvester 100. For example, in some instances, the crop property sensors may sense grain quality such as broken grain, MOG levels; grain constituents such as starches and protein; and grain feed rate as the grain travels through the feeder house 106, clean grain elevator 130, or elsewhere in the agricultural harvester 100. The crop property sensors may also sense the feed rate of biomass through feeder house 106, through the separator 116 or elsewhere in agricultural harvester 100. The crop property sensors may also sense the feed rate as a mass flow rate of grain through elevator 130 or through other portions of the agricultural harvester 100 or provide other output signals indicative of other sensed variables. Crop property sensors can include one or more yield sensors that sense crop yield being harvested by agricultural harvester.

Yield sensor(s) can include a grain flow sensor that detects a flow of crop, such as grain, in material handling subsystem 125 or other portions of agricultural harvester 100. For example, a yield sensor can include a gamma ray attenuation sensor that measures flow rate of harvested grain. In another example, a yield sensor includes an impact plate sensor that detects impact of grain against a sensing plate or surface so as to measure mass flow rate of harvested grain. In another example, a yield sensor includes one or more load cells which measure or detect a load or mass of harvested grain. For example, one or more load cells may be located at a bottom of grain tank 132, wherein changes in the weight or mass of grain within grain tank 132 during a measurement interval indicates the aggregate yield during the measurement interval. The measurement interval may be increased for averaging or decreased for more instantaneous measurements. In another example, a yield sensor includes cameras or optical sensing devices that detect the size or shape of an aggregated mass of harvested grain, such as the shape of the mound or height of a mound of grain in grain tank 132. The change in shape or height of the mound during the measurement interval indicates an aggregate yield during the measurement interval. In other examples, other yield sensing technologies are employed. For instance, in one example, a yield sensor includes two or more of the above described sensors, and the yield for a measurement interval is determined from signals output by each of the multiple different types of sensors. For example, yield is determined based upon signals from a gamma ray attenuation sensor, an impact plate sensor, load cells within grain tank 132, and optical sensors along grain tank 132.

Prior to describing how agricultural harvester 100 generates a functional predictive yield map and uses the functional predictive yield map for presentation or control, a brief description of some of the items on agricultural harvester 100, and their operation, will first be described. The description of FIGS. 2 and 3 describe receiving a general type of prior information map and combining information from the prior information map with a georeferenced sensor signal generated by an in-situ sensor, where the sensor signal is indicative of a characteristic in the field, such as characteristics of crop or weeds present in the field. Characteristics of the field may include, but are not limited to, characteristics of a field such as slope, weed intensity, weed type, soil moisture, surface quality; characteristics of crop properties such as crop height, crop moisture, crop density, crop state; characteristics of grain properties such as grain moisture, grain size, grain test weight; and characteristics of machine performance such as loss levels, job quality, fuel consumption, and power utilization. A relationship between the characteristic values obtained from in-situ sensor signals and the prior information map values is identified, and that relationship is used to generate a new functional predictive map. A functional predictive map predicts values at different geographic locations in a field, and one or more of those values may be used for controlling a machine, such as one or more subsystems of an agricultural harvester. In some instances, a functional predictive map can be presented to a user, such as an operator of an agricultural work machine, which may be an agricultural harvester. A functional predictive map may be presented to a user visually, such as via a display, haptically, or audibly. The user may interact with the functional predictive map to perform editing operations and other user interface operations. In some instances, a functional predictive map can be used for one or more of controlling an agricultural work machine, such as an agricultural harvester, presentation to an operator or other user, and presentation to an operator or user for interaction by the operator or user.

Figure 2:
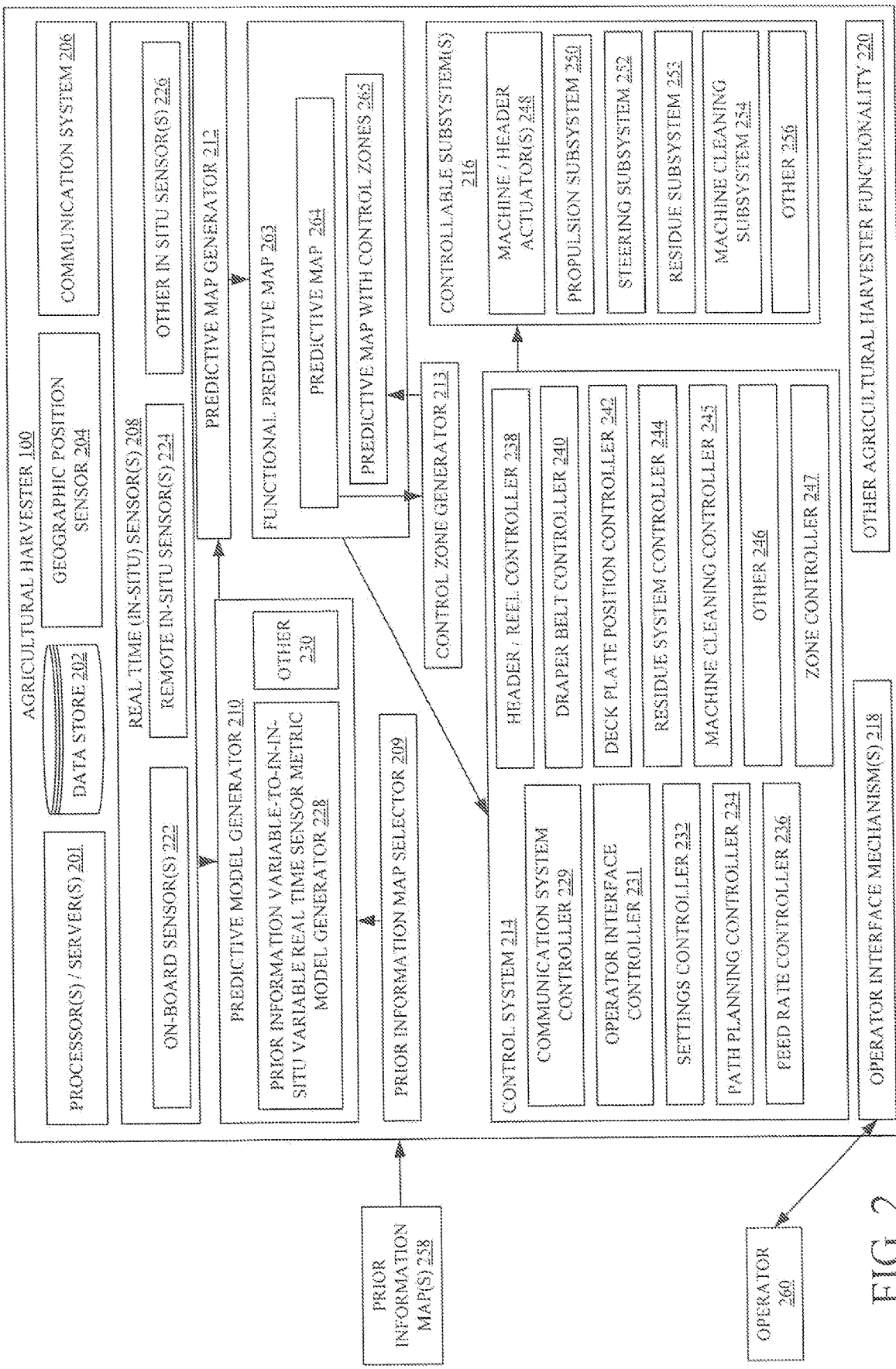
FIG. 2 is a block diagram showing some portions of an agricultural harvester in more detail, according to some examples of the present disclosure.
Figure 3A:
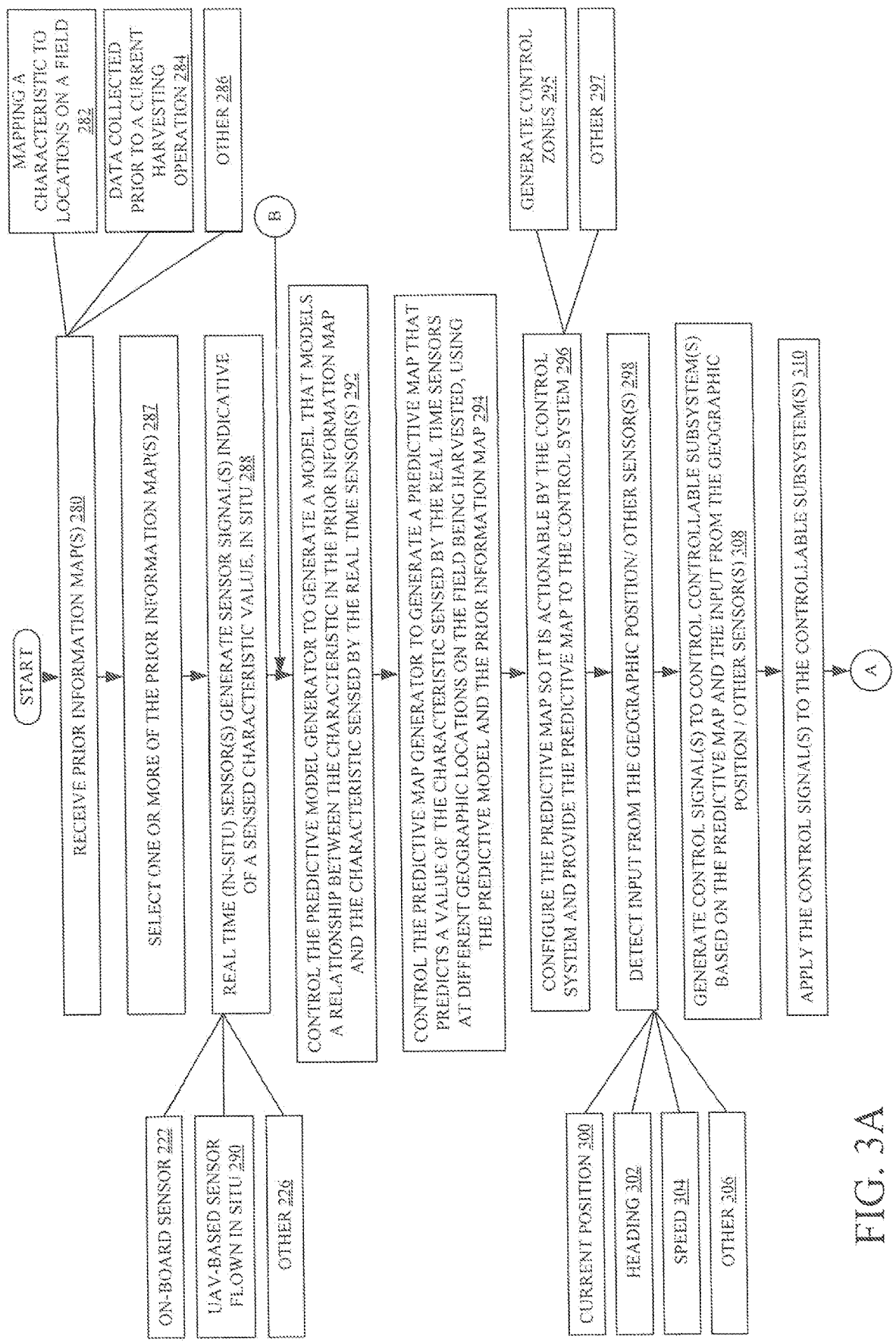
FIGS. 3A-3B (collectively referred to herein as FIG. 3) show a flow diagram illustrating an example of operation of an agricultural harvester in generating a map.
Figure 3B:
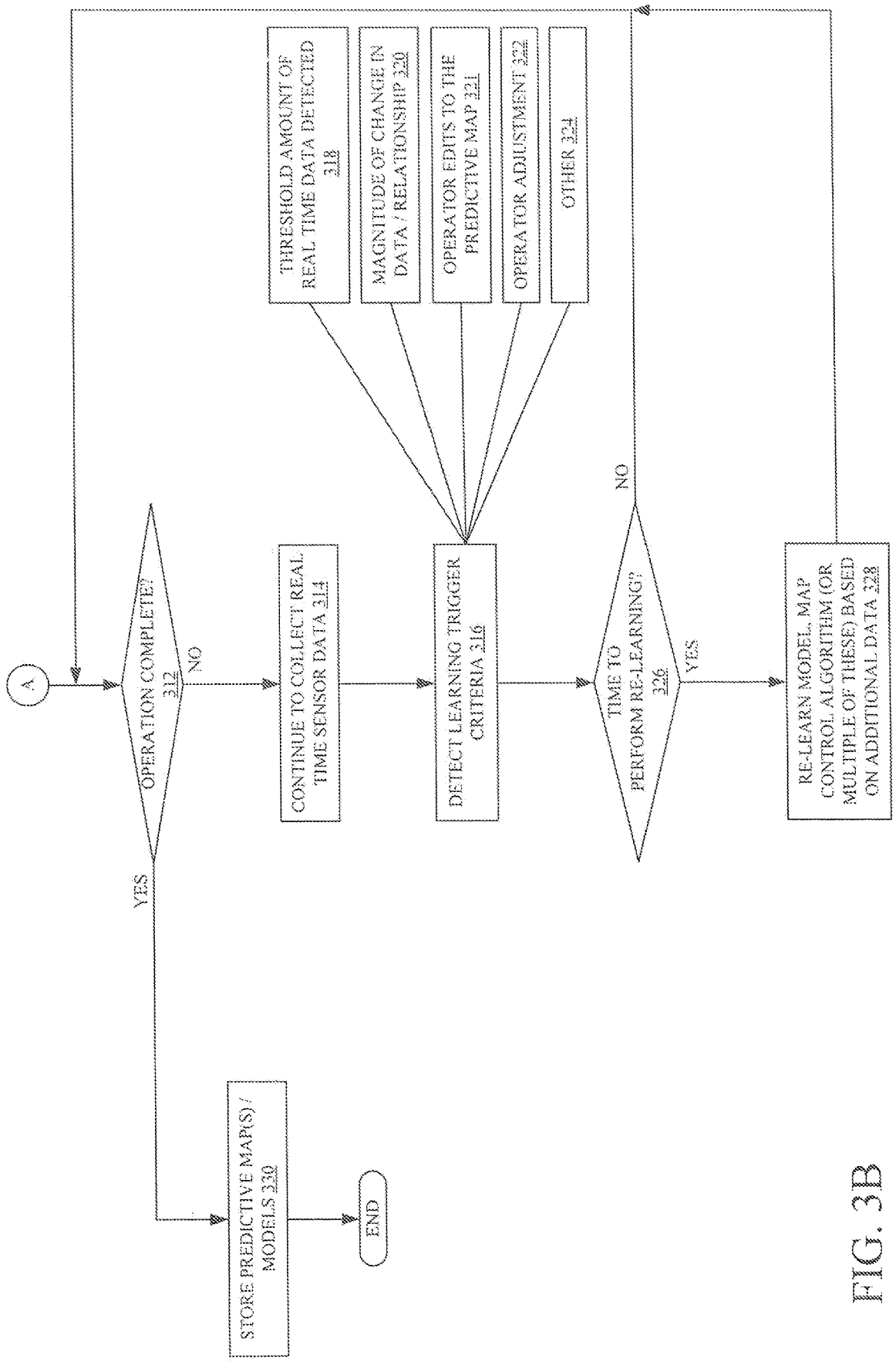
Figure 4:
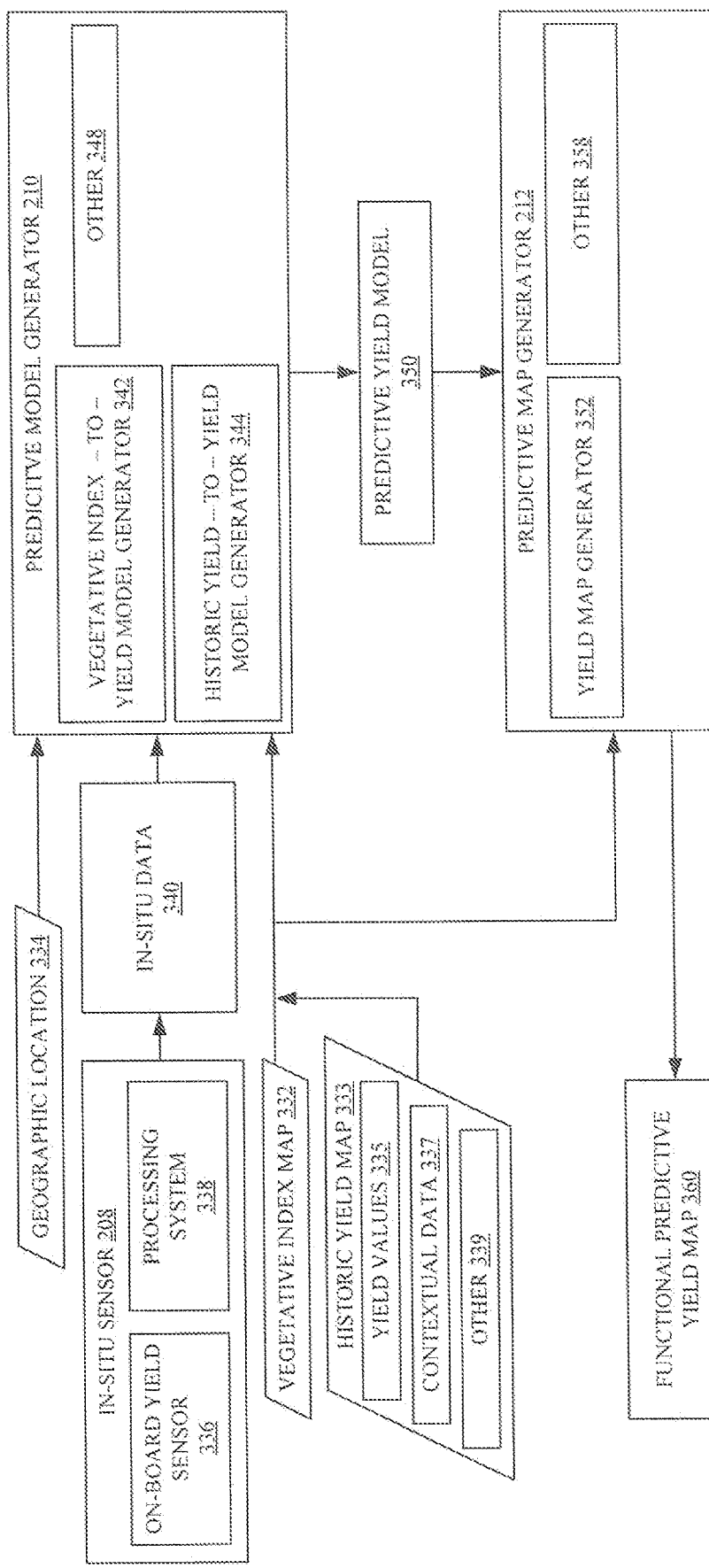
FIG. 4 is a block diagram showing one example of a predictive model generator and a predictive map generator.
Figure 5:
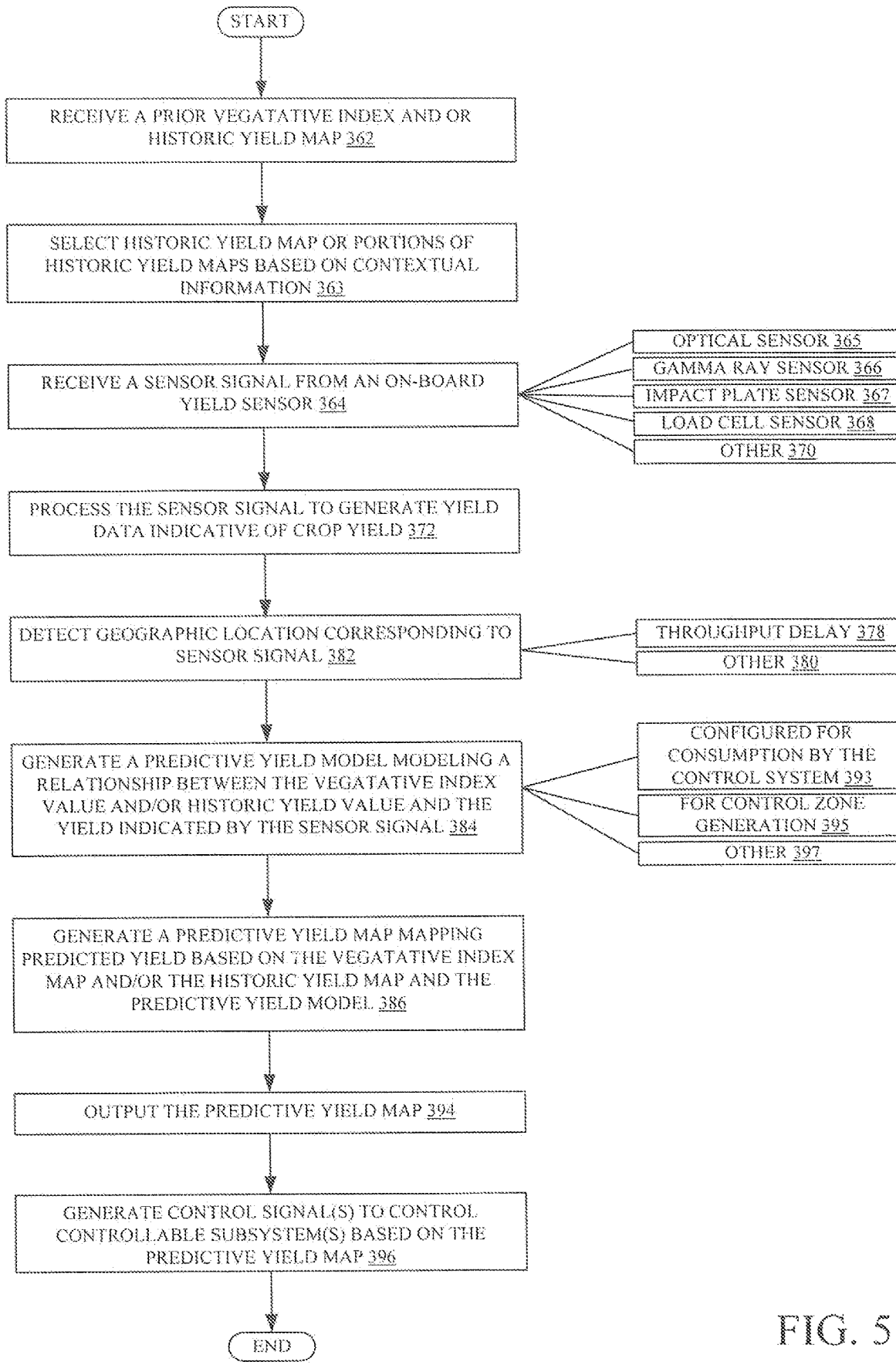
FIG. 5 is a flow diagram showing an example of operation of an agricultural harvester in receiving a vegetative index or historical yield map, detecting an in-situ yield characteristic, and generating a functional predictive yield map for presentation or use in controlling the agricultural harvester during a harvesting operation or both.

After the general approach is described with respect to FIGS. 2 and 3, a more specific approach for generating a functional predictive yield map that can be presented to an operator or user, or used to control agricultural harvester 100, or both is described with respect to FIGS. 4 and 5. Again, while the present discussion proceeds with respect to the agricultural harvester and, particularly, a combine harvester, the scope of the present disclosure encompasses other types of agricultural harvesters or other agricultural work machines.

FIG. 2 is a block diagram showing some portions of an example agricultural harvester 100. FIG. 2 shows that agricultural harvester 100 illustratively includes one or more processors or servers 201, data store 202, geographic position sensor 204, communication system 206, and one or more in-situ sensors 208 that sense one or more agricultural characteristics of a field concurrent with a harvesting operation. An agricultural characteristic can include any characteristic that can have an effect of the harvesting operation. Some examples of agricultural characteristics include characteristics of the harvesting machine, the field, the plants on the field, and the weather. Other types of agricultural characteristics are also included. The in-situ sensors 208 generate values corresponding to the sensed characteristics. The agricultural harvester 100 also includes a predictive model or relationship generator (collectively referred to hereinafter as "predictive model generator 210"), predictive map generator 212, control zone generator 213, control system 214, one or more controllable subsystems 216, and an operator interface mechanism 218. The agricultural harvester 100 can also include a wide variety of other agricultural harvester functionality 220. The in-situ sensors 208 include, for example, on-board sensors 222, remote sensors 224, and other sensors 226 that sense characteristics of a field during the course of an agricultural operation. Predictive model generator 210 illustratively includes a prior information variable-to-in-situ variable model generator 228, and predictive model generator 210 can include other items 230. Control system 214 includes communication system controller 229, operator interface controller 231, a settings controller 232, path planning controller 234, feed rate controller 236, header and reel controller 238, draper belt controller 240, deck plate position controller 242, residue system controller 244, machine cleaning controller 245, zone controller 247, and control system 214 can include other items 246. Controllable subsystems 216 include machine and header actuators 248, propulsion subsystem 250, steering subsystem 252, residue subsystem 138, machine cleaning subsystem 254, and controllable subsystems 216 can include a wide variety of other subsystems 256.

FIG. 2 also shows that agricultural harvester 100 can receive one or more prior information map(s) 258. As described below, the prior information map(s) include, for example, a vegetative index map or a vegetation map from a prior operation in the field. However, prior information map(s) 258 may also encompass other types of data that were obtained prior to a harvesting operation or a map from a prior operation, such as historical yield maps from past years that contain contextual information associated with the historical yield. Contextual information can include, without limitation, one or more of weather conditions over a growing season, presence of pests, geographic location, soil types, irrigation, treatment application, etc. Weather conditions can include, without limitation, precipitation over the season, presence of hail capable of crop damage, presence of high winds, temperature over the season, etc. Some examples of pests broadly include, insects, fungi, weeds, bacteria, viruses, etc. Some examples of treatment applications include herbicide, pesticide, fungicide, fertilizer, mineral supplements, etc. FIG. 2 also shows that an operator 260 may operate the agricultural harvester 100. The operator 260 interacts with operator interface mechanisms 218. In some examples, operator interface mechanisms 218 may include joysticks, levers, a steering wheel, linkages, pedals, buttons, dials, keypads, user actuatable elements (such as icons, buttons, etc.) on a user interface display device, a microphone and speaker (where speech recognition and speech synthesis are provided), among a wide variety of other types of control devices. Where a touch sensitive display system is provided, operator 260 may interact with operator interface mechanisms 218 using touch gestures. These examples described above are provided as illustrative examples and are not intended to limit the scope of the present disclosure. Consequently, other types of operator interface mechanisms 218 may be used and are within the scope of the present disclosure.

Prior information map 258 may be downloaded onto agricultural harvester 100 and stored in data store 202, using communication system 206 or in other ways. In some examples, communication system 206 may be a cellular communication system, a system for communicating over a wide area network or a local area network, a system for communicating over a near field communication network, or a communication system configured to communicate over any of a variety of other networks or combinations of networks. Communication system 206 may also include a system that facilitates downloads or transfers of information to and from a secure digital (SD) card or a universal serial bus (USB) card, or both.

Geographic position sensor 204 illustratively senses or detects the geographic position or location of agricultural harvester 100. Geographic position sensor 204 can include, but is not limited to, a global navigation satellite system (GNSS) receiver that receives signals from a GNSS satellite transmitter. Geographic position sensor 204 can also include a real-time kinematic (RTK) component that is configured to enhance the precision of position data derived from the GNSS signal. Geographic position sensor 204 can include a dead reckoning system, a cellular triangulation system, or any of a variety of other geographic position sensors.

In-situ sensors 208 may be any of the sensors described above with respect to FIG. 1. In-situ sensors 208 include on-board sensors 222 that are mounted on-board agricultural harvester 100. Such sensors may include, for instance, an impact plate sensor, a radiation attenuation sensor, or an image sensor that is internal to agricultural harvester 100 (such as a clean grain camera). The in-situ sensors 208 may also include remote in-situ sensors 224 that capture in-situ information. In-situ data include data taken from a sensor on-board the agricultural harvester or taken by any sensor where the data are detected during the harvesting operation.

After being retrieved by agricultural harvester 100, prior information map selector 209 can filter or select one or more specific prior information map(s) 258 for usage by predictive model generator 210. In one example, prior information map selector 209 selects a map based on a comparison of the contextual information in the prior information map versus the present contextual information. For example, a historical yield map may be selected from one of the past years where weather conditions over the growing season were similar to the present year's weather conditions. Or, for example, a historical yield map may be selected from one of the past years when the context information is not similar. For example, a historical yield map may be selected for a prior year that was "dry" (i.e., had drought conditions or reduced precipitation), while the present year is "wet" (i.e., had increased precipitation or flood conditions). There still may be a useful historical relationship, but the relationship may be inverse. For instance, areas that are flooded in a wet year may be areas of higher yield in a dry year because these areas may retain more water in dry years. Present contextual information may include contextual information beyond immediate contextual information. For instance, present contextual information can include, but not by limitation, a set of information corresponding to the present growing season, a set of data corresponding to a winter before the current growing season, or a set of data corresponding to several past years, amongst others.

The contextual information can also be used for correlations between areas with similar contextual characteristics, regardless of whether the geographic position corresponds to the same position on prior information map 258. For instance, historical yield values from area with similar soil types in other fields can be used as prior information map 258 to create the predictive yield map. For example, the contextual characteristic information associated with a different location may be applied to the location on the prior information map 258 having similar characteristic information.

Predictive model generator 210 generates a model that is indicative of a relationship between the values sensed by the in-situ sensor 208 and a characteristic mapped to the field by the prior information map 258. For example, if the prior information map 258 maps a vegetative index value to different locations in the field, and the in-situ sensor 208 is sensing a value indicative of yield, then prior information variable-to-in-situ variable model generator 228 generates a predictive yield model that models the relationship between the vegetative index values and the yield values. Then, predictive map generator 212 uses the predictive yield model generated by predictive model generator 210 to generate a functional predictive yield map that predicts the value of yield, at different locations in the field, based upon the prior information map 258. Or, for example, if the prior information map 258 maps a historical yield value to different locations in the field and the in-situ sensor 208 is sensing a value indicative of yield, then prior information variable-to-in-situ variable model generator 228 generates a predictive yield model that models the relationship between the historical yield values (with or without contextual information) and the in-situ yield values. Then, predictive map generator 212 uses the predictive yield model generated by predictive model generator 210 to generate a functional predictive yield map that predicts the value of yield that is expected be sensed by the in-situ sensors 208, at different locations in the field, based upon the prior information map 258.

In some examples, the type of data in the functional predictive map 263 may be the same as the in-situ data type sensed by the in-situ sensors 208. In some instances, the type of data in the functional predictive map 263 may have different units from the data sensed by the in-situ sensors 208. In some examples, the type of data in the functional predictive map 263 may be different from the data type sensed by the in-situ sensors 208 but has a relationship to data type sensed by the in-situ sensors 208. For example, in some examples, the in-situ data type may be indicative of the type of data in the functional predictive map 263. In some examples, the type of data in the functional predictive map 263 may be different than the data type in the prior information map 258. In some instances, the type of data in the functional predictive map 263 may have different units from the data in the prior information map 258. In some examples, the type of data in the functional predictive map 263 may be different from the data type in the prior information map 258 but has a relationship to the data type in the prior information map 258. For example, in some examples, the data type in the prior information map 258 may be indicative of the type of data in the functional predictive map 263. In some examples, the type of data in the functional predictive map 263 is different than one of, or both of the in-situ data type sensed by the in-situ sensors 208 and the data type in the prior information map 258. In some examples, the type of data in the functional predictive map 263 is the same as one of, or both of, of the in-situ data type sensed by the in-situ sensors 208 and the data type in prior information map 258. In some examples, the type of data in the functional predictive map 263 is the same as one of the in-situ data type sensed by the in-situ sensors 208 or the data type in the prior information map 258, and different than the other.

Continuing with the preceding vegetative index example, predictive map generator 212 can use the vegetative index values in prior information map 258 and the model generated by predictive model generator 210 to generate a functional predictive map 263 that predicts the yield at different locations in the field. Predictive map generator 212 thus outputs predictive map 264.

As shown in FIG. 2, predictive map 264 predicts the value of a characteristic, which may be the same characteristic sensed by in-situ sensor(s) 208, or a characteristic related to the characteristic sensed by the in-situ sensor(s) 208, at various locations across the field based upon a prior information value in prior information map 258 at those locations (or locations with similar contextual information, even if in a different field) and using the predictive model. For example, if predictive model generator 210 has generated a predictive model indicative of a relationship between a vegetative index value and yield, then, given the vegetative index value at different locations across the field, predictive map generator 212 generates a predictive map 264 that predicts the value of the yield at different locations across the field. The vegetative index value, obtained from the prior information map 258, at those locations and the relationship between vegetative index value and yield, obtained from the predictive model, are used to generate the predictive map 264.

Some variations in the data types that are mapped in the prior information map 258, the data types sensed by in-situ sensors 208 and the data types predicted on the predictive map 264 will now be described.

In some examples, the data type in the prior information map 258 is different from the data type sensed by in-situ sensors 208, yet the data type in the predictive map 264 is the same as the data type sensed by the in-situ sensors 208. For instance, the prior information map 258 may be a vegetative index map, and the variable sensed by the in-situ sensors 208 may be yield. The predictive map 264 may then be a predictive yield map that maps predicted yield values to different geographic locations in the field. In another example, the prior information map 258 may be a vegetative index map, and the variable sensed by the in-situ sensors 208 may be crop height. The predictive map 264 may then be a predictive crop height map that maps predicted crop height values to different geographic locations in the field.

Also, in some examples, the data type in the prior information map 258 is different from the data type sensed by in-situ sensors 208, and the data type in the predictive map 264 is different from both the data type in the prior information map 258 and the data type sensed by the in-situ sensors 208. For instance, the prior information map 258 may be a vegetative index map, and the variable sensed by the in-situ sensors 208 may be crop height. The predictive map 264 may then be a predictive biomass map that maps predicted biomass values to different geographic locations in the field. In another example, the prior information map 258 may be a vegetative index map, and the variable sensed by the in-situ sensors 208 may be yield. The predictive map 264 may then be a predictive speed map that maps predicted harvester speed values to different geographic locations in the field.

In some examples, the prior information map 258 is from a prior pass through the field during a prior operation and the data type is different from the data type sensed by in-situ sensors 208, yet the data type in the predictive map 264 is the same as the data type sensed by the in-situ sensors 208. For instance, the prior information map 258 may be a seed population map generated during planting, and the variable sensed by the in-situ sensors 208 may be stalk size. The predictive map 264 may then be a predictive stalk size map that maps predicted stalk size values to different geographic locations in the field. In another example, the prior information map 258 may be a seeding hybrid map, and the variable sensed by the in-situ sensors 208 may be crop state such as standing crop or down crop. The predictive map 264 may then be a predictive crop state map that maps predicted crop state values to different geographic locations in the field.

In some examples, the prior information map 258 is from a prior pass through the field during a prior operation and the data type is the same as the data type sensed by in-situ sensors 208, and the data type in the predictive map 264 is also the same as the data type sensed by the in-situ sensors 208. For instance, the prior information map 258 may be a yield map generated during a previous year, and the variable sensed by the in-situ sensors 208 may be yield. The predictive map 264 may then be a predictive yield map that maps predicted yield values to different geographic locations in the field. In such an example, the relative yield differences in the georeferenced prior information map 258 from the prior year can be used by predictive model generator 210 to generate a predictive model that models a relationship between the relative yield differences on the prior information map 258 and the yield values sensed by in-situ sensors 208 during the current harvesting operation. The predictive model is then used by predictive map generator 212 to generate a predictive yield map.

In another example, the prior information map 258 may be a weed intensity map generated during a prior operation, such as from a sprayer, and the variable sensed by the in-situ sensors 208 may be weed intensity. The predictive map 264 may then be a predictive weed intensity map that maps predicted weed intensity values to different geographic locations in the field. In such an example, a map of the weed intensities at time of spraying is geo-referenced recorded and provided to agricultural harvester 100 as a prior information map 258 of weed intensity. In-situ sensors 208 can detect weed intensity at geographic locations in the field and predictive model generator 210 may then build a predictive model that models a relationship between weed intensity at time of harvest and weed intensity at time of spraying. This is because the sprayer will have impacted the weed intensity at time of spraying, but weeds may still crop up in similar areas again by harvest. However, the weed areas at harvest are likely to have different intensity based on timing of the harvest, weather, weed type, among other things.

In some examples, predictive map 264 can be provided to the control zone generator 213. Control zone generator 213 groups adjacent portions of an area into one or more control zones based on data values of predictive map 264 that are associated with those adjacent portions. A control zone may include two or more contiguous portions of an area, such as a field, for which a control parameter corresponding to the control zone for controlling a controllable subsystem is constant. For example, a response time to alter a setting of controllable subsystems 216 may be inadequate to satisfactorily respond to changes in values contained in a map, such as predictive map 264. In that case, control zone generator 213 parses the map and identifies control zones that are of a defined size to accommodate the response time of the controllable subsystems 216. In another example, control zones may be sized to reduce wear from excessive actuator movement resulting from continuous adjustment. In some examples, there may be a different set of control zones for each controllable subsystem 216 or for groups of controllable subsystems 216. The control zones may be added to the predictive map 264 to obtain predictive control zone map 265. Predictive control zone map 265 can thus be similar to predictive map 264 except that predictive control zone map 265 includes control zone information defining the control zones. Thus, a functional predictive map 263, as described herein, may or may not include control zones. Both predictive map 264 and predictive control zone map 265 are functional predictive maps 263. In one example, a functional predictive map 263 does not include control zones, such as predictive map 264. In another example, a functional predictive map 263 does include control zones, such as predictive control zone map 265. In some examples, multiple crops may be simultaneously present in a field if an intercrop production system is implemented. In that case, predictive map generator and control zone generator 213 are able to identify the location and characteristics of the two or more crops and then generate predictive map 264 and predictive control zone map 265 accordingly.

It will also be appreciated that control zone generator 213 can cluster values to generate control zones and the control zones can be added to predictive control zone map 265, or a separate map, showing only the control zones that are generated. In some examples, the control zones may be used for controlling or calibrating agricultural harvester 100 or both. In other examples, the control zones may be presented to the operator 260 and used to control or calibrate agricultural harvester 100, and, in other examples, the control zones may be presented to the operator 260 or another user or stored for later use.

Predictive map 264 or predictive control zone map 265 or both are provided to control system 214, which generates control signals based upon the predictive map 264 or predictive control zone map 265 or both. In some examples, communication system controller 229 controls communication system 206 to communicate the predictive map 264 or predictive control zone map 265 or control signals based on the predictive map 264 or predictive control zone map to other agricultural harvesters that are harvesting in the same field. In some examples, communication system controller 229 controls the communication system 206 to send the predictive map 264, predictive control zone map 265, or both to other remote systems.

Operator interface controller 231 is operable to generate control signals to control operator interface mechanisms 218. The operator interface controller 231 is also operable to present the predictive map 264 or predictive control zone map 265 or other information derived from or based on the predictive map 264, predictive control zone map 265, or both to operator 260. Operator 260 may be a local operator or a remote operator. As an example, controller 231 generates control signals to control a display mechanism to display one or both of predictive map 264 and predictive control zone map 265 for the operator 260. Controller 231 may generate operator actuatable mechanisms that are displayed and can be actuated by the operator to interact with the displayed map. The operator can edit the map by, for example, correcting a yield value displayed on the map based on the operator's observation. Settings controller 232 can generate control signals to control various settings on the agricultural harvester 100 based upon predictive map 264, the predictive control zone map 265, or both. For instance, settings controller 232 can generate control signals to control machine and header actuators 248. In response to the generated control signals, the machine and header actuators 248 operate to control, for example, one or more of the sieve and chaffer settings, thresher clearance, rotor settings, cleaning fan speed settings, header height, header functionality, reel speed, reel position, draper functionality (where agricultural harvester 100 is coupled to a draper header), corn header functionality, internal distribution control, and other actuators 248 that affect the other functions of the agricultural harvester 100. Path planning controller 234 illustratively generates control signals to control steering subsystem 252 to steer agricultural harvester 100 according to a desired path. Path planning controller 234 can control a path planning system to generate a route for agricultural harvester 100 and can control propulsion subsystem 250 and steering subsystem 252 to steer agricultural harvester 100 along that route. Feed rate controller 236 can control various subsystems, such as propulsion subsystem and machine actuators 248, to control a feed rate based upon the predictive map 264 or predictive control zone map 265 or both. For instance, as agricultural harvester 100 approaches an area yielding above a selected threshold, feed rate controller 236 may reduce the speed of agricultural harvester 100 to maintain constant feed rate of grain or biomass through the machine. Header and reel controller 238 can generate control signals to control a header or a reel or other header functionality. Draper belt controller 240 can generate control signals to control a draper belt or other draper functionality based upon the predictive map 264, predictive control zone map 265, or both. Deck plate position controller 242 can generate control signals to control a position of a deck plate included on a header based on predictive map 264 or predictive control zone map 265 or both, and residue system controller 244 can generate control signals to control a residue subsystem 138 based upon predictive map 264 or predictive control zone map 265, or both. Machine cleaning controller 245 can generate control signals to control machine cleaning subsystem 254. For instance, based upon the different types of seeds or weeds passed through agricultural harvester 100, a particular type of machine cleaning operation or a frequency with which a cleaning operation is performed may be controlled. Other controllers included on the agricultural harvester 100 can control other subsystems based on the predictive map 264 or predictive control zone map 265 or both as well.

FIGS. 3A and 3B (collectively referred to herein as FIG. 3) show a flow diagram illustrating one example of the operation of agricultural harvester 100 in generating a predictive map 264 and predictive control zone map 265 based upon prior information map 258.

At 280, agricultural harvester 100 receives prior information map 258. Examples of prior information map 258 or receiving prior information map 258 are discussed with respect to blocks 281, 282, 284 and 286. As discussed above, prior information map 258 maps values of a variable, corresponding to a first characteristic, to different locations in the field, as indicated at block 282. For instance, one prior information map may be a seeding map generated during a prior operation or based on data from a prior operation on the field, such as prior seed planting operation performed by a seeder. The data for the prior information map 258 may be collected in other ways as well. For instance, the data may be collected based on aerial images or measured values taken during a previous year, or earlier in the current growing season, or at other times. The information may be based on data detected or gathered in other ways (other than using aerial images) as well. For instance, the data for the prior information map 258 can be transmitted to agricultural harvester 100 using communication system 206 and stored in data store 202. The data for the prior information map 258 can be provided to agricultural harvester 100 using communication system 206 in other ways as well, and this is indicated by block 286 in the flow diagram of FIG. 3. In some examples, the prior information map 258 can be received by communication system 206.

At block 287, prior information map selector 209 can select one or more maps from the plurality of candidate prior information maps received in block 280. For example, multiple years of historical yield maps may be received as candidate prior information maps. Each of these maps can contain contextual information such as weather patterns over a period of time, such as a year, pest surges over a period of time, such as a year, soil types, etc. Contextual information can be used to select which historical yield map should be selected. For instance, the weather conditions over a period of time, such in a current year, or the soil types for the current field can be compared to the weather conditions and soil type in the contextual information for each candidate prior information map. The results of such a comparison can be used to select which historical yield map should be selected. For example, years with similar weather conditions may generally produce similar yields or yield trends across a field. In some cases, years with opposite weather conditions may also be useful for predicting yield based on historical yield. For instance, an area with a high yield in a dry year, might have a low yield in a wet year as the area gets flooded. The process by which one or more prior information maps are selected by prior information map selector 209 can be manual, semi-automated or automated. In some examples, during a harvesting operation, prior information map selector 209 can continually or intermittently determine whether a different prior information map has a better relationship with the in-situ sensor value. If a different prior information map is correlating with the in-situ data more closely, then prior information map selector 209 can replace the currently selected prior information map with the more correlative prior information map.

Upon commencement of a harvesting operation, in-situ sensors 208 generate sensor signals indicative of one or more in-situ data values indicative of a plant characteristic, such as a yield, as indicated by block 288. Examples of in-situ sensors 288 are discussed with respect to blocks 222, 290, and 226. As explained above, the in-situ sensors 208 include on-board sensors 222; remote in-situ sensors 224, such as UAV-based sensors flown at a time to gather in-situ data, shown in block 290; or other types of in-situ sensors, designated by in-situ sensors 226. In some examples, data from on-board sensors is georeferenced using position heading or speed data from geographic position sensor 204.

Predictive model generator 210 controls the prior information variable-to-in-situ variable model generator 228 to generate a model that models a relationship between the mapped values contained in the prior information map 258 and the in-situ values sensed by the in-situ sensors 208 as indicated by block 292. The characteristics or data types represented by the mapped values in the prior information map 258 and the in-situ values sensed by the in-situ sensors 208 may be the same characteristics or data type or different characteristics or data types.

The relationship or model generated by predictive model generator 210 is provided to predictive map generator 212. Predictive map generator 212 generates a predictive map 264 that predicts a value of the characteristic sensed by the in-situ sensors 208 at different geographic locations in a field being harvested, or a different characteristic that is related to the characteristic sensed by the in-situ sensors 208, using the predictive model and the prior information map 258, as indicated by block 294.

It should be noted that, in some examples, the prior information map 258 may include two or more different maps or two or more different map layers of a single map. Each map layer may represent a different data type from the data type of another map layer or the map layers may have the same data type that were obtained at different times. Each map in the two or more different maps or each layer in the two or more different map layers of a map maps a different type of variable to the geographic locations in the field. In such an example, predictive model generator 210 generates a predictive model that models the relationship between the in-situ data and each of the different variables mapped by the two or more different maps or the two or more different map layers. Similarly, the in-situ sensors 208 can include two or more sensors each sensing a different type of variable. Thus, the predictive model generator 210 generates a predictive model that models the relationships between each type of variable mapped by the prior information map 258 and each type of variable sensed by the in-situ sensors 208. Predictive map generator 212 can generate a functional predictive map 263 that predicts a value for each sensed characteristic sensed by the in-situ sensors 208 (or a characteristic related to the sensed characteristic) at different locations in the field being harvested using the predictive model and each of the maps or map layers in the prior information map 258.

Predictive map generator 212 configures the predictive map 264 so that the predictive map 264 is actionable (or consumable) by control system 214. Predictive map generator 212 can provide the predictive map 264 to the control system 214 or to control zone generator 213 or both. Some examples of different ways in which the predictive map 264 can be configured or output are described with respect to blocks 296, 295, 299 and 297. For instance, predictive map generator 212 configures predictive map 264 so that predictive map 264 includes values that can be read by control system 214 and used as the basis for generating control signals for one or more of the different controllable subsystems of the agricultural harvester 100, as indicated by block 296.

Control zone generator 213 can divide the predictive map 264 into control zones based on the values on the predictive map 264. Contiguously-geolocated values that are within a threshold value of one another can be grouped into a control zone. The threshold value can be a default threshold value, or the threshold value can be set based on an operator input, based on an input from an automated system or based on other criteria. A size of the zones may be based on a responsiveness of the control system 214, the controllable subsystems 216, or based on wear considerations, or on other criteria as indicated by block 295. Predictive map generator 212 configures predictive map 264 for presentation to an operator or other user. Control zone generator can configure predictive control zone map 265 for presentation to an operator or other user. This is indicated by block 299. When presented to an operator or other user, the presentation of the predictive map 264 or predictive control zone map 265 or both may contain one or more of the predictive values on the predictive map 264 correlated to geographic location, the control zones on predictive control zone map 265 correlated to geographic location, and settings values or control parameters that are used based on the predicted values on predictive map 264 or zones on predictive control zone map 265. The presentation can, in another example, include more abstracted information or more detailed information. The presentation can also include a confidence level that indicates an accuracy with which the predictive values on predictive map 264 or the zones on predictive control zone map 265 conform to measured values that may be measured by sensors on agricultural harvester 100 as agricultural harvester 100 moves through the field. Further where information is presented to more than one location, an authentication/authorization system can be provided to implement authentication and authorization processes. For instance, there may be a hierarchy of individuals that are authorized to view and change maps and other presented information. By way of example, an on-board display device may show the maps in near real time locally on the machine, only, or the maps may also be generated at one or more remote locations. In some examples, each physical display device at each location may be associated with a person or a user permission level. The user permission level may be used to determine which display markers are visible on the physical display device, and which values the corresponding person may change. As an example, a local operator of agricultural harvester 100 may be unable to see the information corresponding to the predictive map 264 or make any changes to machine operation. A supervisor, at a remote location, however, may be able to see the predictive map 264 on the display, but not make changes. A manager, who may be at a separate remote location, may be able to see all of the elements on predictive map 264 and also change the predictive map 264 that is used in machine control. This is one example of an authorization hierarchy that may be implemented. The predictive map 264 or predictive control zone map 265 or both can be configured in other ways as well, as indicated by block 297.

At block 298, input from geographic position sensor 204 and other in-situ sensors 208 are received by the control system. Block 300 represents receipt by control system 214 of an input from the geographic position sensor 204 identifying a geographic location of agricultural harvester 100. Block 302 represents receipt by the control system 214 of sensor inputs indicative of trajectory or heading of agricultural harvester 100, and block 304 represents receipt by the control system 214 of a speed of agricultural harvester 100. Block 306 represents receipt by the control system 214 of other information from various in-situ sensors 208.

At block 308, control system 214 generates control signals to control the controllable subsystems 216 based on the predictive map 264 or predictive control zone map 265 or both and the input from the geographic position sensor 204 and any other in-situ sensors 208. At block 310, control system 214 applies the control signals to the controllable subsystems. It will be appreciated that the particular control signals that are generated, and the particular controllable subsystems 216 that are controlled, may vary based upon one or more different things. For example, the control signals that are generated and the controllable subsystems 216 that are controlled may be based on the type of predictive map 264 or predictive control zone map 265 or both that is being used. Similarly, the control signals that are generated and the controllable subsystems 216 that are controlled and the timing of the control signals can be based on various latencies of crop flow through the agricultural harvester 100 and the responsiveness of the controllable subsystems 216.

By way of example, a generated predictive map 264 in the form of a predictive yield map can be used to control one or more controllable subsystems 216. For example, the functional predictive yield map can include yield values georeferenced to locations within the field being harvested. The functional predictive yield map can be extracted and used to control the steering and propulsion subsystems 252 and 250. By controlling the steering and propulsion subsystems 252 and 250, a feed rate of material or grain moving through the agricultural harvester 100 can be controlled. Similarly, the header height can be controlled to take in more or less material and thus the header height can also be controlled to control feed rate of material through the agricultural harvester 100. In other examples, if the predictive map 264 maps a yield forward of the machine being higher on one portion of the header than another portion of the header, resulting in a different biomass entering one side of the header than the other side, control of the header may be implemented. For example, a draper speed on one side of the header may be increased or decreased relative to the draper speed other side of the header to account for the additional biomass. Thus, the header and reel controller 238 can be controlled using georeferenced values present in the predictive yield map to control draper speeds of the draper belts on the header. The preceding example involving feed rate and header control using a functional predictive yield map is provided merely as an example. Consequently, a wide variety of other control signals can be generated using values obtained from a predictive yield map or other type of functional predictive map to control one or more of the controllable subsystems 216.

At block 312, a determination is made as to whether the harvesting operation has been completed. If harvesting is not completed the processing advances to block 314 where in-situ sensor data from geographic position sensor 204 and in-situ sensors 208 (and perhaps other sensors) continue to be read.

In some examples, at block 316, agricultural harvester 100 can also detect learning trigger criteria to perform machine learning on one or more of the predictive map 264, predictive control zone map 265, the model generated by predictive model generator 210, the zones generated by control zone generator 213, one or more control algorithms implemented by the controllers in the control system 214, and other triggered learning.

The learning trigger criteria can include any of a wide variety of different criteria. Some examples of detecting trigger criteria are discussed with respect to blocks 318, 320, 321, 322 and 324. For instance, in some examples, triggered learning can involve recreation of a relationship used to generate a predictive model when a threshold amount of in-situ sensor data are obtained from in-situ sensors 208. In such examples, receipt of an amount of in-situ sensor data from the in-situ sensors 208 that exceeds a threshold triggers or causes the predictive model generator 210 to generate a new predictive model that is used by predictive map generator 212. Thus, as agricultural harvester 100 continues a harvesting operation, receipt of the threshold amount of in-situ sensor data from the in-situ sensors 208 triggers the creation of a new relationship represented by a predictive model generated by predictive model generator 210. Further, new predictive map 264, predictive control zone map 265, or both can be regenerated using the new predictive model. Block 318 represents detecting a threshold amount of in-situ sensor data used to trigger creation of a new predictive model.

In other examples, the learning trigger criteria may be based on how much the in-situ sensor data from the in-situ sensors 208 are changing, such as over time or compared to previous values. For example, if variations within the in-situ sensor data (or the relationship between the in-situ sensor data and the information in prior information map 258) are within a selected range or is less than a defined amount or is below a threshold value, then a new predictive model is not generated by the predictive model generator 210. As a result, the predictive map generator 212 does not generate a new predictive map 264, predictive control zone map 265, or both. However, if variations within the in-situ sensor data are outside of the selected range, are greater than the defined amount, or are above the threshold value, for example, then the predictive model generator 210 generates a new predictive model using all or a portion of the newly received in-situ sensor data that the predictive map generator 212 uses to generate a new predictive map 264. At block 320, variations in the in-situ sensor data, such as a magnitude of an amount by which the data exceeds the selected range or a magnitude of the variation of the relationship between the in-situ sensor data and the information in the prior information map 258, can be used as a trigger to cause generation of a new predictive model and predictive map. Keeping with the examples described above, the threshold, the range, and the defined amount can be set to default values; set by an operator or user interaction through a user interface; set by an automated system; or set in other ways.

Other learning trigger criteria can also be used. For instance, if predictive model generator 210 switches to a different prior information map (different from the originally selected prior information map 258), then switching to the different prior information map may trigger re-learning by predictive model generator 210, predictive map generator 212, control zone generator 213, control system 214, or other items. In another example, transitioning of agricultural harvester 100 to a different topography or to a different control zone may be used as learning trigger criteria as well.

In some instances, operator 260 can also edit the predictive map 264 or predictive control zone map 265 or both. The edits can change a value on the predictive map 264; change a size, shape, position, or existence of a control zone on predictive control zone map 265; or both. Block 321 shows that edited information can be used as learning trigger criteria.

In some instances, it may also be that operator 260 observes that automated control of a controllable subsystem, is not what the operator desires. In such instances, the operator 260 may provide a manual adjustment to the controllable subsystem reflecting that the operator 260 desires the controllable subsystem to operate in a different way than is being commanded by control system 214. Thus, manual alteration of a setting by the operator 260 can cause one or more of predictive model generator 210 to relearn a model, predictive map generator 212 to regenerate map 264, control zone generator 213 to regenerate one or more control zones on predictive control zone map 265, and control system 214 to relearn a control algorithm or to perform machine learning on one or more of the controller components 232 through 246 in control system 214 based upon the adjustment by the operator 260, as shown in block 322. Block 324 represents the use of other triggered learning criteria.

In other examples, relearning may be performed periodically or intermittently based, for example, upon a selected time interval such as a discrete time interval or a variable time interval, as indicated by block 326.

If relearning is triggered, whether based upon learning trigger criteria or based upon passage of a time interval, as indicated by block 326, then one or more of the predictive model generator 210, predictive map generator 212, control zone generator 213, and control system 214 performs machine learning to generate a new predictive model, a new predictive map, a new control zone, and a new control algorithm, respectively, based upon the learning trigger criteria. The new predictive model, the new predictive map, and the new control algorithm are generated using any additional data that has been collected since the last learning operation was performed. Performing relearning is indicated by block 328.

If the harvesting operation has been completed, operation moves from block 312 to block 330 where one or more of the predictive map 264, predictive control zone map 265, and predictive model generated by predictive model generator 210 are stored. The predictive map 264, predictive control zone map 265, and predictive model may be stored locally on data store 202 or sent to a remote system using communication system 206 for later use.

It will be noted that while some examples herein describe predictive model generator 210 and predictive map generator 212 receiving a prior information map in generating a predictive model and a functional predictive map, respectively, in other examples, the predictive model generator 210 and predictive map generator 212 can receive, in generating a predictive model and a functional predictive map, respectively other types of maps, including predictive maps, such as a functional predictive map generated during the harvesting operation.

FIG. 4 is a block diagram of a portion of the agricultural harvester 100 shown in FIG. 1. Particularly, FIG. 4 shows, among other things, examples of the predictive model generator 210 and the predictive map generator 212 in more detail. FIG. 4 also illustrates information flow among the various components shown therein. As shown, the predictive model generator 210 receives one or more of a vegetative index map 332 or a historical yield map 333 as a prior information map. Historical yield map 333 includes historical yield values 335 indicative of yield values across the field during a past harvest. Historical yield map 333 also includes contextual data 337 that is indicative of the context or conditions that may have influenced the yield value for the past year(s). For example, contextual data 337 can include soil type, elevation, slope, plant date, harvest date, fertilizer application, seed type (hybrids, etc.), a measure of weed presence, a measure of pest presence, weather conditions, e.g., rainfall, snow coverage, hail, wind, temperature, etc. Historical yield map 333 can include other items as well, as indicated by block 339. As shown in the illustrated example, vegetative index map 332 does not contain additional information. However in other examples, vegetative index map 332 can include other items as well. For instance, weed growth has an effect on a vegetative index reading. Consequently, herbicide application in temporal relation to the vegetative index sensing used to generate vegetative index map 332 may be contextual information included in the vegetative index map 332 to provide context to the vegetative index values.

Besides receiving one or more of a vegetative index map 332 or a historical yield map 333 as a prior information map, predictive model generator 210 also receives a geographic location indicator 334, or an indication of a geographic location, from geographic position sensor 204. In-situ sensors 208 illustratively include an on-board yield sensor 336 as well as a processing system 338. The processing system 338 processes sensor data generated from the on-board yield sensors 336.

In some examples, on-board yield sensor 336 may be an optical sensor on agricultural harvester 100. In some instances, the optical sensor may be a camera or other device that performs optical sensing. The optical sensor may be arranged in grain tank 132 to collect images of the storage area of grain tank 132 as agricultural harvester 100 moves through the field during a harvesting operation. Processing system 338 processes one or more images obtained via the on-board yield sensor 336 to generate processed image data identifying one or more characteristics of grain in the image. Grain characteristics detected by the processing system 338 may include one or more of volume, shape, and orientation of harvested grain in tank 132 over time, which is indicative of the harvested grain yield. Processing system 338 can also geolocate the values received from the in-situ sensor 208. For example, the location of the agricultural harvester at the time a signal from in-situ sensor 208 is received is typically not the accurate location of the yield. This is because an amount of time elapses between when the agricultural harvester makes initial contact with the plant and when the grain from the plant is processed by the agricultural harvester or when the processed grain is delivered to a storage location on the agricultural harvester. Thus, a transient time between when a plant is initially encountered and when grain from the plant is sensed within the agricultural harvester is taken into account when georeferencing the sensed data. By doing so, an accurate yield measurement can be sensed. Due to travel of severed crop along a header in a direction that is transverse to a direction of travel of the agricultural harvester, the yield values normally geolocate to a chevron shape area rearward of the agricultural harvester as the agricultural harvester travels in a forward direction.

Processing system 338 allocates or apportions an aggregate yield detected by a yield sensor during each time or measurement interval back to earlier geo-referenced regions based upon the travel times of the crop from different portions of the agricultural harvester, such as different lateral locations along a width of a header of the agricultural harvester. For example, processing system 338 allocates a measured aggregate yield from a measurement interval or time back to geo-referenced regions that were traversed by a header of the agricultural harvester during different measurement intervals or times. The processing system 338 apportions or allocates the aggregate yield from a particular measurement interval or time to previously traversed geo-referenced regions which are part of the chevron shape area.

In other examples, on-board yield sensor 336 can rely on different types of radiation and the way in which radiation is reflected by, absorbed by, attenuated by, or transmitted through the biomass or the harvested grain. The yield sensor 336 may sense other electromagnetic properties of grain and biomass such as electrical permittivity when the material passes between two capacitive plates. The yield sensor 336 may also rely on mechanical properties of grains and biomass such as a signal generated when a grain impacts a piezoelectric sheet or when the impact is detected by a microphone or accelerometer. Other material properties and sensors may also be used. In some examples, raw or processed data from on-board yield sensor 336 may be presented to operator 260 via operator interface mechanism 218. Operator 260 may be onboard of the work agricultural harvester 100 or at a remote location.

The present discussion proceeds with respect to an example in which on-board yield sensor 336 is an impact plate sensor. It will be appreciated that this is merely one example, and the sensors mentioned above, as other examples of on-board yield sensor 336, are contemplated herein as well. As shown in FIG. 4, the predictive model generator 210 includes a vegetative index-to-yield model generator 342, and a historical yield-to-yield model generator 344. In other examples, the predictive model generator 210 may include additional, fewer, or different components than those shown in the example of FIG. 4. Consequently, in some examples, the predictive model generator 210 may include other items 348 as well, which may include other types of predictive model generators to generate other types of yield models.

Model generator 342 identifies a relationship between in-situ yield data 340 at a geographic location corresponding to where in-situ yield data 340 was geolocated and vegetative index values from the vegetative index map 332 corresponding to the same location in the field where yield data 340 was geolocated. Based on this relationship established by model generator 342, model generator 342 generates a predictive yield model. The yield model is used by predictive map generator 212 to predict a yield at different locations in the field based upon the georeferenced vegetative index value contained in the vegetative index map 332 at the same locations in the field.

Model generator 344 identifies a relationship between the yield represented in the yield data 340, at a geographic location corresponding to where the yield data 340 was geolocated, and the historical yield at the same location (or a location in a historical yield map 333 with similar contextual data 337 as the present area or year). The historical yield value 335 is the georeferenced and contextually-referenced value contained in the historical yield map 333. Model generator 344 then generates a predictive yield model that is used by map generator 212 to predict the yield at a location in the field based upon the historical yield value.

In light of the above, the predictive model generator 210 is operable to produce a plurality of predictive yield models, such as one or more of the predictive yield models generated by model generators 342 and 344. In another example, two or more of the predictive yield models described above may be combined into a single predictive yield model that predicts a yield based upon the vegetative index value or the historical yield at different locations in the field or both. Any of these yield models, or combinations thereof, are represented collectively by yield model 350 in FIG. 4.

The predictive yield model 350 is provided to predictive map generator 212. In the example of FIG. 4, predictive map generator 212 includes a yield map generator 352. In other examples, the predictive map generator 212 may include additional, fewer, or different map generators. Yield map generator 352 receives the predictive yield model 350 that predicts yield based upon in-situ data 340 along with one or both of the vegetative index map 332 and historical yield map 333.

Yield map generator 352 can generate a functional predictive yield map 360 that predicts yield at different locations in the field based upon the vegetative index value or historical yield value at those locations in the field and the predictive yield model 350. The generated functional predictive yield map 360 may be provided to control zone generator 213, control system 214, or both. Control zone generator 213 generates control zones and incorporates those control zones into the functional predictive map 360. Functional predictive map 360 may be presented to the operator 260 or anther user or be provided to control system 214, which generates control signals to control one or more of the controllable subsystems 216 based upon the functional predictive map 360.

FIG. 5 is a flow diagram of an example of operation of predictive model generator 210 and predictive map generator 212 in generating the predictive yield model 350 and the functional predictive yield map 360. At block 362, predictive model generator 210 and predictive map generator 212 receive one or more prior vegetative index maps 332 or one or more historical yield maps 333 or both. At block 362, a yield sensor signal is received from an on-board yield sensor 336. As discussed above, the on-board yield sensor 336 may be an optical sensor 365 in grain tank 132 or elsewhere, a gamma ray attenuation sensor 366, an impact plate sensor 367, load cells 368, or other yield sensor 370.

At block 363, prior information map selector 209 selects one or more specific prior information map(s) 250 for use by predictive model generator 210. In one example, prior information map selector 209 selects a map from a plurality of candidate maps based on a comparison of the contextual information in the candidate maps with the current contextual information. For example, a candidate historical yield map may be selected from a prior year in which weather conditions over the growth season were similar to the present year's weather conditions. Or, for example, a candidate historical yield map may be selected from a prior year having a below average level of precipitation, while the present year has an average or above average level of precipitation, because the historical yield map associated with a previous year with below average precipitation may still have a useful historical yield-yield relationship, as discussed above. In some examples, prior information map selector 209 can change which prior information map is being used upon detection that one of the other candidate prior information maps is more closely correlating to the in-situ sensed yield.

At block 372, processing system 338 processes the one or more received sensor signals received from the on-board yield sensors 336 to generate a yield value indicative of a yield characteristic of the harvested grain.

At block 382, predictive model generator 210 also obtains the geographic location corresponding to the sensor signal. For instance, the predictive model generator 210 can obtain the geographic position from geographic position sensor 204 and determine, based upon machine delays (e.g., machine processing speed) and machine speed, an accurate geographic location where the in-situ sensed crop yield is to be attributed. For example, the exact time a yield sensor signal is captured typically does not correspond to a time when the crop was severed from the ground. Thus, a position of the agricultural harvester 100 when the yield sensor signal is obtained does not correspond to the location where the crop was planted. Instead, the current in-situ yield sensor signal corresponds to a location on the field reward of agricultural harvester 100 since an amount of time transpires between when initial contact between the crop and the agricultural harvester occurs and when the crop reaches yield sensor 336.

At block 384, predictive model generator 210 generates one or more predictive yield models, such as yield model 350, that model a relationship between at least one of a vegetative index value or historical yield value obtained from a prior information map, such as prior information map 258, and a yield being sensed by the in-situ sensor 208. For instance, predictive model generator 210 may generate a predictive yield model based on a historical yield value and a sensed yield indicated by the sensor signal obtained from in-situ sensor 208.

At block 386, the predictive yield model, such as predictive yield model 350, is provided to predictive map generator 212 which generates a functional predictive yield map that maps a predicted yield to different geographic locations in the field based on the vegetative index map or historical yield map and the predictive yield model 350. For instance, in some examples, the functional predictive yield map 360 predicts yield. In other examples, the functional predictive yield map 360 map predicts other items, as indicated by block 392. Further, the functional predictive yield map 360 can be generated during the course of an agricultural harvesting operation. Thus, as an agricultural harvester is moving through a field performing an agricultural harvesting operation, the functional predictive yield map 360 is generated.

At block 394, predictive map generator 212 outputs the functional predictive yield map 360. At block 393, predictive map generator 212 configures the functional predictive yield map 360 for consumption by control system 214. At block 395, predictive map generator 212 can also provide the map 360 to control zone generator 213 for generation of control zones. At block 397, predictive map generator 212 configures the map 360 in other ways as well. The functional predictive yield map 360 (with or without the control zones) is provided to control system 214. At block 396, control system 214 generates control signals to control the controllable subsystems 216 based upon the functional predictive yield map 360.

It can thus be seen that the present system takes a prior information map that maps a characteristic such as a vegetative index value or historical yield values to different locations in a field. The present system also uses one or more in-situ sensors that sense in-situ sensor data that is indicative of a characteristic, such as yield, and generates a model that models a relationship between the yield sensed in-situ using the in-situ sensor and the characteristic mapped in the prior information map. Thus, the present system generates a functional predictive map using a model and a prior information map and may configure the generated functional predictive map for consumption by a control system or for presentation to a local or remote operator or other user. For example, the control system may use the map to control one or more systems of a combine harvester.

Figure 6A:
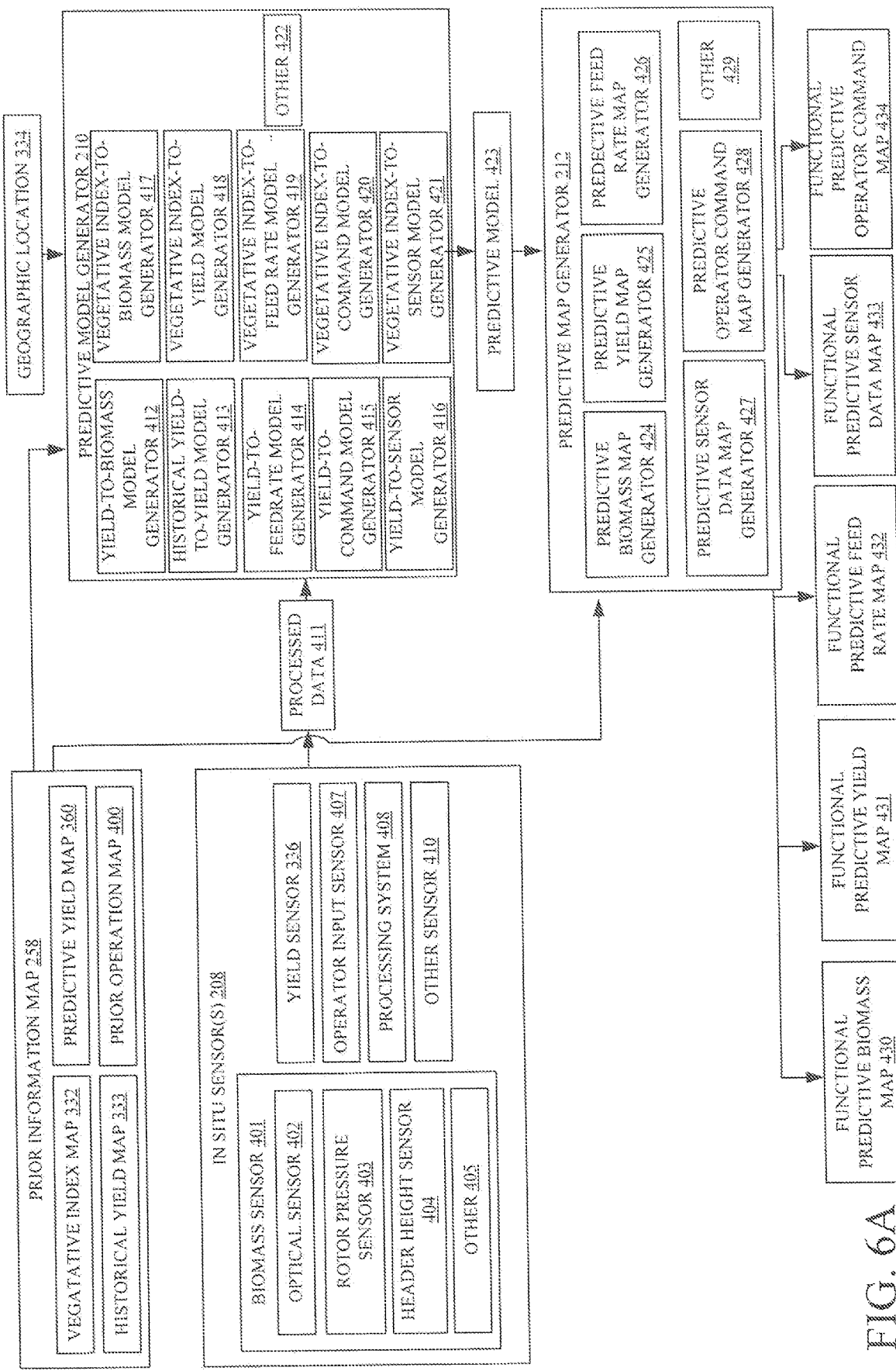
FIG. 6A is a block diagram showing one example of a predictive model generator and a predictive map generator.

FIG. 6A is a block diagram of an example portion of the agricultural harvester 100 shown in FIG. 1. Particularly, FIG. 6A shows, among other things, examples of predictive model generator 210 and predictive map generator 212. In the illustrated example, the prior information map 258 is one or more of a vegetative index map 332, a historical yield map 333, a predictive yield map 360, or a prior operation map 400.

Figure 6B:
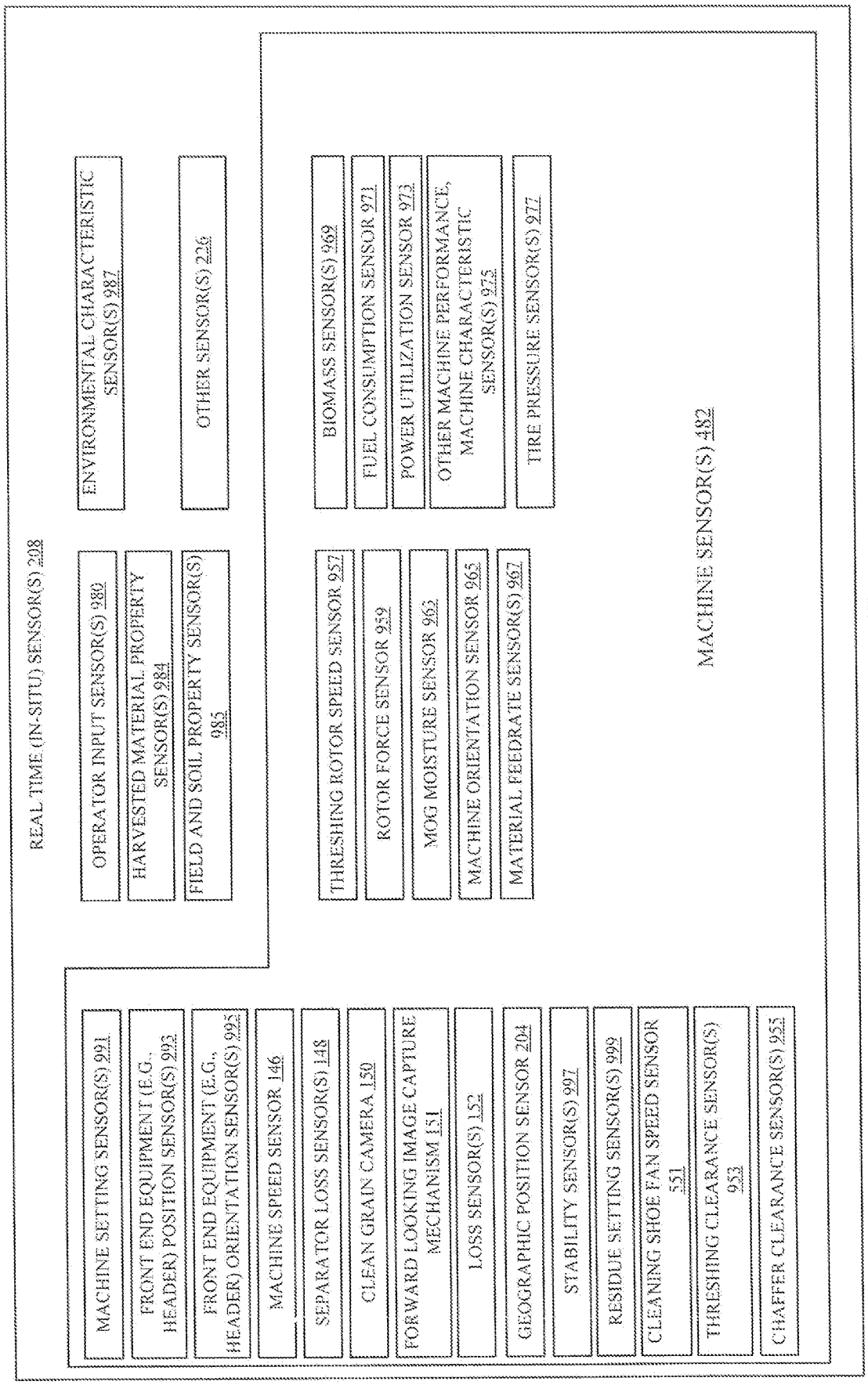
FIG. 6B is a block diagram showing some examples of in-situ sensors.

Also, in the example shown in FIG. 6A, in-situ sensor 208 can include one or more biomass sensors 401, yield sensor 336, an operator input sensor 407, and a processing system 408. In-situ sensors 208 can include other sensors 410 as well. Some examples of these other sensors are shown in FIG. 6B.

Biomass sensor 401 senses a variable indicative of the biomass of material being processed by agricultural harvester 100. In some examples, biomass sensor 401 can be an optical sensor 402, such as one of the optical sensors or cameras discussed above. In some examples, biomass sensor 401 can be a rotor pressure sensor 412 or another sensor 414. Rotor pressure sensor may sense the rotor drive pressure of a threshing rotor 112. The rotor drive pressure of threshing rotor 112 is indicative of the torque exerted by rotor 112 on the material being processed by agricultural harvester 100. As the biomass of material being processed by agricultural harvester 100 increases, the rotor drive pressure increases as well. Therefore, by sensing the rotor drive pressure, an indication of the biomass of material being processed can be obtained. Moisture sensor senses a variable indicative of the moisture of material being processed by, or proximate agricultural harvester 100. In some examples, biomass sensor 401 can include a crop height sensor 404 or another sensor 405.

Operator input sensor 407 illustratively senses various operator inputs. The inputs can be setting inputs for controlling the settings on agricultural harvester 100 or other control inputs, such as steering inputs and other inputs. Thus, when operator 260 changes a setting or provides a commanded input through an operator interface mechanism 218, such an input is detected by operator input sensor 407, which provides a sensor signal indicative of that sensed operator input.

Processing system 408 may receive the sensor signals from biomass sensor 401 or operator input sensor 407 or both and generate an output indicative of the sensed variable. For instance, processing system 408 may receive a sensor input from optical sensor 402 or rotor pressure sensor 403 and generate an output indicative of biomass. Processing system 408 may also receive an input from operator input sensor 407 and generate an output indicative of the sensed operator input.

Predictive model generator 210 may include yield-to-biomass model generator 412, historical yield-to-yield model generator 413, yield-to-feed rate model generator 414, yield-to-command model generator 415, yield-to-sensor model generator 416, vegetative index-to-biomass model generator 417, vegetative index-to-yield model generator 418, vegetative index-to-feed rate model generator 419, vegetative index-to-command model generator 420, and vegetative index-to-sensor model generator 421. In other examples, predictive model generator 210 can include additional, fewer, or other model generators 422. Predictive model generator 210 may receive a geographic location 334 from geographic position sensor 204 (shown in FIG. 2) and generate a predictive model 423 that models a relationship between the information in one or more of the prior information maps 258 and one or more of: the biomass sensed by biomass sensor 401; the yield sensed by yield sensor 336; and operator input commands sensed by operator input sensor 407.

For instance, yield-to-biomass model generator 412 generates a relationship between a yield as reflected on historical yield map 333, predictive yield map 360, the prior operation map 400, or any combination thereof and the biomass values sensed by biomass sensor 401. Historical yield-to-yield model generator 413 illustratively generates a model that represents a relationship between the historical yield (from historical yield map 333) and the yield sensed by yield sensor 336.

Yield-to-feed rate model generator 414 illustratively generates a model that represents a relationship between a yield as reflected on historical yield map 333, predictive yield map 360, the prior operation map 400, or any combination thereof and the feed rate or variable indicative of feed rate sensed by an in-situ sensor 208.

Yield-to-operator command model generator 415 generates a model that models the relationship between a yield as reflected on historical yield map 333, predictive yield map 360, the prior operation map 400, or any combination thereof and operator input commands that are sensed by operator input sensor 407.

Yield-to-sensor model generator 416 generates a relationship between a yield as reflected on historical yield map 333, predictive yield map 360, the prior operation map 400, or any combination thereof and the values sensed by other sensors 410.

Vegetative index-to-biomass model generator 417 generates a relationship between vegetative index values from vegetative index map 332 and the biomass values sensed by biomass sensor 401.

Vegetative index-to-yield model generator 418 illustratively generates a model that represents a relationship between the vegetative index value from vegetative index map 332 and the yield sensed by yield sensor 336.

Vegetative index-to-feed rate model generator 419 illustratively generates a model that represents a relationship between the vegetative index values from vegetative index map 332 and the feed rate sensed by an in-situ sensor 208.

Vegetative index-to-operator command model generator 420 generates a model that models the relationship between a vegetative index as reflected on vegetative index map 332 and operator input commands that are sensed by operator input sensor 407.

Vegetative index-to-sensor model generator 421 generates a relationship between vegetative index values from vegetative index map 332 and the values sensed by other sensors 410.

Predictive model 423 generated by the predictive model generator 210 can include one or more of the predictive models that may be generated by yield-to-biomass model generator 412, historical yield-to-yield model generator 413, yield-to-feed rate model generator 414, yield-to-command model generator 415, yield-to-sensor model generator 416, vegetative index-to-biomass model generator 417, vegetative index-to-yield model generator 418, vegetative index-to-feed rate model generator 419, vegetative index-to-command model generator 420, and vegetative index-to-sensor model generator 421, and other model generators that may be included as part of other items 422.

In the example of FIG. 6, predictive map generator 212 includes predictive biomass map generator 424, predictive yield map generator 425, predictive feed rate map generator 426, predictive sensor data map generator 427, and a predictive operator command map generator 428. In other examples, predictive map generator 212 can include additional, fewer, or other map generators 429.

Predictive biomass map generator 424 receives a predictive model 423 that models the relationship between a yield or vegetative index and biomass (such as a predictive model generated by yield-to-biomass model generator 412 or vegetative index-to-biomass model generator 417), and one or more of the prior information maps 258. Predictive biomass map generator 424 generates a functional predictive biomass map 430 that predicts biomass at different locations in the field based upon one or more of the yield and vegetative index in one or more of the prior information maps 258 at those locations in the field and based on predictive model 423.

Predictive yield map generator 425 receives a predictive model 423 that models the relationship between a historical yield or vegetative index and yield (such as a predictive model generated by historical yield-to-yield model generator 413 or vegetative index-to-yield model generator 418), and one or more of the prior information maps 258. Predictive yield map generator 425 generates a functional predictive yield map 431 that predicts yield at different locations in the field based upon one or more of the historical yield and vegetative index in one or more of the prior information maps 258 at those locations in the field and based on predictive model 423.

Predictive feed rate map generator 426 receives a predictive model 423 that models the relationship between a yield or vegetative index and feed rate (such as a predictive model generated by yield-to-feed rate model generator 414 or vegetative index-to-feed rate model generator 419), and one or more of the prior information maps 258. Predictive feed rate map generator 426 generates a functional predictive feed rate map 432 that predicts desirable feed rates at different locations in the field based upon one or more of the yield and vegetative index in one or more of the prior information maps 258 at those locations in the field and based on predictive model 423.

Predictive operator command map generator 427 receives a predictive model 423 (such as a predictive model generated by yield-to-command model generator 415 or vegetative index-to-command model generator 420), that models the relationship between the yield or vegetative index and operator command inputs detected by operator input sensor 407 and generates a functional predictive operator command map 434 that predicts operator command inputs at different locations in the field based upon one or more of the yield and vegetative index in one or more of the prior information maps 258 at those locations in the field and based on predictive model 423.

Predictive sensor data map generator 427 receives a predictive model 423 that models the relationship between a yield or vegetative index and sensor data (such as a predictive model generated by yield-to-sensor data model generator 413 or vegetative index-to-sensor model generator 421), and one or more of the prior information maps 258. Predictive yield map generator 425 generates a functional predictive sensor data map 433 that predicts sensor data at different locations in the field based upon one or more of the yield and vegetative index values in one or more of the prior information maps 258 at those locations in the field and based on predictive model 423.

Predictive map generator 212 outputs one or more of the functional predictive maps 430, 431, 432, 433, and 434. Each of the functional predictive maps 430, 431, 432, 433, and 434 may be provided to control zone generator 213, control system 214, or both. Control zone generator 213 generates control zones and incorporates those control zones into the functional predictive maps 430, 431, 432, 433, and 434. Any or all of functional predictive maps 430, 431, 432, 433, or 434 and the corresponding functional predictive maps 430, 431, 432, 433, or 434 having control zones may be provided to control system 214, which generates control signals to control one or more of the controllable subsystems 216 based upon one or all of the functional predictive maps. Any or all of the maps 430, 431, 432, 433, or 434 (with or without control zones) may be presented to operator 260 or another user.

FIG. 6B is a block diagram showing some examples of real-time (in-situ) sensors 208. Some of the sensors shown in FIG. 6B, or different combinations of them, may have both a sensor 336 and a processing system 338. Some of the possible in-situ sensors 208 shown in FIG. 6B are shown and described above with respect to previous FIGS. and are similarly numbered. FIG. 6B shows that in-situ sensors 208 can include operator input sensors 980, machine sensors 982, harvested material property sensors 984, field and soil property sensors 985, environmental characteristic sensors 987, and they may include a wide variety of other sensors 226. Operator input sensors 980 may be sensors that sense operator inputs through operator interface mechanisms 218. Therefore, operator input sensors 980 may sense user movement of linkages, joysticks, a steering wheel, buttons, dials, or pedals. Operator input sensors 980 can also sense user interactions with other operator input mechanisms, such as with a touch sensitive screen, with a microphone where speech recognition is utilized, or any of a wide variety of other operator input mechanisms.

Machine sensors 982 may sense different characteristics of agricultural harvester 100. For instance, as discussed above, machine sensors 982 may include machine speed sensors 146, separator loss sensor 148, clean grain camera 150, forward looking image capture mechanism 151, loss sensors 152 or geographic position sensor 204, examples of which are described above. Machine sensors 982 can also include machine setting sensors 991 that sense machine settings. Some examples of machine settings were described above with respect to FIG. 1. Front-end equipment (e.g., header) position sensor 993 can sense the position of the header 102, reel 164, cutter 104, or other front-end equipment relative to the frame of agricultural harvester 100. For instance, sensors 993 may sense the height of header 102 above the ground. Machine sensors 982 can also include front-end equipment (e.g., header) orientation sensors 995. Sensors 995 may sense the orientation of header 102 relative to agricultural harvester 100, or relative to the ground. Machine sensors 982 may include stability sensors 997. Stability sensors 997 sense oscillation or bouncing motion (and amplitude) of agricultural harvester 100. Machine sensors 982 may also include residue setting sensors 999 that are configured to sense whether agricultural harvester 100 is configured to chop the residue, produce a windrow, or deal with the residue in another way. Machine sensors 982 may include cleaning shoe fan speed sensor 951 that senses the speed of cleaning fan 120. Machine sensors 982 may include concave clearance sensors 953 that sense the clearance between the rotor 112 and concaves 114 on agricultural harvester 100. Machine sensors 982 may include chaffer clearance sensors 955 that sense the size of openings in chaffer 122. The machine sensors 982 may include threshing rotor speed sensor 957 that senses a rotor speed of rotor 112. Machine sensors 982 may include rotor pressure sensor 959 that senses the pressure used to drive rotor 112. Machine sensors 982 may include sieve clearance sensor 961 that senses the size of openings in sieve 124. The machine sensors 982 may include MOG moisture sensor 963 that senses a moisture level of the MOG passing through agricultural harvester 100. Machine sensors 982 may include machine orientation sensor 965 that senses the orientation of agricultural harvester 100. Machine sensors 982 may include material feed rate sensors 967 that sense the feed rate of material as the material travels through feeder house 106, clean grain elevator 130, or elsewhere in agricultural harvester 100. Machine sensors 982 can include biomass sensors 969 that sense the biomass traveling through feeder house 106, through separator 116, or elsewhere in agricultural harvester 100. The machine sensors 982 may include fuel consumption sensor 971 that senses a rate of fuel consumption over time of agricultural harvester 100. Machine sensors 982 may include power utilization sensor 973 that senses power utilization in agricultural harvester 100, such as which subsystems are utilizing power, or the rate at which subsystems are utilizing power, or the distribution of power among the subsystems in agricultural harvester 100. Machine sensors 982 may include tire pressure sensors 977 that sense the inflation pressure in tires 144 of agricultural harvester 100. Machine sensor 982 may include a wide variety of other machine performance sensors, or machine characteristic sensors, indicated by block 975. The machine performance sensors and machine characteristic sensors 975 may sense machine performance or characteristics of agricultural harvester 100.

Harvested material property sensors 984 may sense characteristics of the severed crop material as the crop material is being processed by agricultural harvester 100. The crop properties may include such things as crop type, crop moisture, grain quality (such as broken grain), MOG levels, grain constituents such as starches and protein, MOG moisture, and other crop material properties. Other sensors could sense straw "toughness", adhesion of corn to ears, and other characteristics that might be beneficially used to control processing for better grain capture, reduced grain damage, reduced power consumption, reduced grain loss, etc.

Field and soil property sensors 985 may sense characteristics of the field and soil. The field and soil properties may include soil moisture, soil compactness, the presence and location of standing water, soil type, and other soil and field characteristics.

Figure 7:
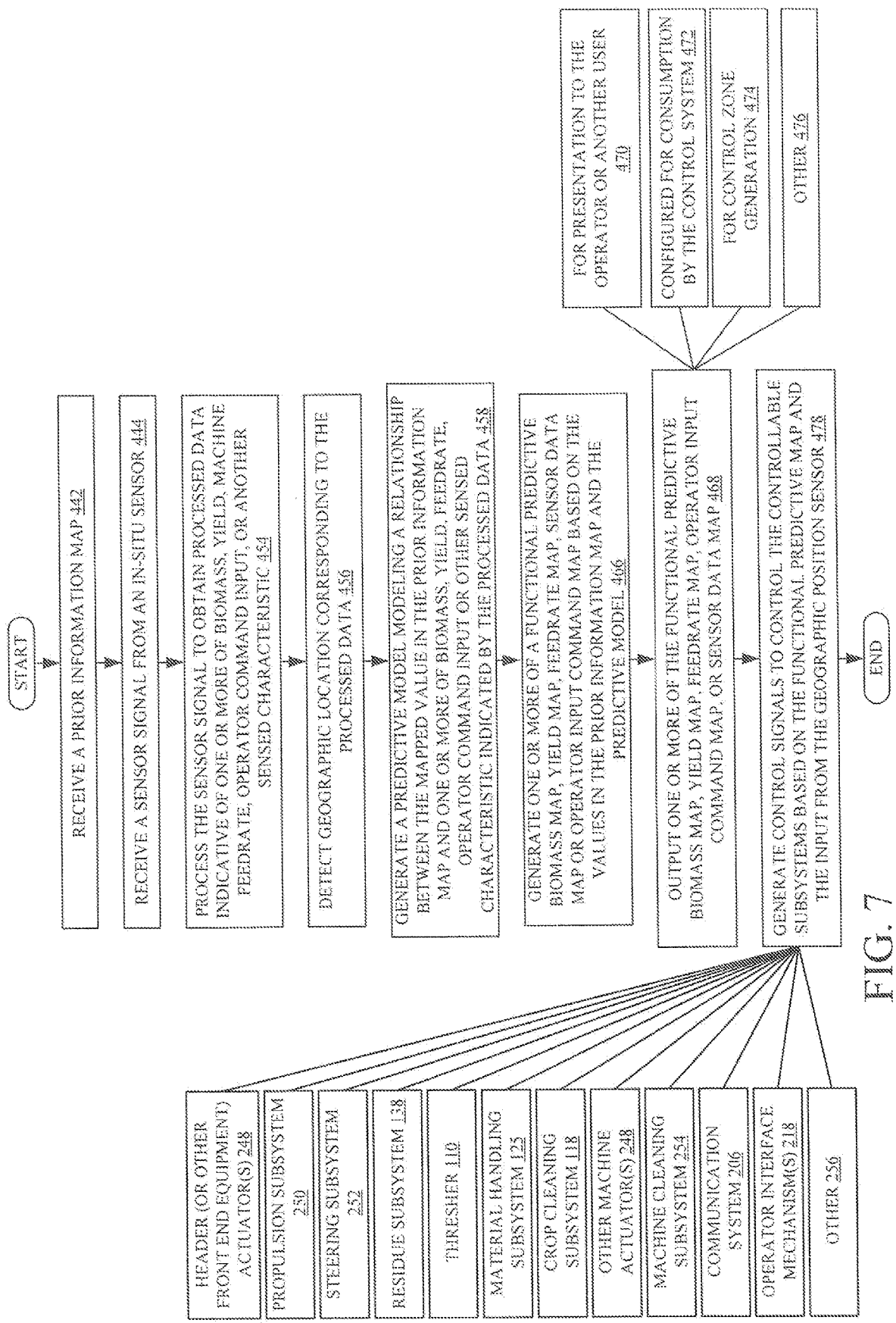
FIG. 7 shows a flow diagram illustrating one example of operation of an agricultural harvester involving generating a functional predictive map using a prior information map and an in-situ sensor input.

Environmental characteristic sensors 987 may sense one or more environmental characteristics. The environmental characteristics may include such things as wind direction and wind speed, precipitation, fog, dust level or other obscurants, or other environmental characteristics. FIG. 7 shows a flow diagram illustrating one example of the operation of predictive model generator 210 and predictive map generator 212 in generating one or more predictive models 423 and one or more functional predictive maps 430, 431, 432, 433, and 434. At block 442, predictive model generator 210 and predictive map generator 212 receive a prior information map 258. The prior information map 258 may be vegetative index map 332, predictive yield map 360, a historical yield map 333, or a prior operation map 400 created using data obtained during a prior operation in a field. At block 444, predictive model generator 210 receives a sensor signal containing sensor data from an in-situ sensor 208. The in-situ sensor can be one or more of a biomass sensor 401, which may be an optical sensor 402 or a rotor pressure sensor 403, a yield sensor 336, an operator input sensor 407, or other sensors 410, shown in FIG. 6A. Some examples of other sensors 410 are shown in FIG. 6B.

At block 454, processing system 408 processes the data contained in the sensor signal or signals received from the in-situ sensor or sensors 208 to obtain processed data 411, shown in FIG. 6. The data contained in the sensor signal or signals can be in a raw format that is processed to produce processed data 411. For example, a temperature sensor signal includes electrical resistance data. This electrical resistance data can be processed into temperature data. In other examples, processing may comprise digitizing, encoding, formatting, scaling, filtering, or classifying data. The processed data 411 may be indicative of one or more of biomass, yield, feed rate, an operator input command, or another sensed characteristic. The processed data 411 is provided to predictive model generator 210.

Returning to FIG. 7, at block 456, predictive model generator 210 also receives a geographic location 334 from geographic position sensor 204, as shown in FIG. 6. The geographic location 334 may be correlated to the geographic location from which the sensed variable or variables, sensed by in-situ sensors 208, were taken. For instance, the predictive model generator 210 can obtain the geographic location 334 from geographic position sensor 204 and determine, based upon machine delays, machine speed, etc., a precise geographic location from which the processed data 411 was derived.

At block 458, predictive model generator 210 generates one or more predictive models 423 that model a relationship between a mapped value in a prior information map and a characteristic represented in the processed data 411. For example, in some instances, the mapped value in a prior information map may be a yield or vegetative index, which may be one or more of a vegetative index value in vegetative index map 332; a predictive yield value in functional predictive yield map 360; a historical yield in historical yield map 333; or a different value in prior operation map 400, and the predictive model generator 210 generates a predictive model using the mapped value of a prior information map and a characteristic sensed by in-situ sensors 208, as represented in the processed data 411, or a related characteristic, such as a characteristic that correlates to the characteristic sensed by in-situ sensors 208.

The one or more predictive models 423 are provided to predictive map generator 212. At block 466, predictive map generator 212 generates one or more functional predictive maps 264. The functional predictive maps 264 may be functional predictive biomass map 430, functional predictive yield map 431, functional predictive feed rate map 432, functional predictive sensor data map 433, functional predictive operator command map 434, or any combination of these maps. Functional predictive biomass map 430 predicts a biomass that will be encountered by agricultural harvester 100 at different locations in the field. Functional predictive yield map 431 predicts a yield that will be encountered by agricultural harvester 100 at different locations in the field. Functional predictive feed rate map 432 predicts a desired feed rate for agricultural harvester 100 at different locations in the field. Functional predictive sensor data map 433 predicts a sensor data value that is expected to be detected by one or more in-situ sensors 208 at different locations in the field. Functional predictive operator command map 434 predicts likely operator command inputs at different locations in the field. Further, one or more of the functional predictive maps 430, 431, 432, 433, and 434 can be generated during the course of an agricultural operation. Thus, as agricultural harvester 100 is moving through a field performing an agricultural operation, the one or more predictive maps 430, 431, 432, 433, and 434 are generated as the agricultural operation is being performed.

At block 468, predictive map generator 212 outputs the one or more functional predictive maps 430, 431, 432, 433, and 434. At block 470, predictive map generator 212 may configure the map for presentation and possible interaction by an operator 260 or another user. At block 472, predictive map generator 212 may configure the map for consumption by control system 214. At block 474, predictive map generator 212 can provide the one or more predictive maps 430, 431, 432, 433, and 434 to control zone generator 213 for generation of control zones. At block 476, predictive map generator 212 configures the one or predictive maps 430, 431, 432, 433, and 434 in other ways. In an example in which the one or more functional predictive maps 430, 431, 432, 433, and 434 are provided to control zone generator 213, the one or more functional predictive maps 430, 431, 432, 433, and 434, with the control zones included therewith, represented by corresponding maps 265, described above, may be presented to operator 260 or another user or provided to control system 214 as well.

At block 478, control system 214 then generates control signals to control the controllable subsystems based upon the one or more functional predictive maps 430, 431, 432, 433, and 434 (or the functional predictive maps 430, 431, 432, 433, and 434 having control zones) as well as an input from the geographic position sensor 204. For example, when the functional predictive feed rate map 432 or functional predictive feed rate map 432 containing control zones is provided to control system 214, feed rate controller 236, in response, generates control signals to control the controllable subsystems 216 in order to control the feed rate of material through agricultural harvester 100 based upon the predicted feed rate values.

In another example, the header and reel controller 238 controls a height of header 102 based upon the predictive biomass values in functional predictive biomass map 430 or functional predictive machine biomass map 430 containing control zones. This can be used to maintain a desired feed rate of material through agricultural harvester 100 or maintain a desired stubble height to capture snow for improved soil moisture in coming year.

In another example, settings controller 232 generates control signals to control the controllable subsystems 216 to automatically generate command inputs or to recommend command inputs to operator 260 based upon the operator command values in functional predictive operator command map 434 or functional predictive operator command map 434 containing control zones. Agricultural harvester 100 could be controlled in other ways as well with other generated control signals, some of which are described below.

In another example in which control system 214 receives the functional predictive sensor data map 433 or the functional predictive sensor data map 433 with control zones added, the path planning controller 234 controls steering subsystem 252 to steer agricultural harvester 100. In another example in which control system 214 receives the functional predictive sensor data map 436 or the functional predictive sensor data map 436 with control zones added, the residue system controller 244 controls residue subsystem 138. In another example in which control system 214 receives the functional predictive sensor data map 436 or the functional predictive sensor data map 436 with control zones added, the settings controller 232 controls thresher settings of thresher 110. In another example in which control system 214 receives the functional predictive sensor data map 436 or the functional predictive sensor data map 436 with control zones added, the settings controller 232 or another controller 246 controls material handling subsystem 125. In another example in which control system 214 receives the functional predictive sensor data map 436 or the functional predictive sensor data map 436 with control zones added, the settings controller 232 controls machine cleaning subsystem 254. In another example in which control system 214 receives the functional predictive sensor data map 436 or the functional predictive sensor data map 436 with control zones added, the machine cleaning controller 245 controls machine cleaning subsystem 254 on agricultural harvester 100. In another example in which control system 214 receives the functional predictive sensor data map 436 or the functional predictive sensor data map 436 with control zones added, the communication system controller 229 controls communication system 206. In another example in which control system 214 receives the functional predictive sensor data map 436 or the functional predictive sensor data map 436 with control zones added, the operator interface controller 231 controls operator interface mechanisms 218 on agricultural harvester 100. In another example in which control system 214 receives the functional predictive sensor data map 436 or the functional predictive sensor data map 436 with control zones added, the deck plate position controller 242 controls machine/header actuators to control a deck plate on agricultural harvester 100. In another example in which control system 214 receives the functional predictive sensor data map 436 or the functional predictive sensor data map 436 with control zones added, the draper belt controller 240 controls machine/header actuators to control a draper belt on agricultural harvester 100. In another example in which control system 214 receives the functional predictive sensor data map 436 or the functional predictive sensor data map 436 with control zones added, the other controllers 246 control other controllable subsystems 256 on agricultural harvester 100.

Figure 8:
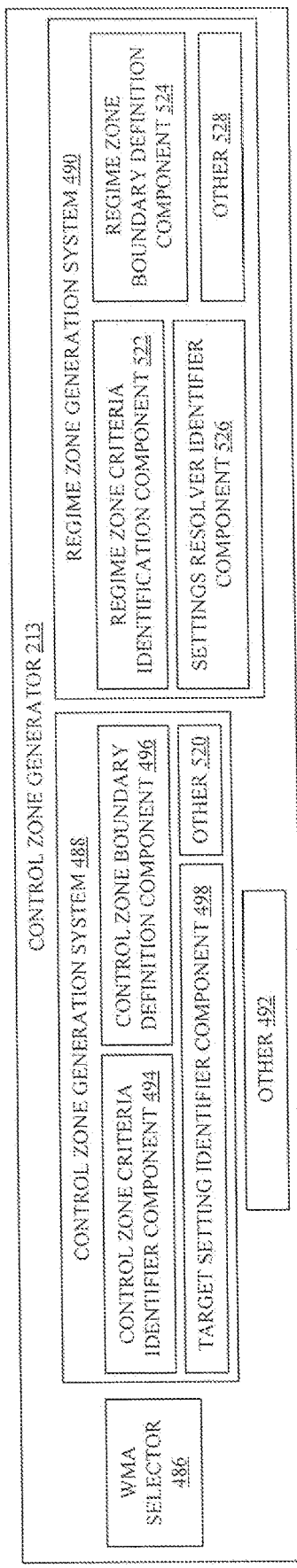
FIG. 8 is a block diagram showing one example of a control zone generator.

FIG. 8 shows a block diagram illustrating one example of control zone generator 213. Control zone generator 213 includes work machine actuator (WMA) selector 486, control zone generation system 488, and regime zone generation system 490. Control zone generator 213 may also include other items 492. Control zone generation system 488 includes control zone criteria identifier component 494, control zone boundary definition component 496, target setting identifier component 498, and other items 520. Regime zone generation system 490 includes regime zone criteria identification component 522, regime zone boundary definition component 524, settings resolver identifier component 526, and other items 528. Before describing the overall operation of control zone generator 213 in more detail, a brief description of some of the items in control zone generator 213 and the respective operations thereof will first be provided.

Agricultural harvester 100, or other work machines, may have a wide variety of different types of controllable actuators that perform different functions. The controllable actuators on agricultural harvester 100 or other work machines are collectively referred to as work machine actuators (WMAs). Each WMA may be independently controllable based upon values on a functional predictive map, or the WMAs may be controlled as sets based upon one or more values on a functional predictive map. Therefore, control zone generator 213 may generate control zones corresponding to each individually controllable WMA or corresponding to the sets of WMAs that are controlled in coordination with one another.

WMA selector 486 selects a WMA or a set of WMAs for which corresponding control zones are to be generated. Control zone generation system 488 then generates the control zones for the selected WMA or set of WMAs. For each WMA or set of WMAs, different criteria may be used in identifying control zones. For example, for one WMA, the WMA response time may be used as the criteria for defining the boundaries of the control zones. In another example, wear characteristics (e.g., how much a particular actuator or mechanism wears as a result of movement thereof) may be used as the criteria for identifying the boundaries of control zones. Control zone criteria identifier component 494 identifies particular criteria that are to be used in defining control zones for the selected WMA or set of WMAs. Control zone boundary definition component 496 processes the values on a functional predictive map under analysis to define the boundaries of the control zones on that functional predictive map based upon the values in the functional predictive map under analysis and based upon the control zone criteria for the selected WMA or set of WMAs.

Target setting identifier component 498 sets a value of the target setting that will be used to control the WMA or set of WMAs in different control zones. For instance, if the selected WMA is propulsion system 250 and the functional predictive map under analysis is a functional predictive speed map 438, then the target setting in each control zone may be a target speed setting based on speed values contained in the functional predictive speed map 238 within the identified control zone.

In some examples, where agricultural harvester 100 is to be controlled based on a current or future location of the agricultural harvester 100, multiple target settings may be possible for a WMA at a given position. In that case, the target settings may have different values and may be competing. Thus, the target settings need to be resolved so that only a single target setting is used to control the WMA. For example, where the WMA is an actuator in propulsion system 250 that is being controlled in order to control the speed of agricultural harvester 100, multiple different competing sets of criteria may exist that are considered by control zone generation system 488 in identifying the control zones and the target settings for the selected WMA in the control zones. For instance, different target settings for controlling machine speed may be generated based upon, for example, a detected or predicted feed rate value, a detected or predictive fuel efficiency value, a detected or predicted grain loss value, or a combination of these. However, at any given time, the agricultural harvester 100 cannot travel over the ground at multiple speeds simultaneously. Rather, at any given time, the agricultural harvester 100 travels at a single speed. Thus, one of the competing target settings is selected to control the speed of agricultural harvester 100.

Therefore, in some examples, regime zone generation system 490 generates regime zones to resolve multiple different competing target settings. Regime zone criteria identification component 522 identifies the criteria that are used to establish regime zones for the selected WMA or set of WMAs on the functional predictive map under analysis. Some criteria that can be used to identify or define regime zones include, for example, crop type or crop variety based on an as-planted map or another source of the crop type or crop variety, weed type, weed intensity, or crop state, such as whether the crop is down, partially down or standing. Just as each WMA or set of WMAs may have a corresponding control zone, different WMAs or sets of WMAs may have a corresponding regime zone. Regime zone boundary definition component 524 identifies the boundaries of regime zones on the functional predictive map under analysis based on the regime zone criteria identified by regime zone criteria identification component 522.

In some examples, regime zones may overlap with one another. For instance, a crop variety regime zone may overlap with a portion of or an entirety of a crop state regime zone. In such an example, the different regime zones may be assigned to a precedence hierarchy so that, where two or more regime zones overlap, the regime zone assigned with a greater hierarchical position or importance in the precedence hierarchy has precedence over the regime zones that have lesser hierarchical positions or importance in the precedence hierarchy. The precedence hierarchy of the regime zones may be manually set or may be automatically set using a rules-based system, a model-based system, or another system. As one example, where a downed crop regime zone overlaps with a crop variety regime zone, the downed crop regime zone may be assigned a greater importance in the precedence hierarchy than the crop variety regime zone so that the downed crop regime zone takes precedence.

In addition, each regime zone may have a unique settings resolver for a given WMA or set of WMAs. Settings resolver identifier component 526 identifies a particular settings resolver for each regime zone identified on the functional predictive map under analysis and a particular settings resolver for the selected WMA or set of WMAs.

Once the settings resolver for a particular regime zone is identified, that settings resolver may be used to resolve competing target settings, where more than one target setting is identified based upon the control zones. The different types of settings resolvers can have different forms. For instance, the settings resolvers that are identified for each regime zone may include a human choice resolver in which the competing target settings are presented to an operator or other user for resolution. In another example, the settings resolver may include a neural network or other artificial intelligence or machine learning system. In such instances, the settings resolvers may resolve the competing target settings based upon a predicted or historic quality metric corresponding to each of the different target settings. As an example, an increased vehicle speed setting may reduce the time to harvest a field and reduce corresponding time-based labor and equipment costs but may increase grain losses. A reduced vehicle speed setting may increase the time to harvest a field and increase corresponding time-based labor and equipment costs but may decrease grain losses. When grain loss or time to harvest is selected as a quality metric, the predicted or historic value for the selected quality metric, given the two competing vehicle speed settings values, may be used to resolve the speed setting. In some instances, the settings resolvers may be a set of threshold rules that may be used instead of, or in addition to, the regime zones. An example of a threshold rule may be expressed as follows:

If predicted biomass values within 20 feet of the header of the agricultural harvester 100 are greater that x kilograms (where x is a selected or predetermined value), then use the target setting value that is chosen based on feed rate over other competing target settings, otherwise use the target setting value based on grain loss over other competing target setting values.

The settings resolvers may be logical components that execute logical rules in identifying a target setting. For instance, the settings resolver may resolve target settings while attempting to minimize harvest time or minimize the total harvest cost or maximize harvested grain or based on other variables that are computed as a function of the different candidate target settings. A harvest time may be minimized when an amount to complete a harvest is reduced to at or below a selected threshold. A total harvest cost may be minimized where the total harvest cost is reduced to at or below a selected threshold. Harvested grain may be maximized where the amount of harvested grain is increased to at or above a selected threshold.

Figure 9:
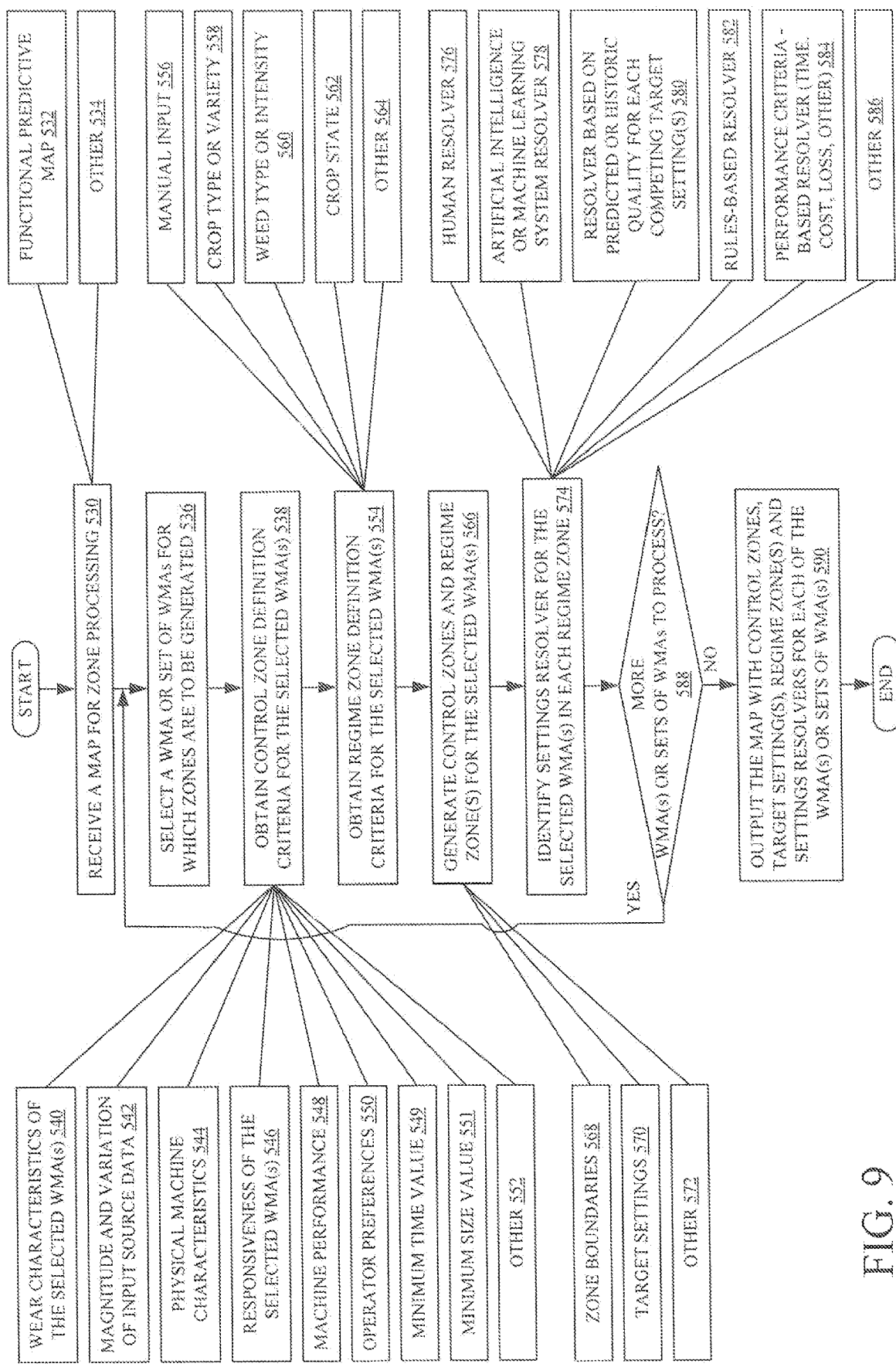
FIG. 9 is a flow diagram illustrating one example of the operation of the control zone generator shown in FIG. 8.

FIG. 9 is a flow diagram illustrating one example of the operation of control zone generator 213 in generating control zones and regime zones for a map that the control zone generator 213 receives for zone processing (e.g., for a map under analysis).

At block 530, control zone generator 213 receives a map under analysis for processing. In one example, as shown at block 532, the map under analysis is a functional predictive map. For example, the map under analysis may be one of the functional predictive maps 436, 437, 438, or 440. Block 534 indicates that the map under analysis can be other maps as well.

At block 536, WMA selector 486 selects a WMA or a set of WMAs for which control zones are to be generated on the map under analysis. At block 538, control zone criteria identification component 494 obtains control zone definition criteria for the selected WMAs or set of WMAs. Block 540 indicates an example in which the control zone criteria are or include wear characteristics of the selected WMA or set of WMAs. Block 542 indicates an example in which the control zone definition criteria are or include a magnitude and variation of input source data, such as the magnitude and variation of the values on the map under analysis or the magnitude and variation of inputs from various in-situ sensors 208. Block 544 indicates an example in which the control zone definition criteria are or include physical machine characteristics, such as the physical dimensions of the machine, a speed at which different subsystems operate, or other physical machine characteristics. Block 546 indicates an example in which the control zone definition criteria are or include a responsiveness of the selected WMA or set of WMAs in reaching newly commanded setting values. Block 548 indicates an example in which the control zone definition criteria are or include machine performance metrics. Block 550 indicates an example in which the control zone definition criteria are or includes operator preferences. Block 552 indicates an example in which the control zone definition criteria are or include other items as well. Block 549 indicates an example in which the control zone definition criteria are time based, meaning that agricultural harvester 100 will not cross the boundary of a control zone until a selected amount of time has elapsed since agricultural harvester 100 entered a particular control zone. In some instances, the selected amount of time may be a minimum amount of time. Thus, in some instances, the control zone definition criteria may prevent the agricultural harvester 100 from crossing a boundary of a control zone until at least the selected amount of time has elapsed. Block 551 indicates an example in which the control zone definition criteria are based on a selected size value. For example, a control zone definition criteria that is based on a selected size value may preclude definition of a control zone that is smaller than the selected size. In some instances, the selected size may be a minimum size.

At block 554, regime zone criteria identification component 522 obtains regime zone definition criteria for the selected WMA or set of WMAs. Block 556 indicates an example in which the regime zone definition criteria are based on a manual input from operator 260 or another user. Block 558 illustrates an example in which the regime zone definition criteria are based on crop type or crop variety. Block 560 illustrates an example in which the regime zone definition criteria are based on weed type or weed intensity or both. Block 562 illustrates an example in which the regime zone definition criteria are based on or include crop state. Block 564 indicates an example in which the regime zone definition criteria are or include other criteria as well.

At block 566, control zone boundary definition component 496 generates the boundaries of control zones on the map under analysis based upon the control zone criteria. Regime zone boundary definition component 524 generates the boundaries of regime zones on the map under analysis based upon the regime zone criteria. Block 568 indicates an example in which the zone boundaries are identified for the control zones and the regime zones. Block 570 shows that target setting identifier component 498 identifies the target settings for each of the control zones. The control zones and regime zones can be generated in other ways as well, and this is indicated by block 572.

At block 574, settings resolver identifier component 526 identifies the settings resolver for the selected WMAs in each regime zone defined by regimes zone boundary definition component 524. As discussed above, the regime zone resolver can be a human resolver 576, an artificial intelligence or machine learning system resolver 578, a resolver 580 based on predicted or historic quality for each competing target setting, a rules-based resolver 582, a performance criteria-based resolver 584, or other resolvers 586.

At block 588, WMA selector 486 determines whether there are more WMAs or sets of WMAs to process. If additional WMAs or sets of WMAs are remaining to be processed, processing reverts to block 436 where the next WMA or set of WMAs for which control zones and regime zones are to be defined is selected. When no additional WMAs or sets of WMAs for which control zones or regime zones are to be generated are remaining, processing moves to block 590 where control zone generator 213 outputs a map with control zones, target settings, regime zones, and settings resolvers for each of the WMAs or sets of WMAs. As discussed above, the outputted map can be presented to operator 260 or another user; the outputted map can be provided to control system 214; or the outputted map can be output in other ways.

Figure 10:
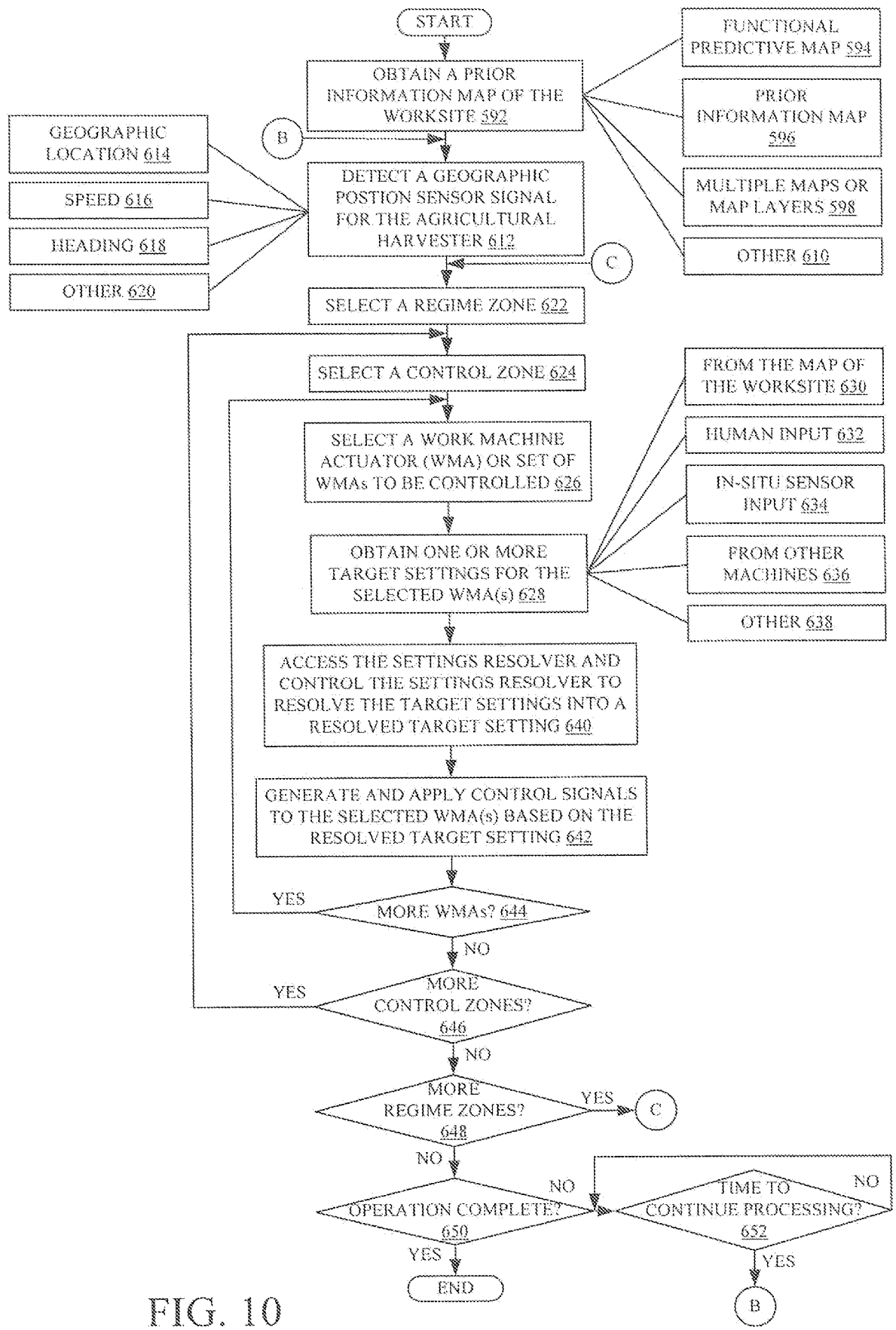
FIG. 10 illustrates a flow diagram showing an example of operation of a control system in selecting a target settings value to control an agricultural harvester.

FIG. 10 illustrates one example of the operation of control system 214 in controlling agricultural harvester 100 based upon a map that is output by control zone generator 213. Thus, at block 592, control system 214 receives a map of the worksite. In some instances, the map can be a functional predictive map that may include control zones and regime zones, as represented by block 594. In some instances, the received map may be a functional predictive map that excludes control zones and regime zones. Block 596 indicates an example in which the received map of the worksite can be a prior information map having control zones and regime zones identified on it. Block 598 indicates an example in which the received map can include multiple different maps or multiple different map layers. Block 610 indicates an example in which the received map can take other forms as well.

At block 612, control system 214 receives a sensor signal from geographic position sensor 204. The sensor signal from geographic position sensor 204 can include data that indicates the geographic location 614 of agricultural harvester 100, the speed 616 of agricultural harvester 100, the heading 618 or agricultural harvester 100, or other information 620. At block 622, zone controller 247 selects a regime zone, and, at block 624, zone controller 247 selects a control zone on the map based on the geographic position sensor signal. At block 626, zone controller 247 selects a WMA or a set of WMAs to be controlled. At block 628, zone controller 247 obtains one or more target settings for the selected WMA or set of WMAs. The target settings that are obtained for the selected WMA or set of WMAs may come from a variety of different sources. For instance, block 630 shows an example in which one or more of the target settings for the selected WMA or set of WMAs is based on an input from the control zones on the map of the worksite. Block 632 shows an example in which one or more of the target settings is obtained from human inputs from operator 260 or another user. Block 634 shows an example in which the target settings are obtained from an in-situ sensor 208. Block 636 shows an example in which the one or more target settings is obtained from one or more sensors on other machines working in the same field either concurrently with agricultural harvester 100 or from one or more sensors on machines that worked in the same field in the past. Block 638 shows an example in which the target settings are obtained from other sources as well.

At block 640, zone controller 247 accesses the settings resolver for the selected regime zone and controls the settings resolver to resolve competing target settings into a resolved target setting. As discussed above, in some instances, the settings resolver may be a human resolver in which case zone controller 247 controls operator interface mechanisms 218 to present the competing target settings to operator 260 or another user for resolution. In some instances, the settings resolver may be a neural network or other artificial intelligence or machine learning system, and zone controller 247 submits the competing target settings to the neural network, artificial intelligence, or machine learning system for selection. In some instances, the settings resolver may be based on a predicted or historic quality metric, on threshold rules, or on logical components. In any of these latter examples, zone controller 247 executes the settings resolver to obtain a resolved target setting based on the predicted or historic quality metric, based on the threshold rules, or with the use of the logical components.

At block 642, with zone controller 247 having identified the resolved target setting, zone controller 247 provides the resolved target setting to other controllers in control system 214, which generate and apply control signals to the selected WMA or set of WMAs based upon the resolved target setting. For instance, where the selected WMA is a machine or header actuator 248, zone controller 247 provides the resolved target setting to settings controller 232 or header/real controller 238 or both to generate control signals based upon the resolved target setting, and those generated control signals are applied to the machine or header actuators 248. At block 644, if additional WMAs or additional sets of WMAs are to be controlled at the current geographic location of the agricultural harvester 100 (as detected at block 612), then processing reverts to block 626 where the next WMA or set of WMAs is selected. The processes represented by blocks 626 through 644 continue until all of the WMAs or sets of WMAs to be controlled at the current geographical location of the agricultural harvester 100 have been addressed. If no additional WMAs or sets of WMAs are to be controlled at the current geographic location of the agricultural harvester 100 remain, processing proceeds to block 646 where zone controller 247 determines whether additional control zones to be considered exist in the selected regime zone. If additional control zones to be considered exist, processing reverts to block 624 where a next control zone is selected. If no additional control zones are remaining to be considered, processing proceeds to block 648 where a determination as to whether additional regime zones are remaining to be consider. Zone controller 247 determines whether additional regime zones are remaining to be considered. If additional regimes zone are remaining to be considered, processing reverts to block 622 where a next regime zone is selected.

At block 650, zone controller 247 determines whether the operation that agricultural harvester 100 is performing is complete. If not, the zone controller 247 determines whether a control zone criterion has been satisfied to continue processing, as indicated by block 652. For instance, as mentioned above, control zone definition criteria may include criteria defining when a control zone boundary may be crossed by the agricultural harvester 100. For example, whether a control zone boundary may be crossed by the agricultural harvester 100 may be defined by a selected time period, meaning that agricultural harvester 100 is prevented from crossing a zone boundary until a selected amount of time has transpired. In that case, at block 652, zone controller 247 determines whether the selected time period has elapsed. Additionally, zone controller 247 can perform processing continually. Thus, zone controller 247 does not wait for any particular time period before continuing to determine whether an operation of the agricultural harvester 100 is completed. At block 652, zone controller 247 determines that it is time to continue processing, then processing continues at block 612 where zone controller 247 again receives an input from geographic position sensor 204. It will also be appreciated that zone controller 247 can control the WMAs and sets of WMAs simultaneously using a multiple-input, multiple-output controller instead of controlling the WMAs and sets of WMAs sequentially.

Figure 11:
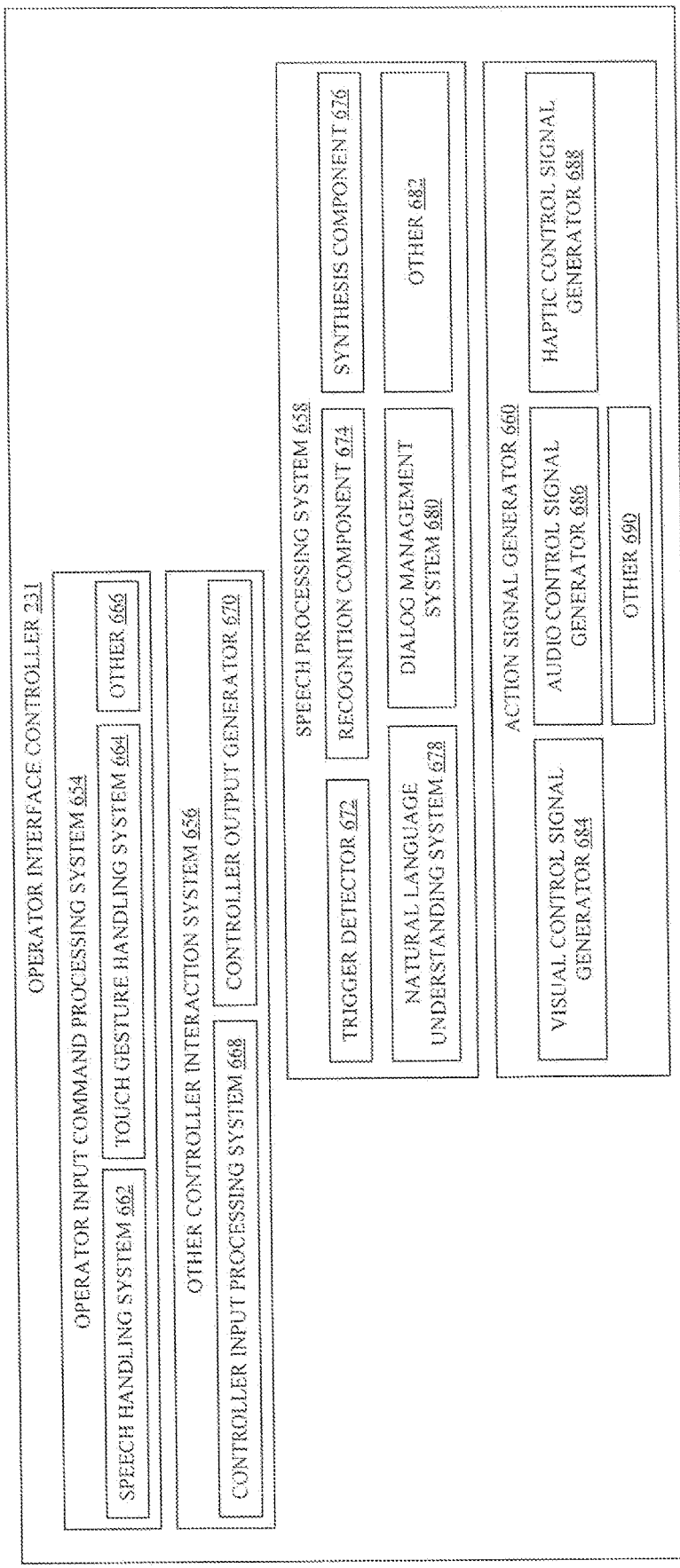
FIG. 11 is a block diagram showing one example of an operator interface controller.

FIG. 11 is a block diagram showing one example of an operator interface controller 231. In an illustrated example, operator interface controller 231 includes operator input command processing system 654, other controller interaction system 656, speech processing system 658, and action signal generator 660. Operator input command processing system 654 includes speech handling system 662, touch gesture handling system 664, and other items 666. Other controller interaction system 656 includes controller input processing system 668 and controller output generator 670. Speech processing system 658 includes trigger detector 672, recognition component 674, synthesis component 676, natural language understanding system 678, dialog management system 680, and other items 682. Action signal generator 660 includes visual control signal generator 684, audio control signal generator 686, haptic control signal generator 688, and other items 690. Before describing operation of the example operator interface controller 231 shown in FIG. 11 in handling various operator interface actions, a brief description of some of the items in operator interface controller 231 and the associated operation thereof is first provided.

Operator input command processing system 654 detects operator inputs on operator interface mechanisms 218 and processes those inputs for commands. Speech handling system 662 detects speech inputs and handles the interactions with speech processing system 658 to process the speech inputs for commands. Touch gesture handling system 664 detects touch gestures on touch sensitive elements in operator interface mechanisms 218 and processes those inputs for commands.

Other controller interaction system 656 handles interactions with other controllers in control system 214. Controller input processing system 668 detects and processes inputs from other controllers in control system 214, and controller output generator 670 generates outputs and provides those outputs to other controllers in control system 214. Speech processing system 658 recognizes speech inputs, determines the meaning of those inputs, and provides an output indicative of the meaning of the spoken inputs. For instance, speech processing system 658 may recognize a speech input from operator 260 as a settings change command in which operator 260 is commanding control system 214 to change a setting for a controllable subsystem 216. In such an example, speech processing system 658 recognizes the content of the spoken command, identifies the meaning of that command as a settings change command, and provides the meaning of that input back to speech handling system 662. Speech handling system 662, in turn, interacts with controller output generator 670 to provide the commanded output to the appropriate controller in control system 214 to accomplish the spoken settings change command.

Speech processing system 658 may be invoked in a variety of different ways. For instance, in one example, speech handling system 662 continuously provides an input from a microphone (being one of the operator interface mechanisms 218) to speech processing system 658. The microphone detects speech from operator 260, and the speech handling system 662 provides the detected speech to speech processing system 658. Trigger detector 672 detects a trigger indicating that speech processing system 658 is invoked. In some instances, when speech processing system 658 is receiving continuous speech inputs from speech handling system 662, speech recognition component 674 performs continuous speech recognition on all speech spoken by operator 260. In some instances, speech processing system 658 is configured for invocation using a wakeup word. That is, in some instances, operation of speech processing system 658 may be initiated based on recognition of a selected spoken word, referred to as the wakeup word. In such an example, where recognition component 674 recognizes the wakeup word, the recognition component 674 provides an indication that the wakeup word has been recognized to trigger detector 672. Trigger detector 672 detects that speech processing system 658 has been invoked or triggered by the wakeup word. In another example, speech processing system 658 may be invoked by an operator 260 actuating an actuator on a user interface mechanism, such as by touching an actuator on a touch sensitive display screen, by pressing a button, or by providing another triggering input. In such an example, trigger detector 672 can detect that speech processing system 658 has been invoked when a triggering input via a user interface mechanism is detected. Trigger detector 672 can detect that speech processing system 658 has been invoked in other ways as well.

Once speech processing system 658 is invoked, the speech input from operator 260 is provided to speech recognition component 674. Speech recognition component 674 recognizes linguistic elements in the speech input, such as words, phrases, or other linguistic units. Natural language understanding system 678 identifies a meaning of the recognized speech. The meaning may be a natural language output, a command output identifying a command reflected in the recognized speech, a value output identifying a value in the recognized speech, or any of a wide variety of other outputs that reflect the understanding of the recognized speech. For example, the natural language understanding system 678 and speech processing system 568, more generally, may understand of the meaning of the recognized speech in the context of agricultural harvester 100.

In some examples, speech processing system 658 can also generate outputs that navigate operator 260 through a user experience based on the speech input. For instance, dialog management system 680 may generate and manage a dialog with the user in order to identify what the user wishes to do. The dialog may disambiguate a user's command; identify one or more specific values that are needed to carry out the user's command; or obtain other information from the user or provide other information to the user or both. Synthesis component 676 may generate speech synthesis which can be presented to the user through an audio operator interface mechanism, such as a speaker. Thus, the dialog managed by dialog management system 680 may be exclusively a spoken dialog or a combination of both a visual dialog and a spoken dialog.

Action signal generator 660 generates action signals to control operator interface mechanisms 218 based upon outputs from one or more of operator input command processing system 654, other controller interaction system 656, and speech processing system 658. Visual control signal generator 684 generates control signals to control visual items in operator interface mechanisms 218. The visual items may be lights, a display screen, warning indicators, or other visual items. Audio control signal generator 686 generates outputs that control audio elements of operator interface mechanisms 218. The audio elements include a speaker, audible alert mechanisms, horns, or other audible elements. Haptic control signal generator 688 generates control signals that are output to control haptic elements of operator interface mechanisms 218. The haptic elements include vibration elements that may be used to vibrate, for example, the operator's seat, the steering wheel, pedals, or joysticks used by the operator. The haptic elements may include tactile feedback or force feedback elements that provide tactile feedback or force feedback to the operator through operator interface mechanisms. The haptic elements may include a wide variety of other haptic elements as well.

Figure 12:
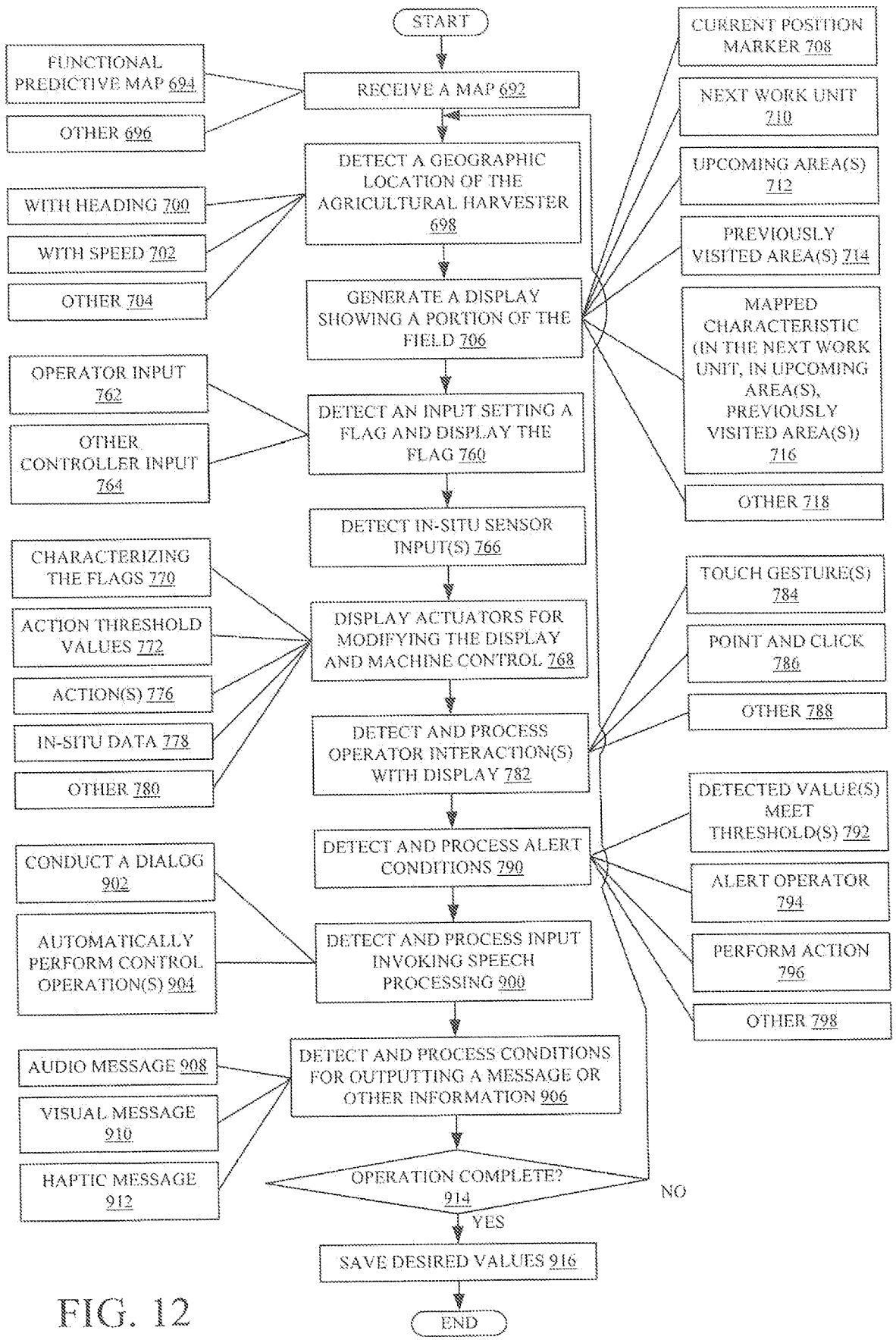
FIG. 12 is a flow diagram illustrating one example of an operator interface controller.

FIG. 12 is a flow diagram illustrating one example of the operation of operator interface controller 231 in generating an operator interface display on an operator interface mechanism 218, which can include a touch sensitive display screen. FIG. 12 also illustrates one example of how operator interface controller 231 can detect and process operator interactions with the touch sensitive display screen.

At block 692, operator interface controller 231 receives a map. Block 694 indicates an example in which the map is a functional predictive map, and block 696 indicates an example in which the map is another type of map. At block 698, operator interface controller 231 receives an input from geographic position sensor 204 identifying the geographic location of the agricultural harvester 100. As indicated in block 700, the input from geographic position sensor 204 can include the heading, along with the location, of agricultural harvester 100. Block 702 indicates an example in which the input from geographic position sensor 204 includes the speed of agricultural harvester 100, and block 704 indicates an example in which the input from geographic position sensor 204 includes other items.

At block 706, visual control signal generator 684 in operator interface controller 231 controls the touch sensitive display screen in operator interface mechanisms 218 to generate a display showing all or a portion of a field represented by the received map. Block 708 indicates that the displayed field can include a current position marker showing a current position of the agricultural harvester 100 relative to the field. Block 710 indicates an example in which the displayed field includes a next work unit marker that identifies a next work unit (or area on the field) in which agricultural harvester 100 will be operating. Block 712 indicates an example in which the displayed field includes an upcoming area display portion that displays areas that are yet to be processed by agricultural harvester 100, and block 714 indicates an example in which the displayed field includes previously visited display portions that represent areas of the field that agricultural harvester 100 has already processed. Block 716 indicates an example in which the displayed field displays various characteristics of the field having georeferenced locations on the map. For instance, if the received map is a yield map, the displayed field may show the different yield values in the field georeferenced within the displayed field. The mapped characteristics can be shown in the previously visited areas (as shown in block 714), in the upcoming areas (as shown in block 712), and in the next work unit (as shown in block 710). Block 718 indicates an example in which the displayed field includes other items as well.

Figure 13:
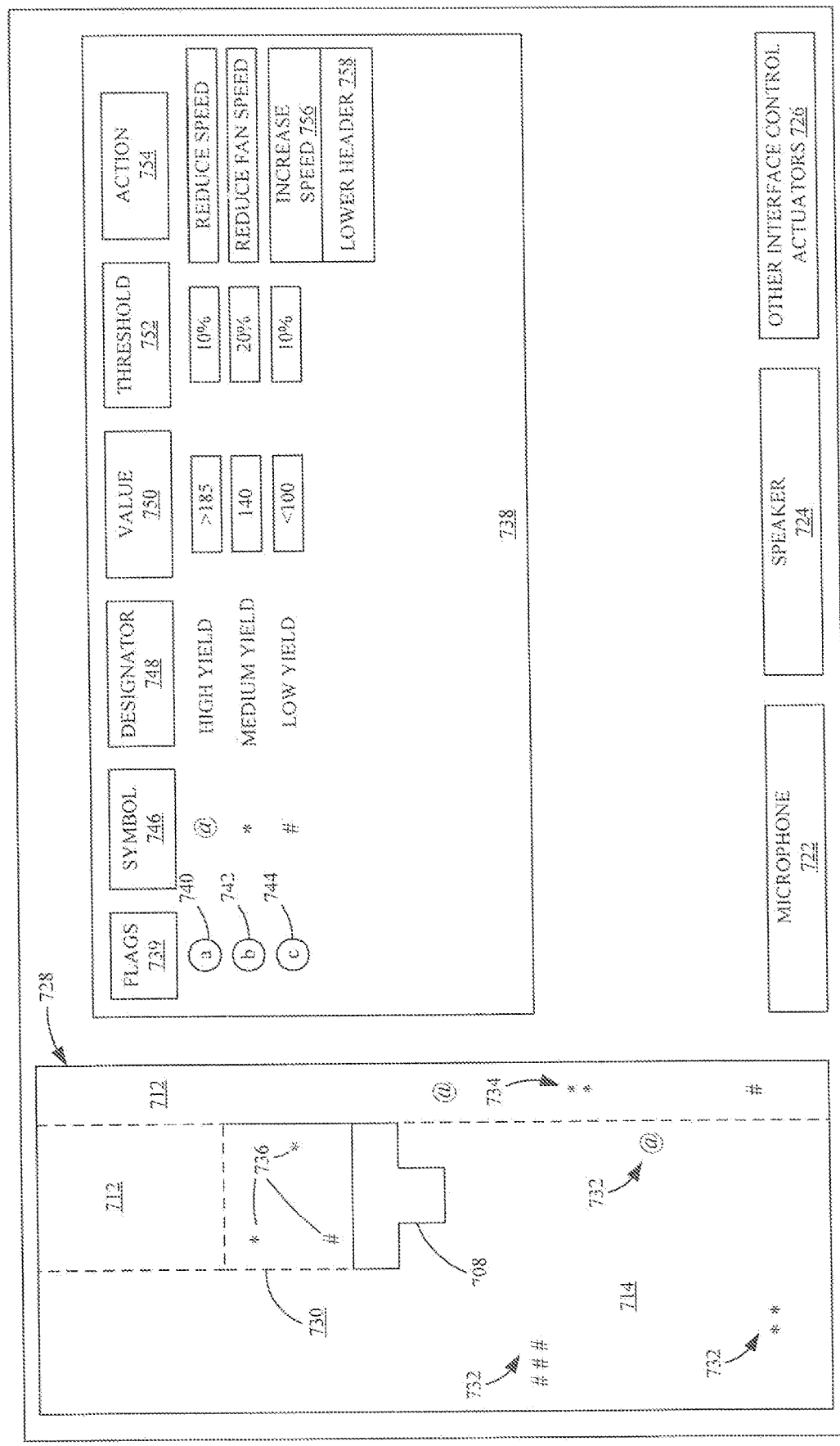
FIG. 13 is a pictorial illustration showing one example of an operator interface display.

FIG. 13 is a pictorial illustration showing one example of a user interface display 720 that can be generated on a touch sensitive display screen. In other instances, the user interface display 720 may be generated on other types of displays. The touch sensitive display screen may be mounted in the operator compartment of agricultural harvester 100 or on the mobile device or elsewhere. User interface display 720 will be described prior to continuing with the description of the flow diagram shown in FIG. 12.

In the example shown in FIG. 13, user interface display 720 illustrates that the touch sensitive display screen includes a display feature for operating a microphone 722 and a speaker 724. Thus, the touch sensitive display may be communicably coupled to the microphone 722 and the speaker 724. Block 726 indicates that the touch sensitive display screen can include a wide variety of user interface control actuators, such as buttons, keypads, soft keypads, links, icons, switches, etc. The operator 260 can actuator the user interface control actuators to perform various functions.

In the example shown in FIG. 13, user interface display 720 includes a field display portion 728 that displays at least a portion of the field in which the agricultural harvester 100 is operating. The field display portion 728 is shown with a current position marker 708 that corresponds to a current position of agricultural harvester 100 in the portion of the field shown in field display portion 728. In one example, the operator may control the touch sensitive display in order to zoom into portions of field display portion 728 or to pan or scroll the field display portion 728 to show different portions of the field. A next work unit 730 is shown as an area of the field directly in front of the current position marker 708 of agricultural harvester 100. The current position marker 708 may also be configured to identify the direction of travel of agricultural harvester 100, a speed of travel of agricultural harvester 100 or both. In FIG. 13, the shape of the current position marker 708 provides an indication as to the orientation of the agricultural harvester 100 within the field which may be used as an indication of a direction of travel of the agricultural harvester 100.

The size of the next work unit 730 marked on field display portion 728 may vary based upon a wide variety of different criteria. For instance, the size of next work unit 730 may vary based on the speed of travel of agricultural harvester 100. Thus, when the agricultural harvester 100 is traveling faster, then the area of the next work unit 730 may be larger than the area of next work unit 730 if agricultural harvester 100 is traveling more slowly. Field display portion 728 is also shown displaying previously visited area 714 and upcoming areas 712. Previously visited areas 714 represent areas that are already harvested while upcoming areas 712 represent areas that still need to be harvested. The field display portion 728 is also shown displaying different characteristics of the field. In the example illustrated in FIG. 13, the map that is being displayed is a yield map. Therefore, a plurality of different yield markers are displayed on field display portion 728. There are a set of yield display markers 732 shown in the already visited areas 714. There are also a set of yield display markers 734 shown in the upcoming areas 712, and there are a set of yield display markers 736 shown in the next work unit 730. FIG. 13 shows that the yield display markers 732, 734, and 736 are made up of different symbols. Each of the symbols represents a yield amount. In the example shown in FIG. 3, the @ symbol represents high yield; the * symbol represents medium yield; and the #symbol represents low yield. Thus, the field display portion 728 shows different amounts of yield that are located at different areas within the field. As described earlier, the display markers 732 may be made up of different symbols, and, as described below, the symbols may be any display feature such as different colors, shapes, patterns, intensities, text, icons, or other display features. In some instances, each location of the field may have a display marker associated therewith. Thus, in some instances, a display marker may be provided at each location of the field display portion 728 to identify the nature of the characteristic being mapped for each particular location of the field. Consequently, the present disclosure encompasses providing a display marker, such as the loss level display marker 732 (as in the context of the present example of FIG. 11), at one or more locations on the field display portion 728 to identify the nature, degree, etc., of the characteristic being displayed, thereby identifying the characteristic at the corresponding location in the field being displayed.

In the example of FIG. 13, user interface display 720 also has a control display portion 738. Control display portion 738 allows the operator to view information and to interact with user interface display 720 in various ways.

The actuators and display markers in portion 738 may be displayed as, for example, individual items, fixed lists, scrollable lists, drop down menus, or drop down lists. In the example shown in FIG. 13, display portion 738 shows information for the three different amounts of yield that correspond to the three symbols mentioned above. In other examples, yield values can be in greater granularity than the three levels of yield values shown. Display portion 738 also includes a set of touch sensitive actuators with which the operator 260 can interact by touch. For example, the operator 260 may touch the touch sensitive actuators with a finger to activate the respective touch sensitive actuator.

A flag column 739 shows flags that have been automatically or manually set. Flag actuator 740 allows operator 260 to mark a location, and then add information indicating the values yield at the location. For instance, when the operator 260 actuates the flag actuator 740 by touching the flag actuator 740, touch gesture handling system 664 in operator interface controller 231 identifies the current location as one where the yield is high. Or for instance, when the operator 260 touches the button 742, touch gesture handling system 664 identifies the current location as a location where medium yield is present. Or for instance, when the operator 260 touches the button 744, touch gesture handling system 664 identifies the current location as a location where low yield is present. Touch gesture handling system 664 also controls visual control signal generator 684 to add a symbol corresponding to the identified yield value on field display portion 728 at a location the user identifies before or after or during actuation of buttons 740, 742 or 744.

Column 746 displays the symbols corresponding to each yield value that is being tracked on the field display portion 728. Designator column 748 shows the designator (which may be a textual designator or other designator) identifying the yield value. Without limitation, the yield symbols in column 746 and the designators in column 748 can include any display feature such as different colors, shapes, patterns, intensities, text, icons, or other display feature. Column shows measured yield values. In the example shown in FIG. 13, the yield values are values representative of bushels per acre of corn. The values displayed in column 750 can be predicted values or values measured by in-situ sensors 208. In one example, the operator 260 can select the particular part of field display portion 728 for which the values in column 750 are to be displayed. Thus, the values in column 750 can correspond to values in display portions 712, 714 or 730. Column 752 displays action threshold values. Action threshold values in column 752 may be threshold values corresponding to the measured values in column 750. If the measured values in column 750 satisfy the corresponding action threshold values in column 752, then control system 214 takes the action identified in column 754. In some instances, a measured value may satisfy a corresponding action threshold value by meeting or exceeding the corresponding action threshold value. In one example, operator 260 can select a threshold value, for example, in order to change the threshold value by touching the threshold value in column 752. Once selected, the operator 260 may change the threshold value. The threshold values in column 752 can be configured such that the designated action is performed when the measured value 750 exceeds the threshold value, equals the threshold value, or is less than the threshold value.

Similarly, operator 260 can touch the action identifiers in column 754 to change the action that is to be taken. When a threshold is met, multiple actions may be taken. For instance, at the bottom of column 754, an increase speed action 756 and an lower header action 758 are identified as actions that will be taken if the measured value in column 750 meets the threshold value in column 752.

The actions that can be set in column 754 can be any of a wide variety of different types of actions. For example, the actions can include a keep out action which, when executed, inhibits agricultural harvester 100 from further harvesting in an area. The actions can include a speed change action which, when executed, changes the travel speed of agricultural harvester 100 through the field. The actions can include a setting change action for changing a setting of an internal actuator or another WMA or set of WMAs or for implementing a settings change action that changes a setting of a header. These are examples only, and a wide variety of other actions are contemplated herein.

The display markers shown on user interface display 720 can be visually controlled. Visually controlling the interface display 720 may be performed to capture the attention of operator 260. For instance, the display markers can be controlled to modify the intensity, color, or pattern with which the display markers are displayed. Additionally, the display markers may be controlled to flash. The described alterations to the visual appearance of the display markers are provided as examples. Consequently, other aspects of the visual appearance of the display markers may be altered. Therefore, the display markers can be modified under various circumstances in a desired manner in order, for example, to capture the attention of operator 260.

Various functions that can be accomplished by the operator 260 using user interface display 720 can also be accomplished automatically, such as by other controllers in control system 214.

Returning now to the flow diagram of FIG. 12, the description of the operation of operator interface controller 231 continues. At block 760, operator interface controller 231 detects an input setting a flag and controls the touch sensitive user interface display 720 to display the flag on field display portion 728. The detected input may be an operator input, as indicated at 762, or an input from another controller, as indicated at 764. At block 766, operator interface controller 231 detects an in-situ sensor input indicative of a measured characteristic of the field from one of the in-situ sensors 208. At block 768, visual control signal generator 684 generates control signals to control user interface display 720 to display actuators for modifying user interface display 720 and for modifying machine control. For instance, block 770 represents that one or more of the actuators for setting or modifying the values in columns 739, 746, and 748 can be displayed. Thus, the user can set flags and modify characteristics of those flags. For example, a user can modify the yield values or ranges, shown in column 750, and designators corresponding to the flags. Block 772 represents that action threshold values in column 752 are displayed. Block 776 represents that the actions in column 754 are displayed, and block 778 represents that the measured in-situ data in column 750 is displayed. Block 780 indicates that a wide variety of other information and actuators can be displayed on user interface display 720 as well.

At block 782, operator input command processing system 654 detects and processes operator inputs corresponding to interactions with the user interface display 720 performed by the operator 260. Where the user interface mechanism on which user interface display 720 is displayed is a touch sensitive display screen, interaction inputs with the touch sensitive display screen by the operator 260 can be touch gestures 784. In some instances, the operator interaction inputs can be inputs using a point and click device 786 or other operator interaction inputs 788.

At block 790, operator interface controller 231 receives signals indicative of an alert condition. For instance, block 792 indicates that signals may be received by controller input processing system 668 indicating that detected values in column 750 satisfy threshold conditions present in column 752. As explained earlier, the threshold conditions may include values being below a threshold, at a threshold, or above a threshold. Block 794 shows that action signal generator 660 can, in response to receiving an alert condition, alert the operator 260 by using visual control signal generator 684 to generate visual alerts, by using audio control signal generator 686 to generate audio alerts, by using haptic control signal generator 688 to generate haptic alerts, or by using any combination of these. Similarly, as indicated by block 796, controller output generator 670 can generate outputs to other controllers in control system 214 so that those controllers perform the corresponding action identified in column 754. Block 798 shows that operator interface controller 231 can detect and process alert conditions in other ways as well.

Block 900 shows that speech handling system 662 may detect and process inputs invoking speech processing system 658. Block 902 shows that performing speech processing may include the use of dialog management system 680 to conduct a dialog with the operator 260. Block 904 shows that the speech processing may include providing signals to controller output generator 670 so that control operations are automatically performed based upon the speech inputs.

Table 1, below, shows an example of a dialog between operator interface controller 231 and operator 260. In Table 1, operator 260 uses a trigger word or a wakeup word that is detected by trigger detector 672 to invoke speech processing system 658. In the example shown in Table 1, the wakeup word is "Johnny".

TABLE 1

Operator: "Johnny, tell me about current yield"
Operator Interface Controller: "Current yield is 95 bushels/per acre of corn"
Operator: "Johnny, what should I do because of this yield?"
Operator Interface Controller: "Yield is low. Consider speeding up, grain loss will not be significantly affected."

Table 2 shows an example in which speech synthesis component 676 provides an output to audio control signal generator 686 to provide audible updates on an intermittent or periodic basis. The interval between updates may be time-based, such as every five minutes, or coverage or distance-based, such as every five acres, or exception-based, such as when a measured value is greater than a threshold value.

TABLE 2

Operator Interface Controller: "Over last 10 minutes, biomass averaged: 4 tons/acre."
Operator Interface Controller: "Next 1 acre estimated to average 7 tons/acre biomass."
Operator Interface Controller: "Warning: Biomass approaching maximum threshold."
Operator Interface Controller: "Caution: Biomass exceeding maximum threshold.
Mitigation options include: Slowing Machine and Raising Header."
Operator: "Johnny, Raise header"
Operator Interface Controller: "Raising Header to reduce biomass 5% below maximum threshold."

The example shown in Table 3 illustrates that some actuators or user input mechanisms on the touch sensitive display 720 can be supplemented with speech dialog. The example in Table 3 illustrates that action signal generator 660 can generate action signals to automatically mark a high yield area in the field being harvested.

TABLE 3

| |
|---|
| Human: "Johnny, mark high yield area." |
| Operator Interface Controller: "High yield area marked." |

The example shown in Table 4 illustrates that action signal generator 660 can conduct a dialog with operator 260 to begin and end marking of an area based on the yield value.

TABLE 4

| |
|---|
| Human: "Johnny, start marking high yield area." |
| Operator Interface Controller: "Marking high yield area." |
| Human: "Johnny, stop marking high yield area." |
| Operator Interface Controller: "High yield area marking stopped." |

The example shown in Table 5 illustrates that action signal generator 160 can generate signals to mark an area based on the yield value in a different way than those shown in Tables 3 and 4.

TABLE 5

| |
|---|
| Human: "Johnny, mark next 100 feet as a low yield area." |
| Operator Interface Controller: "Next 100 feet marked as a low yield area." |

Returning again to FIG. 12, block 906 illustrates that operator interface controller 231 can detect and process conditions for outputting a message or other information in other ways as well. For instance, other controller interaction system 656 can detect inputs from other controllers indicating that alerts or output messages should be presented to operator 260. Block 908 shows that the outputs can be audio messages. Block 910 shows that the outputs can be visual messages, and block 912 shows that the outputs can be haptic messages. Until operator interface controller 231 determines that the current harvesting operation is completed, as indicated by block 914, processing reverts to block 698 where the geographic location of harvester 100 is updated and processing proceeds as described above to update user interface display 720.

Once the operation is complete, then any desired values that are displayed, or have been displayed on user interface display 720, can be saved. Those values can also be used in machine learning to improve different portions of predictive model generator 210, predictive map generator 212, control zone generator 213, control algorithms, or other items. Saving the desired values is indicated by block 916. The values can be saved locally on agricultural harvester 100, or the values can be saved at a remote server location or sent to another remote system.

It can thus be seen that prior information map is obtained by an agricultural harvester and shows vegetative index or yield values at different geographic locations of a field being harvested. An in-situ sensor on the harvester senses a characteristic that has values indicative of an agricultural characteristic as the agricultural harvester moves through the field. A predictive map generator generates a predictive map that predicts control values for different locations in the field based on the values of the vegetative index or yield in the prior information map and the agricultural characteristic sensed by the in-situ sensor. A control system controls controllable subsystem based on the control values in the predictive map.

A control value is a value upon which an action can be based. A control value, as described herein, can include any value (or characteristics indicated by or derived from the value) that may be used in the control of agricultural harvester 100. A control value can be any value indicative of an agricultural characteristic. A control value can be a predicted value, a measured value, or a detected value. A control value may include any of the values provided by a map, such as any of the maps described herein, for instance, a control value can be a value provided by an information map, a value provided by prior information map, or a value provided predictive map, such as a functional predictive map. A control value can also include any of the characteristics indicated by or derived from the values detected by any of the sensors described herein. In other examples, a control value can be provided by an operator of the agricultural machine, such as a command input by an operator of the agricultural machine.

The present discussion has mentioned processors and servers. In some examples, the processors and servers include computer processors with associated memory and timing circuitry, not separately shown. The processors and servers are functional parts of the systems or devices to which the processors and servers belong and are activated by and facilitate the functionality of the other components or items in those systems.

Also, a number of user interface displays have been discussed. The displays can take a wide variety of different forms and can have a wide variety of different user actuatable operator interface mechanisms disposed thereon. For instance, user actuatable operator interface mechanisms may include text boxes, check boxes, icons, links, drop-down menus, search boxes, etc. The user actuatable operator interface mechanisms can also be actuated in a wide variety of different ways. For instance, the user actuatable operator interface mechanisms can be actuated using operator interface mechanisms such as a point and click device, such as a track ball or mouse, hardware buttons, switches, a joystick or keyboard, thumb switches or thumb pads, etc., a virtual keyboard or other virtual actuators. In addition, where the screen on which the user actuatable operator interface mechanisms are displayed is a touch sensitive screen, the user actuatable operator interface mechanisms can be actuated using touch gestures. Also, user actuatable operator interface mechanisms can be actuated using speech commands using speech recognition functionality. Speech recognition may be implemented using a speech detection device, such as a microphone, and software that functions to recognize detected speech and execute commands based on the received speech.

A number of data stores have also been discussed. It will be noted that the data stores can each be broken into multiple data stores. In some examples, one or more of the data stores may be local to the systems accessing the data stores, one or more of the data stores may all be located remote form a system utilizing the data store, or one or more data stores may be local while others are remote. All of these configurations are contemplated by the present disclosure.

Also, the figures show a number of blocks with functionality ascribed to each block. It will be noted that fewer blocks can be used to illustrate that the functionality ascribed to multiple different blocks is performed by fewer components. Also, more blocks can be used illustrating that the functionality may be distributed among more components. In different examples, some functionality may be added, and some may be removed.

It will be noted that the above discussion has described a variety of different systems, components, logic, and interactions. It will be appreciated that any or all of such systems, components, logic and interactions may be implemented by hardware items, such as processors, memory, or other processing components, including but not limited to artificial intelligence components, such as neural networks, some of which are described below, that perform the functions associated with those systems, components, logic, or interactions. In addition, any or all of the systems, components, logic and interactions may be implemented by software that is loaded into a memory and is subsequently executed by a processor or server or other computing component, as described below. Any or all of the systems, components, logic and interactions may also be implemented by different combinations of hardware, software, firmware, etc., some examples of which are described below. These are some examples of different structures that may be used to implement any or all of the systems, components, logic and interactions described above. Other structures may be used as well.

Figure 14:
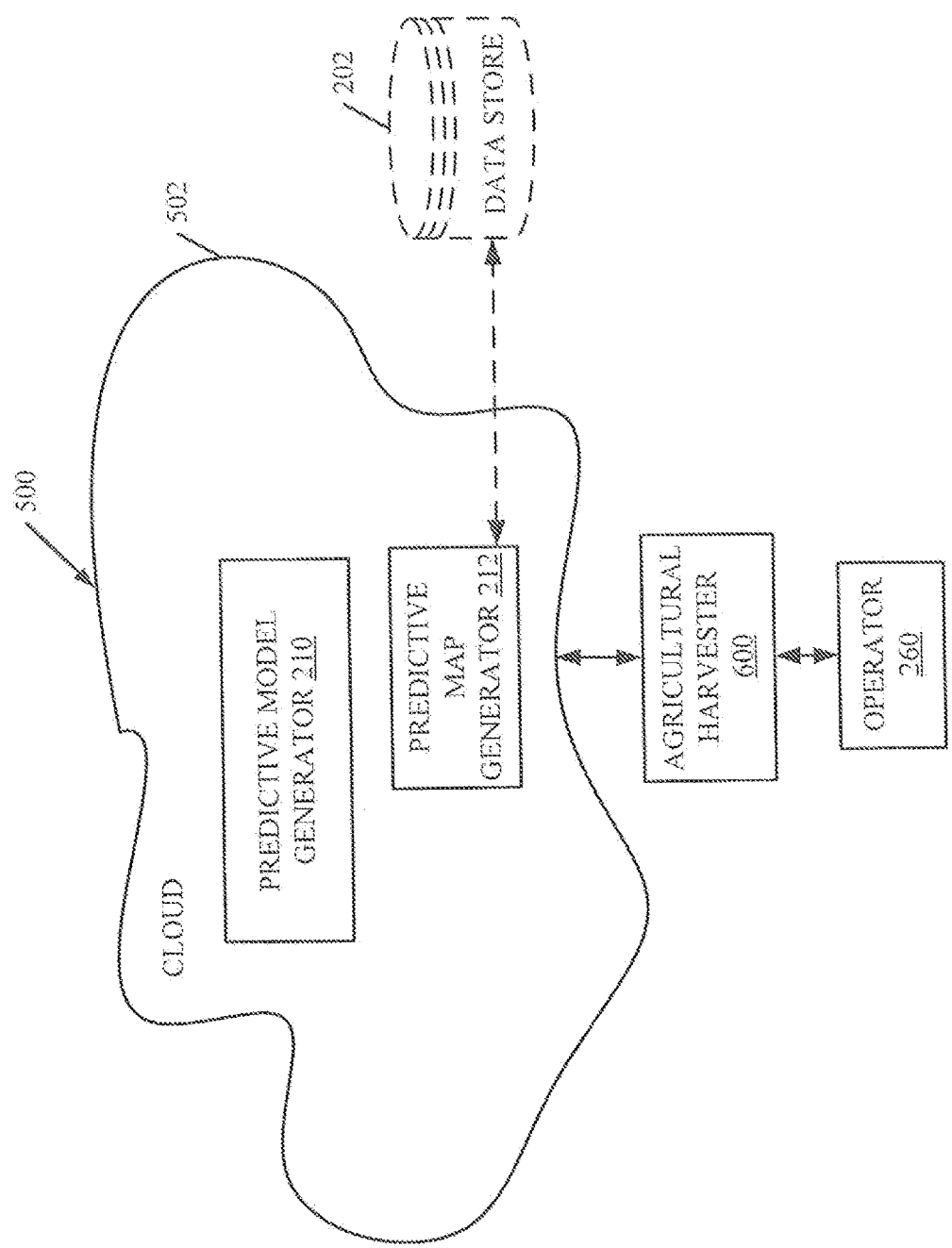
FIG. 14 is a block diagram showing one example of an agricultural harvester in communication with a remote server environment.

FIG. 14 is a block diagram of agricultural harvester 600, which may be similar to agricultural harvester 100 shown in FIG. 2. The agricultural harvester 600 communicates with elements in a remote server architecture 500. In some examples, remote server architecture 500 provides computation, software, data access, and storage services that do not require end-user knowledge of the physical location or configuration of the system that delivers the services. In various examples, remote servers may deliver the services over a wide area network, such as the internet, using appropriate protocols. For instance, remote servers may deliver applications over a wide area network and may be accessible through a web browser or any other computing component. Software or components shown in FIG. 2 as well as data associated therewith, may be stored on servers at a remote location. The computing resources in a remote server environment may be consolidated at a remote data center location, or the computing resources may be dispersed to a plurality of remote data centers. Remote server infrastructures may deliver services through shared data centers, even though the services appear as a single point of access for the user. Thus, the components and functions described herein may be provided from a remote server at a remote location using a remote server architecture. Alternatively, the components and functions may be provided from a server, or the components and functions can be installed on client devices directly, or in other ways.

In the example shown in FIG. 14, some items are similar to those shown in FIG. 2 and those items are similarly numbered. FIG. 14 specifically shows that predictive model generator 210 or predictive map generator 212, or both, may be located at a server location 502 that is remote from the agricultural harvester 600. Therefore, in the example shown in FIG. 14, agricultural harvester 600 accesses systems through remote server location 502.

FIG. 14 also depicts another example of a remote server architecture. FIG. 14 shows that some elements of FIG. 2 may be disposed at a remote server location 502 while others may be located elsewhere. By way of example, data store 202 may be disposed at a location separate from location 502 and accessed via the remote server at location 502. Regardless of where the elements are located, the elements can be accessed directly by agricultural harvester 600 through a network such as a wide area network or a local area network; the elements can be hosted at a remote site by a service; or the elements can be provided as a service or accessed by a connection service that resides in a remote location. Also, data may be stored in any location, and the stored data may be accessed by, or forwarded to, operators, users, or systems. For instance, physical carriers may be used instead of, or in addition to, electromagnetic wave carriers. In some examples, where wireless telecommunication service coverage is poor or nonexistent, another machine, such as a fuel truck or other mobile machine or vehicle, may have an automated, semi-automated, or manual information collection system. As the combine harvester 600 comes close to the machine containing the information collection system, such as a fuel truck prior to fueling, the information collection system collects the information from the combine harvester 600 using any type of ad-hoc wireless connection. The collected information may then be forwarded to another network when the machine containing the received information reaches a location where wireless telecommunication service coverage or other wireless coverage—is available. For instance, a fuel truck may enter an area having wireless communication coverage when traveling to a location to fuel other machines or when at a main fuel storage location. All of these architectures are contemplated herein. Further, the information may be stored on the agricultural harvester 600 until the agricultural harvester 600 enters an area having wireless communication coverage. The agricultural harvester 600, itself, may send the information to another network.

It will also be noted that the elements of FIG. 2, or portions thereof, may be disposed on a wide variety of different devices. One or more of those devices may include an on-board computer, an electronic control unit, a display unit, a server, a desktop computer, a laptop computer, a tablet computer, or other mobile device, such as a palm top computer, a cell phone, a smart phone, a multimedia player, a personal digital assistant, etc.

In some examples, remote server architecture 500 may include cybersecurity measures. Without limitation, these measures may include encryption of data on storage devices, encryption of data sent between network nodes, authentication of people or processes accessing data, as well as the use of ledgers for recording metadata, data, data transfers, data accesses, and data transformations. In some examples, the ledgers may be distributed and immutable (e.g., implemented as blockchain).

Figure 15:
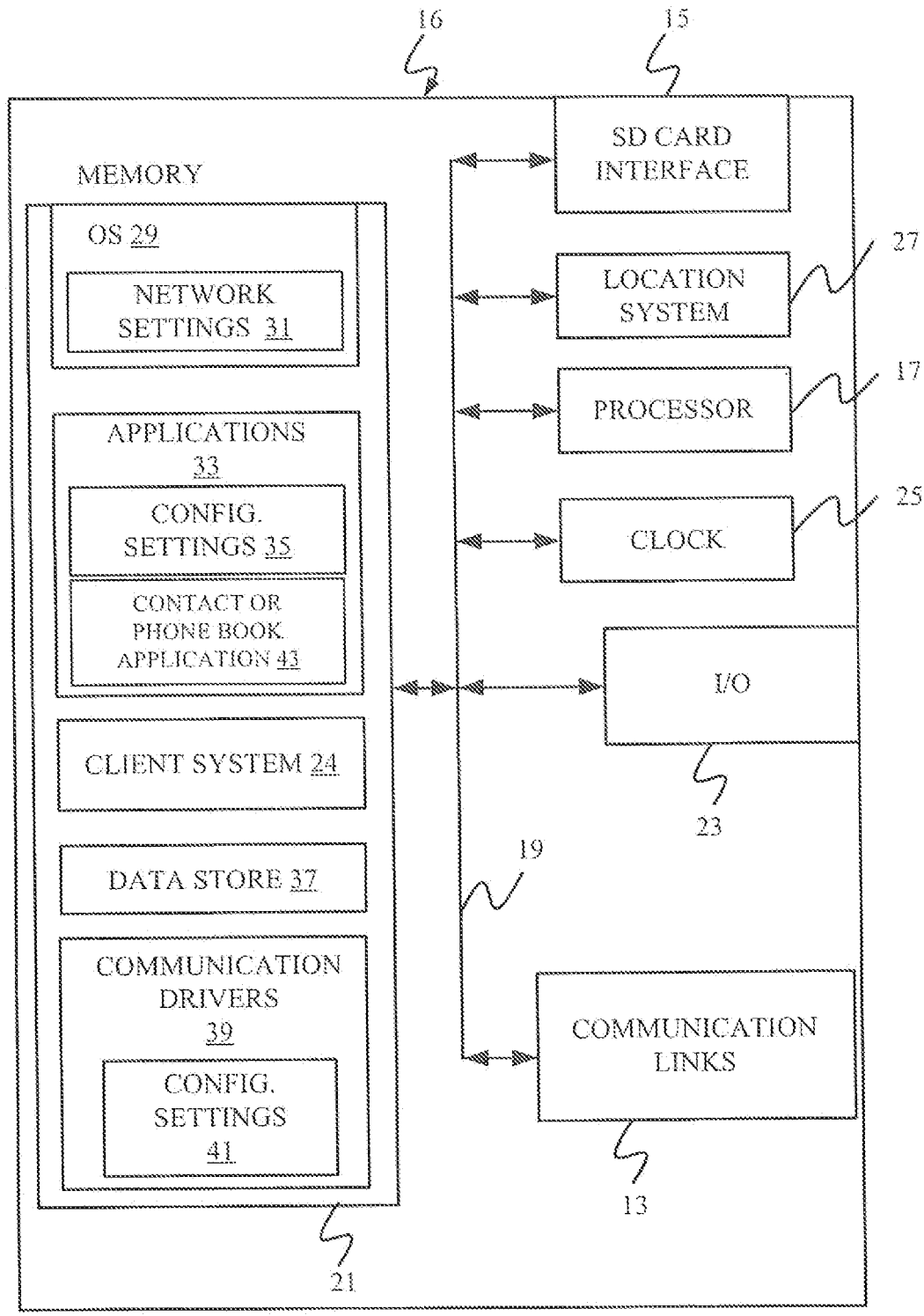
FIGS. 15-17 show examples of mobile devices that can be used in an agricultural harvester.
Figure 16:
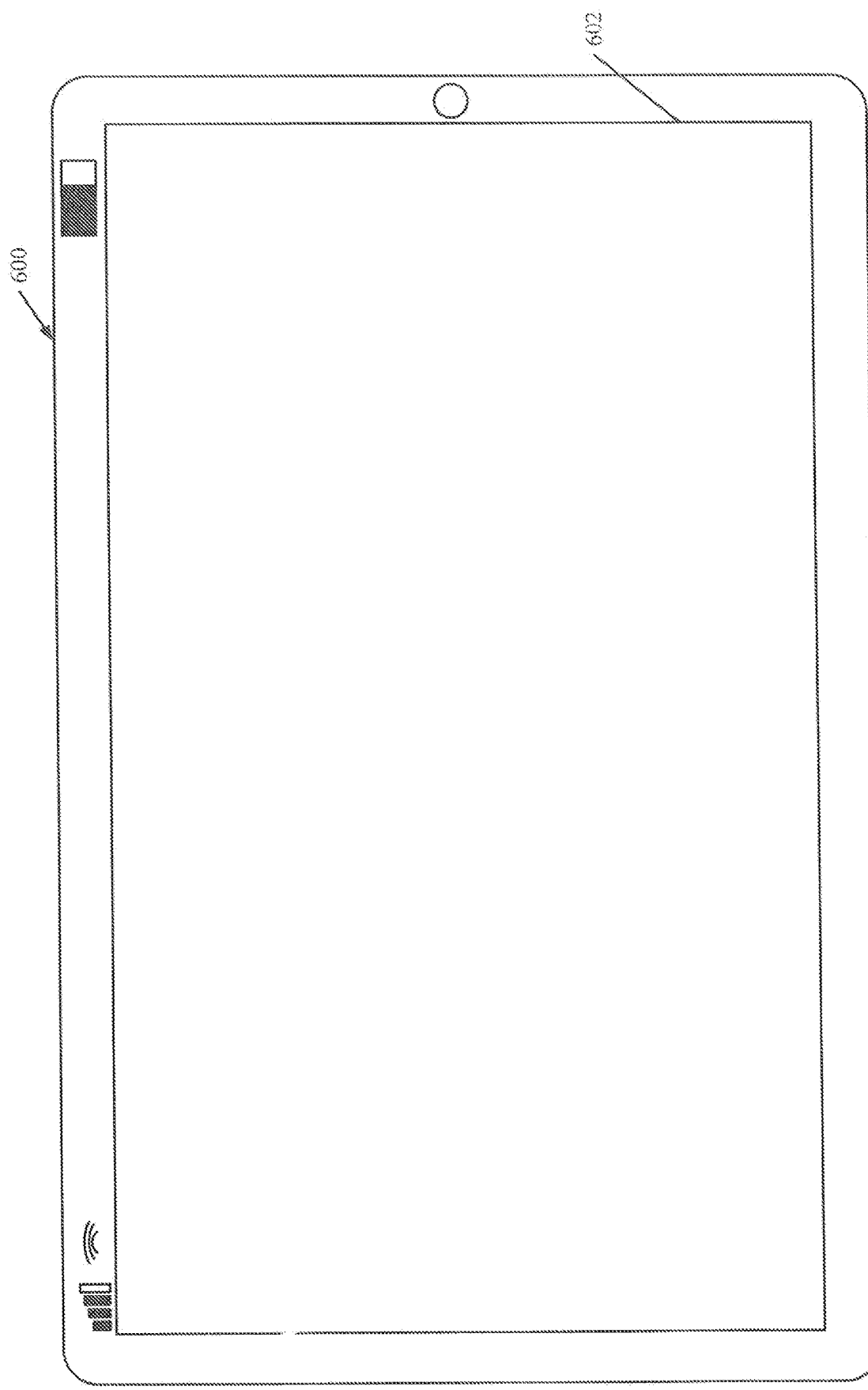
Figure 17:
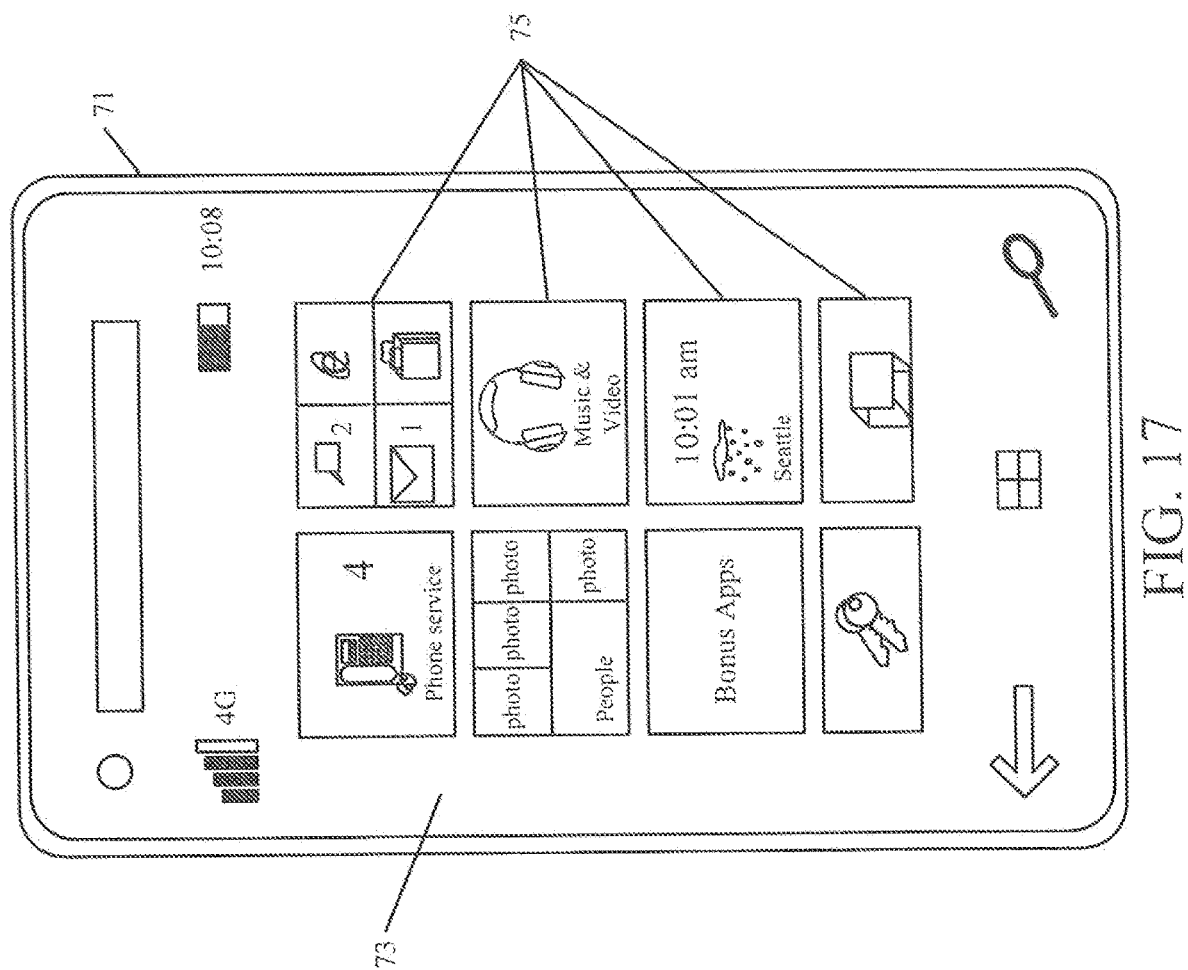

FIG. 15 is a simplified block diagram of one illustrative example of a handheld or mobile computing device that can be used as a user's or client's hand held device 16, in which the present system (or parts of it) can be deployed. For instance, a mobile device can be deployed in the operator compartment of agricultural harvester 100 for use in generating, processing, or displaying the maps discussed above. FIGS. 16-17 are examples of handheld or mobile devices.

FIG. 15 provides a general block diagram of the components of a client device 16 that can run some components shown in FIG. 2, that interacts with them, or both. In the device 16, a communications link 13 is provided that allows the handheld device to communicate with other computing devices and under some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from other FIGS.) along a bus 19 that is also connected to memory 21 and input/output (I/O) components 23, as well as clock 25 and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. Location system 27 can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. Memory 21 may also include computer storage media (described below). Memory 21 stores computer readable instructions that, when executed by processor 17, cause the processor to perform computer-implemented steps or functions according to the instructions. Processor 17 may be activated by other components to facilitate their functionality as well.

FIG. 16 shows one example in which device 16 is a tablet computer 600. In FIG. 16, computer 601 is shown with user interface display screen 602. Screen 602 can be a touch screen or a pen-enabled interface that receives inputs from a pen or stylus. Tablet computer 600 may also use an on-screen virtual keyboard. Of course, computer 601 might also be attached to a keyboard or other user input device through a suitable attachment mechanism, such as a wireless link or USB port, for instance. Computer 601 may also illustratively receive voice inputs as well.

FIG. 17 is similar to FIG. 16 except that the device is a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 18:
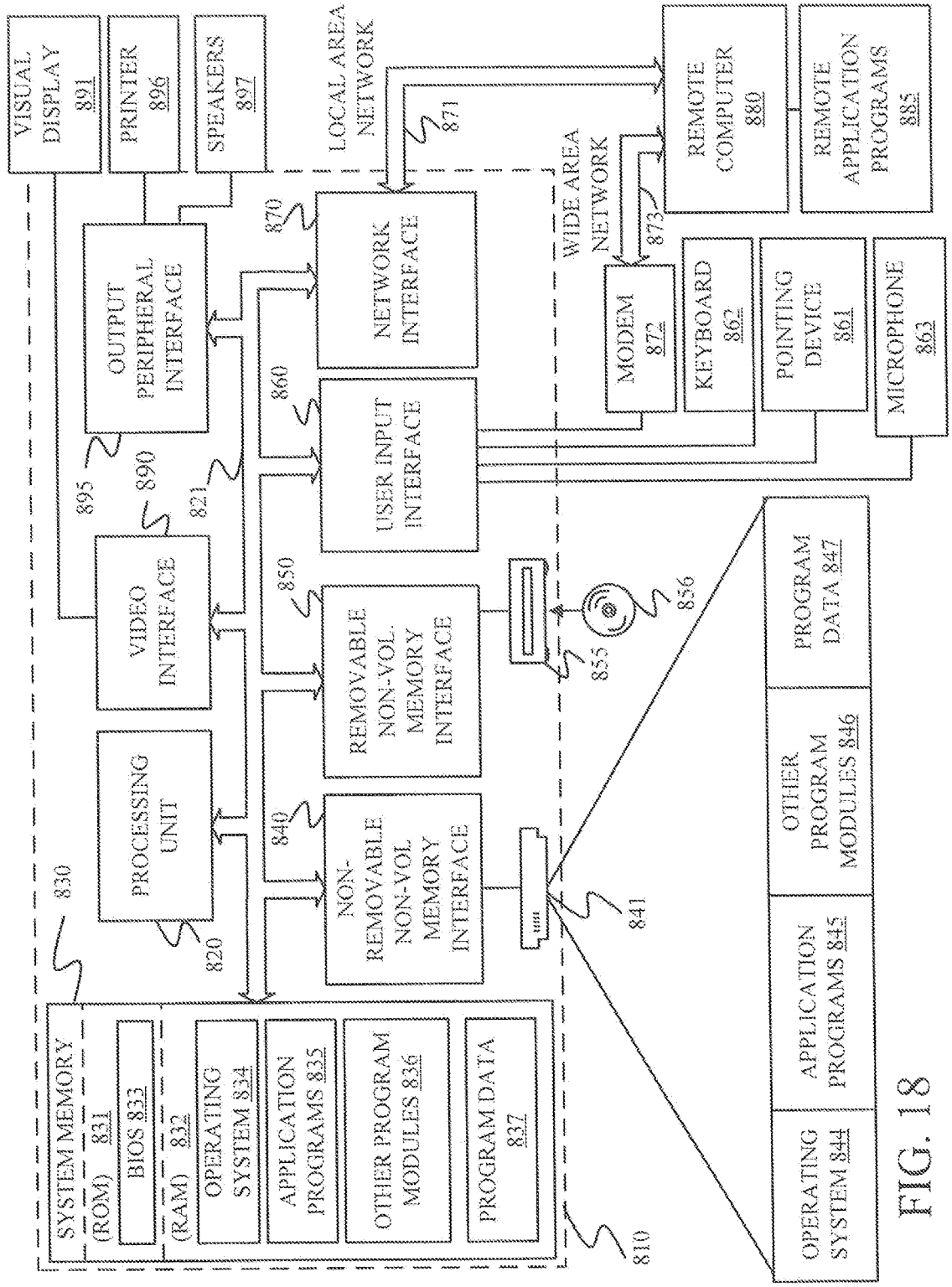
FIG. 18 is a block diagram showing one example of a computing environment that can be used in an agricultural harvester

FIG. 18 is one example of a computing environment in which elements of FIG. 2 can be deployed. With reference to FIG. 18, an example system for implementing some embodiments includes a computing device in the form of a computer 810 programmed to operate as discussed above. Components of computer 810 may include, but are not limited to, a processing unit 820 (which can comprise processors or servers from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 2 can be deployed in corresponding portions of FIG. 18.

Computer 810 typically includes a variety of computer readable media. Computer readable media may be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. Computer readable media includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory or both such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data or program modules or both that are immediately accessible to and/or presently being operated on by processing unit 820. By way of example, and not limitation, FIG. 18 illustrates operating system 834, application programs 835, other program modules 836, and program data 837.

The computer 810 may also include other removable/non-removable volatile/nonvolatile computer storage media. By way of example only, FIG. 18 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 18, provide storage of computer readable instructions, data structures, program modules and other data for the computer 810. In FIG. 18, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a controller area network—CAN, local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 18 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is an agricultural work machine comprising:
a communication system that receives an information map that includes values of a yield corresponding to different geographic locations in a field;
a geographic position sensor that detects a geographic location of the agricultural work machine;
an in-situ sensor that detects a value of an agricultural characteristic corresponding to a geographic location;
a predictive map generator that generates a functional predictive agricultural map of the field that maps predictive control values to the different geographic locations in the field based on the values of the yield in the information map and based on the value of the agricultural characteristic;
a controllable subsystem; and
a control system that generates a control signal to control the controllable subsystem based on the geographic position of the agricultural work machine and based on the control values in the functional predictive agricultural map.

Example 2 is the agricultural work machine of any or all previous examples, wherein the predictive map generator comprises:
a predictive yield map generator that generates a functional predictive yield map that maps predictive agricultural yield values to the different geographic locations in the field.

Example 3 is the agricultural work machine of any or all previous examples, wherein the control system comprises:
a feed rate controller that generates a feed rate control signal based on the detected geographic location and the functional predictive yield map and controls the controllable subsystem based on the feed rate control signal to control a feed rate of material through the agricultural work machine.

Example 4 is the agricultural work machine of any or all previous examples, wherein the predictive map generator comprises:
a predictive biomass map generator that generates a functional predictive biomass map that maps predictive biomass values to the different geographic locations in the field.

Example 5 is the agricultural work machine of any or all previous examples, wherein the control system comprises:
a settings controller that generates a speed control signal based on the detected geographic location and the functional predictive biomass map and controls the controllable subsystem based on the speed control signal to control a speed of the agricultural work machine.

Example 6 is the agricultural work machine of any or all previous examples, wherein the predictive map generator comprises:
a predictive operator command map generator that generates a functional predictive operator command map that maps predictive operator commands to the different geographic locations in the field.

Example 7 is the agricultural work machine of any or all previous examples, wherein the control system comprises:
a settings controller that generates an operator command control signal indicative of an operator command based on the detected geographic location and the functional predictive operator command map and controls the controllable subsystem based on the operator command control signal to execute the operator command.

Example 8 is the agricultural work machine of any or all previous examples, wherein the information map comprises a historical yield map that maps historical yield values to the different geographic locations in the field.

Example 9 is the agricultural work machine of any or all previous examples, wherein the control system further comprises:
an operator interface controller that generates a user interface map representation of the functional predictive agricultural map, the user interface map representation comprising a field portion with one or more markers indicating the predictive control values at one or more geographic locations on the field portion.

Example 10 is the agricultural work machine of any or all previous examples, wherein the operator interface controller generates the user interface map representation to include an interactive display portion that displays a value display portion indicative of a selected value, an interactive threshold display portion indicative of an action threshold, and an interactive action display portion indicative of a control action to be taken when one of the predictive control values satisfies the action threshold in relation to the selected value, the control system generating the control signal to control the controllable subsystem based on the control action.

Example 11 is a computer implemented method of controlling an agricultural work machine comprising:
obtaining an information map that includes values of a yield corresponding to different geographic locations in a field;
detecting a geographic location of the agricultural work machine;
detecting, with an in-situ sensor, a value of an agricultural characteristic corresponding to a geographic location;
generating a functional predictive agricultural map of the field that maps predictive control values to the different geographic locations in the field based on the values of the yield in the information map and based on the value of the agricultural characteristic; and
controlling a controllable subsystem based on the geographic position of the agricultural work machine and based on the control values in the functional predictive agricultural map.

Example 12 is the computer implemented method of any or all previous examples, wherein generating a functional predictive map comprises:
generating a functional predictive biomass map that maps predictive biomass of material to the different geographic locations in the field.

Example 13 is the computer implemented method of any or all previous examples, wherein controlling a controllable subsystem comprises:
generating a feed rate control signal based on the detected geographic location and the functional predictive biomass map; and
controlling the controllable subsystem based on the feed rate control signal to control a feed rate of material through the agricultural work machine.

Example 14 is the computer implemented method of any or all previous examples, wherein generating a functional predictive map comprises:
generating a functional predictive machine speed map that maps predictive machine speed values to the different geographic locations in the field.

Example 15 is the computer implemented method of any or all previous examples, wherein controlling a controllable subsystem comprises:
generating a speed control signal based on the detected geographic location and the functional predictive machine speed map; and
controlling the controllable subsystem based on the speed control signal to control a speed of the agricultural work machine.

Example 16 is the computer implemented method of any or all previous examples, wherein generating a functional predictive map comprises:
generating a functional predictive operator command map that maps predictive operator commands to the different geographic locations in the field.

Example 17 is the computer implemented method of any or all previous examples, wherein controlling the controllable subsystem comprises:
generating an operator command control signal indicative of an operator command based on the detected geographic location and the functional predictive operator command map; and
controlling the controllable subsystem based on the operator command control signal to execute the operator command.

Example 18 is the computer implemented method of any or all previous examples and further comprising:
generating a predictive agricultural model that models a relationship between the yield and the agricultural characteristic based on a value of the yield in the information map at the geographic location and a value of the agricultural characteristic sensed by the in-situ sensor at the geographic location, wherein generating the functional predictive agricultural map comprises generating the functional predictive agricultural map based on the values of the yield in the information map and based on the predictive agricultural model.

Example 19 is an agricultural work machine comprising:
a communication system that receives a information map that includes values of yield corresponding to different geographic locations in a field;
a geographic position sensor that detects a geographic location of the agricultural work machine;
an in-situ sensor that detects a value of an agricultural characteristic corresponding to a geographic location;
a predictive model generator that generates a predictive agricultural model that models a relationship between the yield and the agricultural characteristic based on a value of the yield in the information map at the geographic location and a value of the agricultural characteristic sensed by the in-situ sensor at the geographic location;
a predictive map generator that generates a functional predictive agricultural map of the field that maps predictive control values to the different geographic locations in the field based on the values of the yield in the information map and based on the predictive agricultural model;
a controllable subsystem; and
a control system that generates a control signal to control the controllable subsystem based on the geographic position of the agricultural work machine and based on the control values in the functional predictive agricultural map.

Example 20 is the agricultural work machine of any or all previous examples, wherein the control system comprises at least one of:
a feed rate controller that generates a feed rate control signal based on the detected geographic location and the functional predictive agricultural map and controls the controllable subsystem based on the feed rate control signal to control a feed rate of material through the agricultural work machine;
a settings controller that generates a speed control signal based on the detected geographic location and the functional predictive agricultural map and controls the controllable subsystem based on the speed control signal to control a speed of the agricultural work machine; and
a settings controller that generates an operator command control signal indicative of an operator command based on the detected geographic location and the functional predictive agricultural map and controls the controllable subsystem based on the operator command control signal to execute the operator command.

Although the subject matter has been described in language specific to structural features or methodological acts, it is to be understood that the subject matter defined in the appended claims is not necessarily limited to the specific features or acts described above. Rather, the specific features and acts described above are disclosed as example forms of the claims.

What is claimed is:
1. An agricultural work machine comprising;
a controllable subsystem;
a communication system configured to obtain an information map that includes yield values corresponding to different geographic locations in a field;
an in-situ sensor configured detects a value of an agricultural characteristic corresponding to a geographic location;
one or more processors;
memory; and
computer executable instructions, stored in the memory, that, when executed by the one or more processors, configure the one or more processors to:
generate a predictive agricultural model that models a relationship between the agricultural characteristic and yield based on the value of the agricultural characteristic, detected by the in-situ sensor, corresponding to the geographic location and a yield value in the information map corresponding to the geographic location; and
control the controllable subsystem based on the predictive agricultural model.

2. The agricultural work machine of claim 1, wherein the computer executable instructions, when executed by the one or more processors, further configure the one or more processors to:
generate a functional predictive agricultural map of the field that maps predictive values of the agricultural characteristic to the different geographic locations in the field based on the yield value in the information map and based on the predictive agricultural model; and
control the controllable subsystem based on the functional predictive agricultural map.

3. The agricultural work machine of claim 1, wherein the information map is derived from vegetative index data of the field.

4. The agricultural work machine of claim 1, wherein the in-situ sensor is configured to detect, as the value of the agricultural characteristic, a biomass value corresponding to the geographic location and wherein the predictive agricultural model models, as the relationship, a relationship between biomass and yield based on the value of biomass, detected by the in-situ sensor, corresponding to the geographic location and the yield value in the information map corresponding to the geographic location.

5. The agricultural work machine of claim 1, wherein the in-situ sensor is configured to detect, as the value of the agricultural characteristic, an operator input, indicative of an operator commanded setting of the agricultural work machine, corresponding to the geographic location and wherein the predictive agricultural model models, as the relationship, a relationship between operator input and yield based on the operator input, detected by the in situ sensor, corresponding to the geographic location and the yield value in the information map corresponding to the geographic location.

6. The agricultural work machine of claim 1, wherein the information map comprises a historical yield map that includes, as values of yield, historical values of yield corresponding to the different geographic locations in the field.

7. The agricultural work machine of claim 6, wherein the in-situ sensor is configured to detect, as the value of the agricultural characteristic, an in-situ yield value corresponding to the geographic location and wherein the predictive agricultural model models, as the relationship, a relationship between in-situ yield and historical yield based on the in-situ yield value, detected by the in-situ sensor, corresponding to the geographic location and a historical yield value in the information map corresponding to the geographic location.

8. The agricultural work machine of claim 1, wherein the controllable subsystem is controlled to control a setting of the of the agricultural work machine.

9. The agricultural work machine of claim 8, wherein the setting comprises one of:
- a rotor speed setting;
- a thresher clearance setting;
- a header position setting;
- a cleaning fan speed setting;
- an agricultural work machine speed setting;
- a sieve setting; or
- a chaffer setting.

10. A computer implemented method of controlling an agricultural work machine comprising:
- obtaining an information map that includes yield values corresponding to different geographic locations in a field;
- detecting, with an in-situ sensor, a value of an agricultural characteristic corresponding to a geographic location;
- generating a predictive agricultural model that models a relationship between the agricultural characteristic and yield based on the value of the agricultural characteristic, detected by the in-situ sensor, corresponding to the geographic location and a yield value, in the information map, corresponding to the geographic location; and
- controlling a controllable subsystem of the agricultural work machine based on the predictive agricultural model.

11. The computer implemented method of claim 10 and further comprising generating a functional predictive agricultural map of the field that maps predictive values of the agricultural characteristic to the different geographic locations in the field based on the yield values in the information map and based on the predictive agricultural model,
wherein controlling the controllable subsystem comprises controlling the controllable subsystem based on the functional predictive agricultural map.

12. The computer implemented method of claim 11, wherein detecting, with the in-situ sensor, the value of the agricultural characteristic corresponding to the geographic location comprises detecting, with the in-situ sensor, as the value of the agricultural characteristic, a biomass value corresponding to the geographic location, and
wherein generating the predictive agricultural model comprises, generating the predictive agricultural model modeling, as the relationship, a relationship between biomass and yield based on the biomass value, detected by the in-situ sensor, corresponding to the geographic location and the yield value, in the information map, corresponding to the geographic location and as being configured to receive an input yield value as a model input and to generate a predictive biomass value as a model output based on the relationship.

13. The computer implemented method of claim 11, wherein detecting, with the in-situ sensor, the value of the agricultural characteristic corresponding to the geographic location comprises detecting, with the in-situ sensor, as the value of the agricultural characteristic, an operator input, indicative of an operator commanded setting of the agricultural work machine, corresponding to the geographic location, and
wherein generating the predictive agricultural model comprises, generating the predictive agricultural model modeling, as the relationship, a relationship between operator input and yield based on the operator input, detected by the in-situ sensor, corresponding to the geographic location and the yield value, in the information map, corresponding to the geographic location and as being configured to receive an input yield value as a model input and to generate a predictive operator input as a model output based on the relationship.

14. The computer implemented method of claim 11, wherein obtaining the information map that includes yield values corresponding to different geographic locations in the field, comprises obtaining, as the information map, a historical yield map that includes historical yield values corresponding to different geographic locations in the field,
wherein detecting, with the in-situ sensor, the value of the agricultural characteristic corresponding to the geographic location comprises detecting, with the in-situ sensor, as the value of the agricultural characteristic, an in-situ yield value corresponding to the geographic location, and
wherein generating the predictive agricultural model comprises, generating the predictive agricultural model modeling, as the relationship, a relationship between in-situ yield and historical yield based on the in-situ yield, detected by the in-situ sensor, corresponding to the geographic location and a historical yield value, in the historical yield map, corresponding to the geographic location and as being configured to receive an input historical yield value as a model input and to generate a predictive in-situ yield value as a model output based on the relationship.

15. The computer implemented method of claim 10, wherein controlling the controllable subsystem comprises:
- generating a setting control signal based on the predictive agricultural model; and
- controlling the controllable subsystem based on the setting control signal to control a setting of the agricultural work machine.

16. The computer implemented method of claim 10, wherein controlling the controllable subsystem comprises:
- generating a speed control signal based on the predictive agricultural model; and
- controlling the controllable subsystem based on the speed control signal to control a speed of the agricultural work machine.

17. The computer implemented method of claim 10, wherein controlling the controllable subsystem comprises:
- generating a feed rate control signal based on the predictive agricultural model; and
- controlling the controllable subsystem based on the feed rate control signal to control feed rate of material through the agricultural work machine.

18. An agricultural system comprising:
- a communication system configured to receive an information map that includes yield values corresponding to different geographic locations in a field;
- an in-situ sensor configured to detect a value of an agricultural characteristic corresponding to a geographic location;
- one or more processors;
- memory; and
- computer executable instructions, stored in the memory, that, when executed by the one or more processors, configure the one or more processors to:
    - generate a predictive agricultural model that models a relationship between the agricultural characteristic and yield based on the value of the agricultural characteristic, detected by the in-situ sensor, corresponding to the geographic location and a yield value in the information map corresponding to the geographic location; and control a controllable subsystem on an agricultural work machine based on the predictive agricultural model.

19. The agricultural system of claim 18, wherein the computer executable instructions, when executed by the one or more processors, further configure the one or more processors to:

generate a functional predictive agricultural map of the field that maps predictive values of the agricultural characteristic to the different geographic locations in the field based on the yield values in the information map and based on the predictive agricultural model; and control the controllable subsystem on the agricultural work machine based on the functional predictive agricultural map.

20. The agricultural system of claim 18, wherein the controllable subsystem is controlled based on the predictive agricultural model to controllably actuate one of:

ground engaging components of the agricultural work machine;

a chopper of the agricultural work machine;

a spreader of the agricultural work machine;

a threshing rotor of the agricultural work machine;

a sieve of the agricultural work machine;

a chaffer of the agricultural work machine;

concaves of the agricultural work machine;

a discharge beater of the agricultural work machine;

a tailings elevator of the agricultural work machine;

a grain elevator of the agricultural work machine;

a header of the agricultural work machine;

a component of the header of the agricultural work machine; or a cleaning fan of the agricultural work machine.

* * * * *